(12) United States Patent
Diwan et al.

(10) Patent No.: US 8,828,941 B2
(45) Date of Patent: Sep. 9, 2014

(54) COMPOSITION AND METHOD FOR THE TREATMENT OR PREVENTION OF SPINAL DISORDERS

(75) Inventors: Ashish Diwan, Sydney (AU); Divya Diwan, Sydney (AU)

(73) Assignee: Divya Diwan, Arlington, VA (US)

( * ) Notice: Subject to any disclaimer, the term of this patent is extended or adjusted under 35 U.S.C. 154(b) by 1327 days.

(21) Appl. No.: 12/528,235

(22) PCT Filed: Feb. 22, 2008

(86) PCT No.: PCT/AU2008/000242
§ 371 (c)(1),
(2), (4) Date: Feb. 11, 2011

(87) PCT Pub. No.: WO2008/101300
PCT Pub. Date: Aug. 28, 2008

(65) Prior Publication Data
US 2011/0144718 A1    Jun. 16, 2011

Related U.S. Application Data

(60) Provisional application No. 60/903,131, filed on Feb. 23, 2007, provisional application No. 61/012,712, filed on Dec. 10, 2007.

(51) Int. Cl.
| | |
|---|---|
| *A61P 19/00* | (2006.01) |
| *A61K 38/18* | (2006.01) |
| *C07K 14/51* | (2006.01) |
| *A61F 5/00* | (2006.01) |
| *A61K 38/17* | (2006.01) |
| *A61K 9/00* | (2006.01) |

(52) U.S. Cl.
CPC .............. *A61K 38/18* (2013.01); *A61K 38/1709* (2013.01); *A61K 9/0085* (2013.01)
USPC .............. 514/17.1; 514/8.8; 530/399; 607/51

(58) Field of Classification Search
None
See application file for complete search history.

(56) References Cited

U.S. PATENT DOCUMENTS

| | | |
|---|---|---|
| 4,898,891 A | 2/1990 | Lavie et al. |
| 2002/0173851 A1 | 11/2002 | McKay |
| 2004/0137088 A1 | 7/2004 | Koch et al. |
| 2004/0191330 A1 | 9/2004 | Keefe et al. |
| 2005/0267577 A1* | 12/2005 | Trieu .......................... 623/17.11 |
| 2007/0093905 A1* | 4/2007 | O'Neil et al. .............. 623/17.16 |

FOREIGN PATENT DOCUMENTS

| | | |
|---|---|---|
| AU | 2009217410 | 10/2009 |
| WO | 9526198 | 10/1995 |
| WO | 9817330 | 4/1998 |
| WO | 9834655 | 8/1998 |
| WO | 2005084701 | 9/2005 |
| WO | 2005115438 | 12/2005 |
| WO | WO 2005/115438 A1 * | 12/2005 |
| WO | 2007142818 | 12/2007 |
| WO | 2008037262 | 4/2008 |

OTHER PUBLICATIONS

Shen et al., (2009) "BMP-13 Emerges as a Potential Inhibitor of Bone Formation" International Journal of Biological Sciences, 5(2):192-200.
Cambazard (1998) "Traitements symptomatiques locaux et generaux de la varicelle et du zona (en dehors des antalgiques et des antiviraux" Med Mal Infect 28(11):810-816.
Sagripanti et al. (1997) "Mechanism of copper-mediated inactivation of herpes simplex virus" Antimicrob Agents Chemother 41(4):812-817.
Wei et al. (2009) "BMP13 prevents the effects of annular injury in an ovine model" Int J Biol Sci 5(5):388-396.

* cited by examiner

*Primary Examiner* — Xiaozhen Xie
(74) *Attorney, Agent, or Firm* — Michael B. Rubin; Carol L. Francis; Bozicevic, Field & Francis LLP

(57) ABSTRACT

The present invention provides compositions of matter suitable for the prevention of and/or treatment of a spinal disorder and/or spinal pain, e.g., caused by and/or associated with intervertebral disc (IVD) degeneration, and methods of treatment of a spinal disorder and/or spinal pain. For example, the compositions of the present invention comprise a modulator of growth differentiation factor (GDF)-6 signaling sufficient to reduce or prevent or delay IVD degeneration and/or to enhance or induce IVD regeneration. The present invention also provides medical devices comprising such compositions, and methods of treatment making use of such compositions.

14 Claims, 34 Drawing Sheets

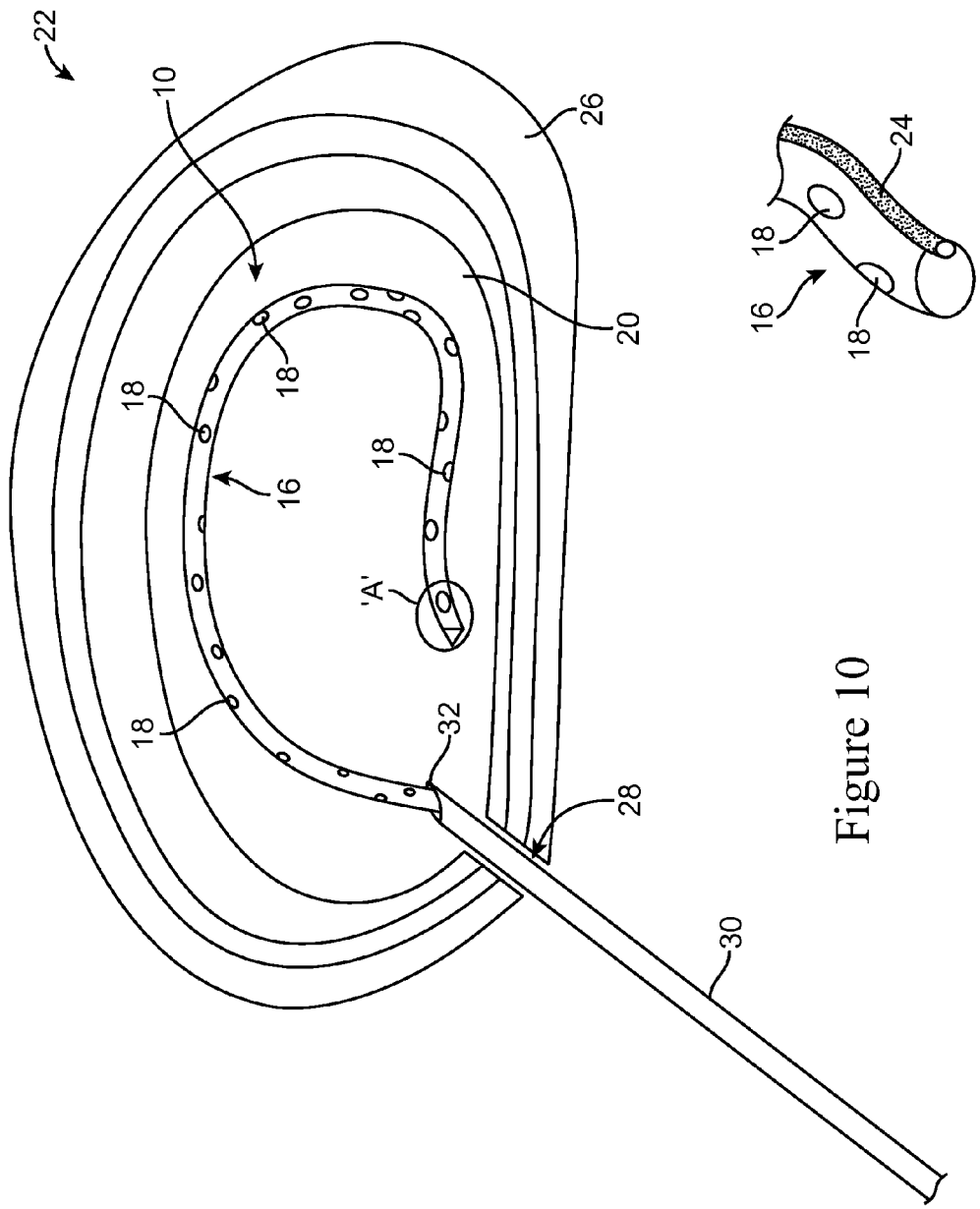

COMPOSITION AND METHOD FOR THE TREATMENT OR PREVENTION OF SPINAL DISORDERS

RELATED APPLICATION DATA

The present application claims priority from U.S. Ser. No. 60/303,131 filed in the United States Patent and Trademark Office on 23 Feb. 2007 entitled "Composition and method for the treatment and prevention of spinal disorders", and U.S. Ser. No. 61/012,712 filed in the United States Patent and Trademark Office on 10 Dec. 2007 entitled "Composition and method for the treatment and prevention of spinal disorders II", the contents of which are incorporated herein by reference.

FIELD OF THE INVENTION

The present invention relates to compositions of matter for the prevention of and/or treatment of a spinal disorder and/or spinal pain, e.g., caused by and/or associated with intervertebral disc degeneration and methods of treatment of a spinal disorder and/or spinal pain.

BACKGROUND OF THE INVENTION

1. General

The following publications provide conventional techniques of molecular biology. Such procedures are described, for example, in the following texts that are incorporated by reference:
1) Sambrook, Fritsch & Maniatis, Molecular Cloning: A Laboratory Manual, Cold Spring Harbor Laboratories, New York, Second Edition (1989), whole of Vols I, II, and III;
2) DNA Cloning: A Practical Approach, Vols. I and II (D. N. Glover, ed., 1985), IRL Press, Oxford, whole of text;
3) Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4) Animal Cell Culture: Practical Approach, Third Edition (John R. W. Masters, ed., 2000), ISBN 0199637970, whole of text;
5) J. F. Ramalho Ortigão, "The Chemistry of Peptide Synthesis" In: Knowledge database of Access to Virtual Laboratory website (Interactiva, Germany);
6) Sakakibara, D., Teichman, J., Lien, E. Land Fenichel, R. L. (1976). *Biochem. Biophys. Res. Commun.* 73 336-342
7) Merrifield, R. B. (1963). *J. Am. Chem. Soc.* 85, 2149-2154.
8) Barany, G. and Merrifield, R. B. (1979) in *The Peptides* (Gross, E. and Meienhofer, J. eds.), vol. 2, pp. 1-284, Academic Press, New York.
9) Bodanszky, M. (1984) *Principles of Peptide Synthesis*, Springer-Verlag, Heidelberg.
10) Bodanszky, M. & Bodanszky, A. (1984) *The Practice of Peptide Synthesis*, Springer-Verlag, Heidelberg.

2. Description of Related Art

Persistent back pain poses a significant economic burden to society, mainly in terms of the large number of work days lost by patients who develop chronic back pain. The major cause of persistent back pain is intervertebral disc (IVD) degeneration. In this respect, in USA alone approximately 5.7 million people are diagnosed with IVD degeneration each year.

Intervertebral Discs (IVDs)

An IVD is a specialized connective tissue composed of a pad of fibrocartilage found between the bony vertebrae of the spine. IVDs act as a shock absorber to cushion the compressive, rotational and tensile forces applied to the vertebral column. An IVD comprises at least three elements: a tough outer tissue called the annulus fibrosus (AF) comprising concentric layers of intertwined annular bands comprising primarily collagen type I fibers; a nucleus pulposus (NP) within the AF, comprising a viscous gel containing proteoglycan and water held loosely together by an irregular network of collagen type II and elastin fibers; and flat, circular plates of cartilage that connect the vertebrae above and below the disc to the AF. The major proteoglycan found in the NP is the glucosaminoglycan aggrecan which is high in chondroitin sulfate and keratin sulfate. This proteoglycan provides osmotic properties needed to resist compression in the disc (Adams and Roughley, *Spine* 31: 2151-2161, 2006). Cells of the NP are initially notochord cells that are gradually replaced during childhood by rounded cells resembling the chondrocytes of articular cartilage. Cells of the AF are fibroblast-like, elongated parallel to the collagen fibers in the AF. Cell density declines with age and is extremely low in adults, especially in the NP.

Fibrocartilage found in an IVD differs to other forms of cartilage, e.g., hyaline cartilage or elastic cartilage. For example, the fibrocartilage found in IVDs contain cartilage-1 or type-1 cartilage, whereas this form of cartilage does not occur in hyaline cartilage or elastic cartilage. Moreover, the extracellular matrix within an IVD differs from that found in other cartilage, e.g. hyaline cartilage, in so far as it contains a high proteoglycan to collagen ratio, e.g., extracellular matrix of IVD has a ratio of proteoglycan to collagen of about 27:1, whereas hyaline cartilage has a ratio of about 2:1 (Mwale et al., *European Cells and Materials*, 8: 58-64, 2004). The increased level of proteoglycan relative to collagen in an IVD explains to some degree the gelatinous nature of an IVD, which is required for transmitting load applied to the IVD and providing the shock absorbing nature of these organs. In contrast to IVD, other forms of cartilage, e.g., hyaline cartilage or articular cartilage operate in isolation and must retain their own shape and, as a consequence, a higher concentration of collagen to proteoglycan is desired to provide such a firm and resilient nature (Mwale et al., supra).

At the microscopic level proteoglycans of IVD extracellular matrix also differ from those of other forms of cartilage, including articular cartilage, nasal cartilage, growth plate cartilage and menesci. For example, articular cartilage nasal cartilage, growth plate cartilage and menesci contain large aggregates of proteoglycan formed from hyaluronic acid central filaments in addition to large nonaggregated monomers. In contrast to these cartilages, IVDs contain short non-aggregated proteoglycan monomers and clusters of monomers without central filaments (Buckwalter et al., *J. Orthop. Res.*, 7: 146-151, 1989). These differences in composition of IVDs and other forms of cartilage are indicative of significant differences in collagen and/or proteoglycan metabolism between these tissues.

IVD degeneration is associated with a series of biochemical and morphologic changes that combine to alter the biomechanical properties of the disc. During IVD degeneration, the concentration of proteoglycans in the NP and the water retaining potential of the disc decrease dramatically. There are also changes in the collagen content of the NP as the synthesis of type II collagen declines and the synthesis of less tensile type I collagen increases. Another change is a shift in phenotype of the differentiated chondrocyte of the NP into a more fibrotic type.

IVD Development

In adult life, events unfolding as a consequence of injury to the disc may mimic some of the molecular events that control the development of the disc. Development of the disc is under tight molecular control both temporally and spatially. Notochordal cells are involved in the development of the spinal cord and vertebra and they also contribute towards the patterning and differentiation of the IVDs. During gastrulation, the axial mesoderm gives rise to the notochord and somites develop into two parts: a schlerotome and a dermomyotome. The cells of the schlerotome are responsible for the formation of the spine and the IVD as the schlerotomes migrate toward and around the notochord and neural tube, and later separate into areas of loosely packed cells which go on to form the NP and a densely packed cells which form the AF.

IVD Related Disorders

Kippel Feil Syndrome (KFS) is a congenital condition characterized by the fusion of two or more cervical vertebrae (Type I-III; Kaplan et al., The Spine Journal 2005 5:564-576). This abnormality is the result of a failure of proper segmentation of vertebrae in the cervical region during embryonic development (Clark et al., 1998, Pediatr Radiol 28:967-974). In KFS the IVD(s) are not developed (hypo/oligogenesis) or there is an agenesis of the disc(s). Notwithstanding that a number of de novo PAXJ missense mutations, as well as PAX1 haploinsufficiency, i.e., reduced expression of PAXJ, have been associated with KFS, no definitive genetic basis for KFS has yet been identified.

Fibrodysplasia ossificans progressive (FOP) is a rare autosomal dominant disorder of connective tissue whereby patients also present with cervical spine abnormalities. FOP, a condition where there is excessive bone formation is often misdiagnosed for KFS, which has been identified by the present inventor as being an hypo/oligogenesis of the disc. Knockout mice which do not express the bone morphogenetic protein (BMP) antagonist noggin, exhibit a phenotype almost identical to FOP patients. Whilst the noggin gene (NOG) is not mutated in FOP, overactivity of the BMP pathway (i.e., enhanced BMP signaling) has been suggested as the molecular pathogenesis of FOP (e.g., in incorrect development of IVDs) (Schaffer et al., Spine 2005 30 (12): 1379-1385).

Bone Morphogenetic Proteins

BMPs are low-molecular weight glycoproteins that control many developmental processes. BMPs are multi-functional growth factors that belong to a larger family of related secreted factors, the transforming growth factor (TGF)-β superfamily. To date, around 20 BMP family members have been identified and characterized. Members of the BMP family include, for example, BMP-2, BMP-4, BMP-5, BMP-6, the osteogenic proteins OP-1 (BMP-7) and OP-2 (BMP-8), osteogenin (BMP-3), and BMP-9 to BMP-12. Other names for BMPs include growth and differentiation factors (GDF) and cartilage-derived morphogenetic proteins, e.g., CDMP-1 and -2, also known as GDF-5 and GDF-6/GDF-6, respectively. Notwithstanding that BMPs were first identified by virtue of their ability to promote ectopic cartilage and bone formation, BMP signaling plays a critical role in heart, limb, kidney, and skeletal development, and control many key steps in the formation and differentiation of the vertebrate nervous system.

BMPs signal through a molecular pathway, which is initiated by contact of extracellular BMPs with a high-affinity complex of heteromeric type II and type I serine/threonine kinase receptors. The receptor complexes in turn phosphorylate receptor regulated R-Smads 1, 5 and 8 which induces them to bind Smad4 (Co-Smad) and accumulate in the nucleus where they regulate transcription. The heteromeric BMP-regulated Smad complex can bind directly, or through other transcriptional partners to BMP response elements of gene promoters of xVent2, xVent2B, Msx1, Msx2, Hex, Smad7, and Id1. The pathway is further controlled by the action of inhibitory Smads 6 and 7 and by soluble antagonists that bind extracellular BMPs inhibiting binding to heteromeric complexes such as, Noggin, Chordin and Dan.

The manner in which BMPs regulate such diverse processes is largely determined by the cellular and tissue context in which the BMP signals are received. For example, although the molecular components of BMP signaling may be highly conserved, tissue and cell-type specificity ultimately determine which BMP and combinations of receptors, intracellular mediators, and extracellular antagonists control a particular process. BMP-regulated gene expression is further controlled by interaction of Smads with tissue-specific transcription factors and cross-talk with other signalling pathways to mediate the diverse transcriptional programs associated with BMP regulated processes.

Notwithstanding our increased understanding of the molecular events involved in development of an IVD, this understanding has yet to lead to the development of an effective treatment for a spinal disorder and/or spinal pain. Rather current treatment options for a spinal disorder and/or spinal pain require surgical intervention to replace a degenerated IVD and/or remove the IVD and fuse vertebrae. In this respect, spinal fusion is expensive because it requires prolonged hospitalisation and specialist surgical expertise. Furthermore, studies suggest that in the long-term, spinal fusion actually promotes degeneration at sites adjacent to the lumbar fusion. Furthermore, replacement of the disc is a major operation and despite potential benefits, many sufferers of repeated chronic neck pain and/or back pain avoid major spinal reconstruction. It is clear from the foregoing that there remains a need for compositions and methods for the treatment of spinal disorders and/or spinal pain, e.g. a spinal disorder associated with IVD degeneration, that does not require a prolonged period of hospitalization and/or that does not aggravate the spinal disorder and/or spinal pain. Ideally, this treatment should have the potential of regenerating disc tissue and/or preventing or slowing spinal degeneration.

SUMMARY OF INVENTION

In work leading up to the present invention, the inventors sought to identify biochemical pathway(s) that is(are) involved in the development of and/or causative of Klippel Feil Syndrome (KFS). The inventors reasoned that, because subjects suffering from KFS do not form one or more IVD(s), modulation of biochemical pathway(s) involved in pathogenesis of this disease is(are) likely to be useful for the treatment of disorders associated with ND degeneration. By mutational analysis of a panel of subjects suffering from KFS a number of alleles of the gene encoding growth differentiation factor 6 (GDF-6) (also known as bone morphogenetic protein-13 (BMP-13) or cartilage-derived morphogenic protein-2 (CDMP-2)) associated with development of KFS were identified. Using KFS as a model of abnormal ND development and/or maintenance, in vivo evidence that GDF-6 signaling is involved in IVD development and/or maintenance has been provided (Tassabeji et al., *Human Mutation*, Accepted 6 Feb. 2008).

The inventors then demonstrated that recombinant GDF-6 reduced, delayed or prevented IVD degeneration and/or enhanced IVD regeneration in an accepted animal model of ND degeneration, i.e., a sheep annular tear model of ND degeneration.

Recombinant GDF-6 was also shown by the inventors to induce production of extracellular matrix proteins in cells of an IVD, e.g., collagen type-1 and collagen type-2 and of a transcription factor involved in extracellular matrix synthesis, i.e., SOX-9. These results indicate that GDF-6 induces biological changes within ND cells associated with IVD regeneration.

The inventors extended these studies by modulating the level of proteins involved in GDF-6 signaling, e.g., a transcription factor, such as MSX-1 and/or MSX-2, in primary cells isolated from an IVD. As exemplified herein, overexpression of MSX-1 and/or MSX-2 in a cell isolated from an IVD, e.g., an annulus fibrosus cell or a nucleus pulposus cell, results in increased collagen production and increased extra-cellular matrix production by the cell. Both increased collagen production and increased extra-cellular matrix production by cells of the IVD are associated with IVD regeneration. Accordingly, a composition that modulates GDF-6 signaling is an attractive therapeutic for treating a spinal disorder and/or spinal pain, e.g., a spinal disorder and/or spinal pain associated with IVD degeneration.

In this respect, as discussed herein, the present inventors have demonstrated that modulation of various components of a GDF-6 signaling pathway in an IVD or a cell or tissue thereof is useful for treating a spinal disorder and/or spinal pain. Without limiting the invention in any manner, such modulation may comprise increasing the level and/or activity of GDF-6 in an IVD or a cell or tissue thereof and/or increasing the level and/or activity of MSX-1 in an IVD or a cell or tissue thereof and/or increasing the level and/or activity of MSX-2 in an IVD or a cell or tissue thereof. However, the present invention also encompasses the modulation of any component of GDF-6 signaling in an IVD or a cell or tissue thereof. In this respect, GDF-6 binds to a dimeric receptor comprising BMP receptor (BMPR)-1A (also known as ALK3) and/or a BMPR-1B (also known as ALK-6) and/or a BMPR-II. Following binding of GDF-6 to the receptor, the activated receptor phosphorylates a receptor-mediated Smad, e.g., Smad-1 and/or Smad-5 and/or Smad-8, which then forms a complex with Smad-4. The complex comprising a receptor-mediated Smad and Smad-4 then translocates to the nucleus and activates expression of a GDF-6-regulated gene, such as, for example, MSX-1 and/or MSX-2.

Accordingly, a "modulator of GDF-6 signaling" is to be understood to mean a compound that modulates any component of a GDF-6 signal transduction pathway in an IVD or a cell or tissue thereof, e.g., as described in the previous paragraph, including GDF-6 itself and/or a GDF-6 regulated gene, e.g., MSX-1 or MSX-1. This term also encompasses a compound that modulates, for example, activation of BMPR-1A and/or BMPR-IB and/or BMPR-II and/or Smad-1 and/or Smad-5 and/or Smad-8 and/or Smad-4. Similarly, the term "modulating GDF-6 signaling" shall be taken to mean modulating any component of a GDF-6 signal transduction pathway in an IVD or a cell or tissue thereof, e.g., GDF-6 and/or MSX-1 and/or MSX-2 and/or BMPR-1A and/or BMPR-IB and/or BMPR-II and/or Smad-1 and/or Smad-5 and/or Smad-8 and/or Smad-4.

As used herein, the term "modulator" shall be taken to mean a compound that enhances or reduces the activity or amount of GDF-6 signaling in an IVD or a cell or tissue thereof. In one example, the modulator enhances GDF-6 signaling in an IVD or a cell or tissue thereof.

The inventors have also produced methods and devices for administering a modulator of GDF-6 signaling to an IVD in such a manner that it is applied to a plurality of sites within the IVD and/or within a nucleus pulposus and/or within a region of the IVD defined by an annulus fibrosus and/or adjacent to at least a portion of a nucleus puplosus. In this respect, the viscous nature of the IVD, e.g., the nucleus pulposus means that a composition of matter administered by a single bolus injection may not disperse or may not be distributed within the IVD or nucleus pulposus and, as a consequence, may not exert sufficient biological effect to provide a therapeutic benefit. By administering a modulator of GDF-6 signaling, the inventors facilitate dispersion or distribution of the modulator within the IVD, preferably within the nucleus pulposus thereby enhancing the therapeutic benefit provided by the modulator.

SPECIFIC EMBODIMENTS

The scope of the invention will be apparent from the claims as filed with the application that follow the examples. The claims as filed with the application are hereby incorporated into the description. The scope of the invention will also be apparent from the following description of specific embodiments and/or detailed description of preferred embodiments.

In one example, the present invention provides a composition comprising (i) an amount of a modulator of GDF-6 signaling in an IVD or a cell or tissue thereof sufficient to reduce, delay or prevent IVD degeneration in a subject and/or to induce and/or enhance IVD regeneration in a subject and a suitable carrier or excipient. In one example, a modulator of GDF-6 signaling is a peptide or polypeptide. For example, a modulator of GDF-6 signaling is a peptide or polypeptide that mediates GDF-6 signaling in an IVD or a cell or tissue thereof, e.g., GDF-6 and/or MSX-1 and/or MSX-2 and/or BMPR-1A and/or BMPR-IB and/or BMPR-II and/or Smad-1 and/or Smad-5 and/or Smad-8 and/or Smad-4. For example, a modulator of GDF-6 signaling is a GDF-6 polypeptide or an active fragment thereof or an analog thereof or a derivative thereof or nucleic acid encoding same. Exemplary active fragments of GDF-6 include, for example, an isolated peptide having GDF-6 signaling activity, said peptide comprising a sequence of a fragment of a GDF-6 polypeptide, wherein said peptide does not comprise the sequence of set forth in SEQ ID NO: 2 or 3. In one example, the active fragment comprises a sequence from GDF-6 said sequence consisting essentially of or consisting of a sequence set forth in SEQ ID NO: 24 or 25. The present invention also provides analogs and/or derivatives of such an active fragment, e.g., a retro-analog comprising a sequence set forth in SEQ ID NO: 34 or 35, or a retro-inverted analog comprising a sequence set forth in SEQ ID NO: 36 or 37.

In another example, a modulator of GDF-6 signaling is a MSX-1 polypeptide or an active fragment thereof or an analog thereof or a derivative thereof or nucleic acid encoding same. In another example, a modulator of GDF-6 signaling is a MSX-2 polypeptide or an active fragment thereof or an analog thereof or a derivative thereof or nucleic acid encoding same. In one example, a composition as described herein according to any embodiment comprises a GDF-6 polypeptide or an active fragment thereof or an analog thereof or a derivative thereof and a MSX-1 polypeptide or an active fragment thereof or an analog thereof or a derivative thereof and a MSX-2 polypeptide or an active fragment thereof or an analog thereof or a derivative thereof.

In one example of the invention, a composition comprises a cell, e.g. a stem cell or a progenitor cell, e.g., a chondrogenic cell comprising and/or expressing a modulator of GDF-6 signaling in an IVD or a cell or tissue thereof. For example, the cell is transfected, transduced or transformed with a nucleic acid capable of expressing a peptide or polypeptide modulator of GDF-6 signaling in an IVD or cell or tissue thereof. In accordance with this example of the invention, a composition as described herein according to any embodiment comprises a sufficient number of cells (e.g., stem cells) comprising and/or expressing a modulator of GDF-6 signaling an IVD or a cell or tissue thereof sufficient to reduce, delay or prevent IVD degeneration in a subject and/or to induce and/or enhance IVD regeneration in a subject.

In one example, the cell additionally expresses a telomerase catalytic subunit, e.g., a telomerase reverse transcriptase encoded by a TERT gene. Such cells express increased levels of collagen. Suitable methods for producing cells expressing a telomerase catalytic subunit are described in the applicant's co-pending International Patent Application No. PCT/AU2006/00550.

The present invention also provides a composition for modulating GDF-6 signaling in an intervertebral disc or a cell or tissue thereof sufficient to reduce, delay or prevent intervertebral disc degeneration in a subject and/or to induce and/or enhance intervertebral disc regeneration in a subject, said composition comprising (i) an amount of a modulator of GDF-6 signaling; (ii) a suitable carrier or excipient; and (iii) instructions for administering the composition to an intevertebral disc of a subject. In one example the instructions are for administering the composition to a plurality of sites within an IVD and/or within a nucleus pulposus and/or to a plurality of sites within an inner wall of an annulus fibrosus, preferably to the plurality of sites in a single administration.

As used herein, the term "IVD degeneration" shall be taken to mean a process in which an amount of extracellular matrix and/or water is reduced in an IVD characterized by one or more of the following:
(i) a reduced height (i.e., the distance between the edges of the disc located between two vertebrae is reduced), e.g., relative to disc in a normal and/or healthy subject;
(ii) a reduced proteoglycan level in an IVD, e.g., relative to a proteoglycan level in an IVD in a normal and/or healthy subject;
(iii) a reduced water content, e.g., relative to a water content in an IVD in a normal and/or healthy subject;
(iv) a reduced level of Type II collagen and/or a Type IX collagen in an IVD, e.g., relative to the level of a Type II collagen and/or a Type IX collagen in an IVD normal and/or healthy individual;
(v) an enhanced level of a Type III collagen and/or a Type VI collagen in an IVD, e.g., relative to the level of a Type III collagen and/or a Type VI collagen in an IVD normal and/or healthy individual;
(vi) an increased number of apoptotic cells and/or fewer cells in an IVD, e.g., relative to the number of apoptotic cells or the number of cells in an IVD normal and/or healthy individual; and
(vii) structural failure of an IVD, such as, for example, a radial fissure, disc prolapse, endplate damage, internal collapse of the annulus or external collapse of the annulus. Notwithstanding that several of the characteristics discussed in the previous paragraph may be determined by comparing the level of a characteristic to the same characteristic in an IVD in a normal and/or healthy subject, such a direct comparison need not necessarily be performed. Rather, the level of the characteristic may be compared to, for example, a data set containing information pertaining to that characteristic derived from a population of normal and/or healthy individuals.

As used herein, the term "IVD regeneration" shall be taken to mean that one or more characteristics of IVD degeneration (e.g., as described supra) is partially or completely reversed. For example, following treatment with a modulator of GDF-6 signaling one or more of the characteristic described herein above is the same or similar level to that in an IVD in a normal and/or healthy individual.

An "amount of a modulator of GDF-6 signaling in an IVD or a cell or tissue thereof sufficient to reduce, delay or prevent IVD degeneration in a subject" will be understood by the skilled artisan to mean that the composition comprises a sufficient quantity of a modulator (and/or of cells expressing or comprising such a modulator) to reduce IVD degeneration and/or to prevent or delay or inhibit IVD degeneration. The skilled artisan will be aware that such an amount will vary depending on the modulator used, e.g., as a result of variation in the bioactivity of a modulator, and/or the severity of the disc degeneration and/or the cause of the disc degeneration. Accordingly, this term is not to be construed to limit the invention to a specific quantity, e.g., weight of a modulator and/or any specific number of cells expressing and/or comprising a modulator, rather the present invention encompasses any amount of the modulator sufficient to accomplish the stated purpose. Methods for determining the level of disc degeneration, e.g., by detecting one or more of the characteristics described supra, will be apparent to the skilled artisan and/or described herein.

Similarly, an "amount of a modulator of GDF-6 signaling in an IVD or a cell or tissue thereof sufficient to induce and/or enhance IVD regeneration in a subject" will be understood by the skilled artisan to vary depending on the modulator used, e.g., as a result of variation in the bioactivity of a modulator, and/or the severity of the IVD degeneration and/or the cause of the IVD degeneration. Accordingly, this term is also not to be construed to limit the invention to a specific quantity, e.g., weight of a modulator and/or any specific number of cells expressing and/or comprising a modulator, rather the present invention encompasses any amount of the modulator sufficient to induce and/or enhance IVD regeneration in a subject. Methods for detecting IVD regeneration in a subject will be apparent to the skilled artisan and/or described herein.

As used herein, the term "suitable carrier or excipient" shall be taken to mean a compound or mixture thereof that is suitable for administration to a subject for the treatment of a spinal disorder and/or spinal pain, albeit not necessarily limited in use to that context.

In one example, a suitable carrier or excipient is a "carrier or excipient for in situ administration". In this respect, a "carrier or excipient for in situ administration" shall be taken to mean a compound or mixture thereof that is suitable for administration to an IVD or a region surrounding an IVD in a subject.

In another example, a suitable carrier or excipient is an intraspinal carrier or excipient. As used herein, the term "intraspinal carrier or excipient" shall be taken to mean a compound or mixture thereof that is described in the art only with reference to administration into a spine.

In a still further example, a suitable carrier or excipient is an intra-IVD carrier or excipient. The term "intra-IVD carrier or excipient" shall be taken to mean a compound or mixture thereof that is suitable for application into an IVD, and which may be suitable for use in other contexts.

Preferred carriers or excipients are suitable for administration by injection into an IVD or alternatively, by direct application to an IVD.

A carrier and excipient useful in a composition described herein according to any embodiment will generally not inhibit to any significant degree a relevant biological activity of the active compound e.g., the carrier or excipient will not significantly inhibit the activity of the active compound with respect to modulation of GDF-6 signaling and/or IVD degeneration and/or IVD regeneration. For example, the carrier or excipient provides a buffering activity to maintain the compound at a suitable pH to thereby exert its biological activity.

In another example, a carrier or excipient in a composition comprising a GDF-6 polypeptide or active fragment or analog or derivative thereof permits the GDF-6 polypeptide, active fragment, analog or derivative to form a dimer and/or to remain in a dimeric state, i.e., the carrier or excipient is non-reducing.

Alternatively, or in addition, a suitable carrier or excipient permits a cell, e.g., a stem cell, to survive and/or grow. In one example, a suitable carrier or excipient promotes or enhances growth of a cell, e.g., a stem cell.

In one example, the composition has a viscosity that permits it to disperse or distribute evenly throughout the nucleus pulposus of a subject.

Alternatively, or in addition, the carrier or excipient comprises a compound that enhances cellular uptake of a modulator of GDF-6 signaling. For example, a carrier or excipient comprises a liposome to facilitate cellular uptake. In another example, a carrier or excipient for a nucleic acid modulator of GDF-6 signaling comprises a lipid-based delivery agent, e.g., 2,3-dioleyloxy-N-[2(sperminecarboxyamido)ethyl]-N,N-dimethyl-1-propanaminium trifluoroacetate, which is sold commercially as Lipofectamine 2000 (Invitrogen). Other lipid-based delivery agents will be apparent to the skilled artisan and/or described herein.

Alternatively, or in addition, the carrier or excipient comprises a compound that enhances the activity of modulator of GDF-6 signaling and/or reduces inhibition of a modulator of GDF-6 signaling, e.g., a protease inhibitor and/or a DNase inhibitor and/or a RNase inhibitor to thereby enhance the stability of the modulator.

Additional suitable carriers include, for example, collagen type I or collagen type II, e.g., of cervical or lumbar origin, recombinant elastin, hyaluronic acid, a polysaccharide, a chitin derivative, polyurethane foam, poly-lactic acid (PLA) polymer), poly-glycolic acid (PGA, PLGA) amongst others.

A preferred carrier or excipient is liquid at room temperature, e.g., at about 23° C., and becomes more viscous at body temperature, e.g., at about 37° C. The liquid nature of such a carrier or excipient facilitates administration of a composition as described herein according to any embodiment to or within an IVD and/or to or within a nucleus pulposus and/or to or within a region of an IVD defined by an annulus fibrosus.

Following administration, the carrier or excipient becomes more viscous thereby retaining the modulator of GDF-6 signaling at a site within a subject for a time and under conditions sufficient for the modulator to exert a beneficial effect, e.g., to modulate GDF-6 signaling and to reduce, prevent or delay IVD degeneration and/or to enhance or induce IVD regeneration. Preferably, the carrier or excipient has a stiffness of from about 1 Mpa to about 2 Mpa at about 37° C., e.g., to provide support to an IVD.

In one example, the composition is a slow release composition.

In one preferred example, a composition as described herein according to any embodiment comprises an amount of a modulator of GDF-6 signaling sufficient to induce or enhance collagen synthesis in an IVD cell, e.g., an annulus fibrosus cell and/or a nucleus pulposus cell and/or to enhance collagen in an IVD. Preferably, the composition comprises an amount of a modulator of GDF-6 to enhance synthesis of collagen-1 or collagen-2 in an IVD cell, e.g., an annulus fibrosus cell and/or a nucleus pulposus cell and/or to enhance collagen-1 and/or collagen-2 in an IVD.

In another example, a composition as described herein according to any embodiment comprises an amount of a modulator of GDF-6 signaling sufficient to induce or enhance expression of SOX9 an IVD cell, e.g., an annulus fibrosus cell and/or a nucleus pulposus cell.

In one example, the composition additionally comprises a radio-opaque composition, such as, for example, 5-(acetyl-(2,3-dihydroxypropyl)amino)-N,N'-bis(2,3-dihydroxypropyl)-2,4,6-triiodo-benzene-1,3-dicarboxamide (e.g., Omnipaque®), 3,5-diacetamido-2,4,6-triiodobenzoate, $BaSO_4$, or a composition as described in U.S. Pat. No. 6,635,064. Such a radio-opaque composition permits detection of the composition, e.g., to determine the distribution of the composition within an IVD, e.g., within or adjacent to at least a portion of a nucleus pulposus.

In another example, the composition of the present invention comprises an additional composition of matter having synergistic activity with respect to the active modulator of GDF-6 signaling in so far as inhibiting or preventing or delaying IVD degeneration and/or enhancing or inducing IVD degeneration is concerned e.g., a stem cell.

Alternatively, or in addition a composition as described herein according to any embodiment comprises an additional compound, such as, for example, morphogenetic protein to enhance regeneration of an IVD and/or prevent or reduce or delay IVD degeneration. Alternatively, or in addition, a composition as described herein according to any embodiment additionally comprises a mitogen, such as, for example, insulin-like growth factor-1 (IGF-1) and/or epidermal growth factor (EGF) and/or fibroblast growth factor (FGF). Alternatively, or in addition, a composition as described herein according to any embodiment additionally comprises an anti-catabolic compound, such as, for example, an inhibitor of a matrix-metalloproteinase, e.g., tissue inhibitor of matrix metalloproteinase-1 (TIMP-1). Suitable additional compounds will be apparent to the skilled artisan based on the description herein.

In a further example, a composition as described herein according to any embodiment additionally comprises an analgesic and/or an anti-inflammatory composition.

The skilled artisan will be aware that a composition as described herein according to any embodiment may be in a variety of forms, such as, for example, a liquid or a gel or a matrix or a lyophilized composition.

In one preferred example of the invention, the present invention provides a composition comprising an amount of a GDF-6 polypeptide and/or an active fragment thereof and/or an analog thereof and/or a derivative thereof and/or nucleic acid encoding same sufficient to reduce, delay or prevent IVD degeneration in a subject and/or to induce and/or enhance IVD regeneration in a subject and a suitable carrier or excipient. Preferably the composition is packaged with or comprises instructions for administering the composition to an intevertebral disc of a subject. In one example the instructions are for administering the composition to a plurality of sites and/or in a patterned manner within an IVD and/or within a nucleus pulposus and/or to a plurality of sites within an inner wall of an annulus fibrosus, preferably to the plurality of sites in a single administration.

In one preferred example of the invention, the present invention provides a composition comprising an amount of a an active fragment of a GDF-6 polypeptide consisting of or consisting essentially of a sequence set forth in SEQ ID NO: 24 or 25 sufficient to reduce, delay or prevent IVD degeneration in a subject and/or to induce and/or enhance IVD regeneration in a subject and a suitable carrier or excipient. Preferably the composition is packaged with or comprises instructions for administering the composition to an intevertebral disc of a subject. In one example the instructions are for administering the composition to a plurality of sites within an IVD and/or within a nucleus pulposus and/or to a plurality of sites within an inner wall of an annulus fibrosus, preferably to the plurality of sites in a single administration.

In another preferred example of the invention, a composition as described herein according to any embodiment comprises a sufficient number of stem cells comprising and/or expressing a GDF-6 polypeptide and/or an active fragment thereof and/or an analog thereof and/or derivative thereof sufficient to reduce, delay or prevent IVD degeneration in a subject and/or to induce and/or enhance ND regeneration in a subject and a suitable carrier or excipient. Preferably the composition is packaged with or comprises instructions for administering the composition to an intevertebral disc of a subject. In one example the instructions are for administering the composition to a plurality of sites within an IVD and/or within a nucleus pulposus and/or to a plurality of sites within an inner wall of an annulus fibrosus, preferably to the plurality of sites in a single administration.

In another preferred example of the invention, the present invention provides a composition comprising an amount of a MSX-1 polypeptide and/or an active fragment thereof and/or an analog thereof and/or a derivative thereof and/or nucleic acid encoding same sufficient to reduce, delay or prevent IVD degeneration in a subject and/or to induce and/or enhance IVD regeneration in a subject and a suitable carrier or excipient. Preferably the composition is packaged with or comprises instructions for administering the composition to an intevertebral disc of a subject. In one example the instructions are for administering the composition to a plurality of sites within an ND and/or within a nucleus pulposus and/or to a plurality of sites within an inner wall of an annulus fibrosus, preferably to the plurality of sites in a single administration.

In another preferred example of the invention, a composition as described herein according to any embodiment comprises a sufficient number of stem cells comprising and/or expressing a MSX-1 polypeptide and/or an active fragment thereof and/or an analog thereof sufficient to reduce, delay or prevent ND degeneration in a subject and/or to induce and/or enhance IVD regeneration in a subject and a suitable carrier or excipient. Preferably the composition is packaged with or comprises instructions for administering the composition to an intevertebral disc of a subject. In one example the instructions are for administering the composition to a plurality of sites within an IVD and/or within a nucleus pulposus and/or to a plurality of sites within an inner wall of an annulus fibrosus, preferably to the plurality of sites in a single administration.

In another preferred example of the invention, the present invention provides a composition comprising an amount of a MSX-2 polypeptide and/or an active fragment thereof and/or an analog thereof and/or a derivative thereof and/or nucleic acid encoding same sufficient to reduce, delay or prevent IVD degeneration in a subject and/or to induce and/or enhance IVD regeneration in a subject and a suitable carrier or excipient. Preferably the composition is packaged with or comprises instructions for administering the composition to an intevertebral disc of a subject. In one example the instructions are for administering the composition to a plurality of sites within an ND and/or within a nucleus pulposus and/or to a plurality of sites within an inner wall of an annulus fibrosus, preferably to the plurality of sites in a single administration.

In another preferred example of the invention, a composition as described herein according to any embodiment comprises a sufficient number of stem cells comprising and/or expressing a MSX-2 polypeptide and/or an active fragment thereof and/or an analog thereof sufficient to reduce, delay or prevent ND degeneration in a subject and/or to induce and/or enhance IVD regeneration in a subject and a suitable carrier or excipient. Preferably the composition is packaged with or comprises instructions for administering the composition to an intevertebral disc of a subject. In one example the instructions are for administering the composition to a plurality of sites within an ND and/or within a nucleus pulposus and/or to a plurality of sites within an inner wall of an annulus fibrosus, preferably to the plurality of sites in a single administration.

The present invention also provides a method for producing a composition described herein according to any embodiment. For example, such a method comprises mixing or otherwise combining an amount of a modulator of GDF-6 signaling in an IVD or a cell or tissue thereof sufficient to reduce, delay or prevent IVD degeneration in a subject and/or to induce and/or enhance IVD regeneration in a subject and a suitable carrier or excipient. In one example, the method additionally comprises producing or obtaining the modulator of GDF-6 signaling. For example, a peptide modulator or a polypeptide modulator or a nucleic acid modulator is produced synthetically or recombinantly, using a method known in the art and/or described herein. Alternatively, or in addition, a cell, e.g., a stem cell, is produced that expresses a polypeptide or peptide that modulates GDF-6 signaling, e.g., using recombinant means.

The present invention also provides a method for producing a composition for modulating GDF-6 signaling in an intervertebral disc or a cell or tissue thereof to thereby reduce, delay or prevent intervertebral disc degeneration in a subject and/or to induce and/or enhance intervertebral disc regeneration in a subject, said method comprising mixing or otherwise combining an amount of a modulator of GDF-6 signaling and a suitable carrier or excipient and providing instructions for administering the combination to an intevertebral disc of a subject.

In one example, the carrier or excipient has a viscosity that permits the composition to disperse or distribute evenly throughout the nucleus pulposus of a subject. Such carriers shall be taken to apply as a preferred embodiment to any embodiment described herein.

In another example, the carrier or excipient has a viscosity that permits the composition to disperse or distribute evenly throughout the annulus fibrosus of a subject. Such carriers shall be taken to apply as a preferred embodiment to any embodiment described herein.

The present invention also provides for use of an amount of a modulator of GDF-6 signaling sufficient to reduce, delay or prevent intervertebral disc degeneration in a subject and/or to induce and/or enhance intervertebral disc regeneration in a subject in the manufacture of a medicament for the treatment of a spinal disorder and/or spinal pain and/or intervertebral disc degeneration. Preferably, the modulator of GDF-6 signaling induces or enhances GDF-6 signaling in an intervertebral disc or a cell or tissue thereof.

In one example, the medicament comprises a suitable carrier or excipient having a viscosity that permits the medicament to disperse or distribute evenly throughout the nucleus pulposus of a subject.

The present invention also provides a medical device comprising an amount of a modulator of GDF-6 signaling in an IVD or a cell or tissue thereof sufficient to reduce, delay or prevent IVD degeneration in a subject and/or to induce and/or enhance IVD regeneration in a subject. For example, the medical device comprises a composition as described herein according to any embodiment. For example, the medical device is an IVD implant, e.g., an implant that supports that provides support to a degenerated IVD. Alternatively, or in addition, a suitable medical device is a stent that comprises a modulator of GDF-6 signaling and/or cell expressing or producing same that permits prolonged release of said modulator. Alternatively, a suitable medical device is a scaffold, e.g., a nanotube scaffold, for delivery of a modulator of GDF-6 signaling or a cell, e.g., a stem cell, expressing or comprising same. In a preferred embodiment, the device is a delivery device comprising a delivery conduit having a proximal end attachable to a source of the modulator of GDF-6 signaling or composition of the invention, an emitter structure at a distal end to the delivery conduit defining a plurality of spaced discharge apertures through which the modulator of GDF-6 signaling or composition is delivered to or within an IVD and/or to or within a nucleus pulposus and/or adjacent to at least a portion of a nucleus pulposus and/or to or within a region of an IVD defined by an annulus fibrosus. In a particularly preferred form, the device is a device as represented in any one of FIGS. 8 to 18.

As used herein, the term "adjacent to at least a region of a nucleus pulposus" includes application of the modulator or composition to a site in contact with a nucleus pulposus, i.e., adjoining a nucleus pulposus, and/or application of the modulator or composition at a site sufficiently close to the nucleus pulposus to exert a biological effect on a cell therein.

The present invention also provides a medical device for modulating GDF-6 signaling in an intervertebral disc or a cell or tissue thereof sufficient to reduce, delay or prevent intervertebral disc degeneration in a subject and/or to induce and/or enhance intervertebral disc regeneration in a subject, wherein the medical device comprises:
(i) an integer for administering an amount of a modulator of GDF-6 signaling or a composition comprising said modulator to an intervertebral disc of a subject; and
(ii) an amount of a modulator of GDF-6 signaling or an amount of the composition of the present invention; and
(iii) optionally, instructions for administering the modulator or composition to an intevertebral disc of a subject.

In one example, the medical device is an intervertebral disc implant or stent comprising the modulator or composition.

In another example, the integer for administering an amount of a modulator of GDF-6 signaling or a composition comprising said modulator to an intervertebral disc of a subject is adapted to administer the modulator or composition to a plurality of sites within the IVD and/or within a nucleus pulposus and/or adjacent to at least a portion of a nucleus pulposus and/or within a region of the IVD defined by an internal wall of the annulus fibrosus. Preferably, the integer is adapted to administer the modulator or composition to the plurality of sites in a single administration.

In a further example, the integer for administering an amount of a modulator of GDF-6 signaling or a composition comprising said modulator to an intervertebral disc of a subject comprises a delivery conduit having a proximal end attached to a source of the modulator of GDF-6 signaling or the composition and an emitter structure at a distal end of the delivery conduit, and wherein the emitter structure defines a plurality of spaced discharge apertures through which the modulator or composition is delivered.

In one example the instructions are for administering the composition to a plurality of sites and/or in a patterned manner within an IVD and/or within a nucleus pulposus and/or to a plurality of sites within an inner wall of an annulus fibrosus, preferably to the plurality of sites in a single administration.

The present invention also provides a method for preventing or delaying or treating a spinal disorder and/or spinal pain in a subject, said method comprising administering a modulator of GDF-6 signaling or composition comprising same, e.g., a composition as described herein according to any embodiment to a subject suffering from a spinal disorder and/or spinal pain for a time and under conditions sufficient to reduce, delay or prevent IVD degeneration in the subject and/or to induce and/or enhance IVD regeneration in the subject.

In one example, the present invention provides a method for preventing or delaying or treating a spinal disorder and/or spinal pain in a subject, said method comprising administering a cell, e.g., a stem cell, comprising or expressing a modulator of GDF-6 signaling or composition comprising same to a subject suffering from a spinal disorder and/or spinal pain for a time and under conditions sufficient to reduce, delay or prevent IVD degeneration in the subject and/or to induce and/or enhance IVD regeneration in the subject. For example, the cell is administered to or within an IVD and/or to or within a nucleus pulposus and/or adjacent to at least a portion of a nucleus pulposus and/or to or within a region of an IVD defined by an annulus fibrosus.

As used herein, the term "spinal disorder" shall be taken to mean an abnormality of the spine that is caused by IVD degeneration. Examples of spinal disorders include, for example, sciatica, a herniated disc, disc bulge, disc protrusion, disc extrusion, disc sequestration, an annulus tear, disc prolapse, endplate damage, a Schmorl node, internal disc disruption or spondylosis.

During IVD degeneration, a nerve within or adjacent to an IVD may be damaged. Such damage generally results in discomfort to a subject, or "spinal pain".

In one example of the present invention, the spinal disorder and/or spinal pain is a chronic spinal disorder and/or chronic spinal pain.

In one example, a modulator of GDF-6 signaling is a polypeptide or peptide or analog thereof or derivative thereof.

In a preferred example, the modulator is administered to an IVD and/or to a region of a subject surrounding or adjacent to an IVD. Preferably, the modulator of GDF-6 signaling or composition of the present invention is administered to or within a nucleus pulposus and/or adjacent to at least a portion of a nucleus pulposus and/or to or within a region of an IVD defined by an annulus fibrosus of an IVD.

Preferably, the modulator of GDF-6 signaling or composition of the present invention is administered to a plurality of sites within an IVD, preferably a plurality of sites within and/or adjacent to at least a portion of a nucleus pulposus and/or within a region of an IVD defined by an interior wall of an annulus fibrosus. Preferably, the modulator of GDF-6 signaling or composition of the present invention is administered to the plurality of sites in a single administration. Suitable methods and/or devices for administration to a plurality of sites will be apparent to the skilled artisan and/or described herein. Accordingly, this embodiment of the invention excludes a single bolus injection of a modulator of GDF-6 signaling or composition of the invention to a single site within an IVD.

As used herein, the term "interior wall of an annulus fibrosus" shall be taken to mean a boundary or surface of an annulus fibrosus adjacent to or adjoining a nucleus pulposus.

Notwithstanding that the modulator or composition is administered to a plurality of sites in a single administration, this does not mean that the modulator or composition is administered to a subject only once. Rather, the present invention encompasses multiple and/or repetitive administration of the composition or modulator, provided that the composition or modulator is administered to the plurality of sites in a single administration at least once.

In one example, a modulator of GDF-6 signaling or a composition of the present invention is administered in a patterned manner within an IVD, preferably within a nucleus pulposus and/or adjacent to at least a portion of a nucleus pulposus and/or within a region of an IVD defined by an annulus fibrosus. By "patterned manner" is meant that a modulator or composition is administered at sites within an IVD, preferably within a nucleus pulposus and/or adjacent to at least a portion of a nucleus pulposus and/or a region of an IVD defined by an annulus fibrosus, wherein the sites are spatially separated from one another. In one example, the modulator or composition is administered in a patterned manner in a single administration.

Preferably, the modulator of GDF-6 signaling or composition of the present invention is administered to a plurality of sites within an IVD or in a patterned manner within an IVD, preferably within a nucleus pulposus and/or adjacent to at least a portion of a nucleus pulposus and/or within a region of an IVD defined by an annulus fibrosus such that following a sufficient time the modulator or composition disperses or is distributed within or throughout an IVD, preferably within or throughout a nucleus puplosus. In this respect, the term "within an IVD or a nucleus puplosus" means that at least a portion of the administered modulator or composition is distributed within the IVD or nucleus pulposus, albeit not necessarily entirely throughout the IVD or nucleus pulposus. Preferably, the composition is distributed within at least about 50% or 60% or 70% or 80% or 90% of an IVD, more preferably, within at least about 50% or 60% or 70% or 80% or 90% of a nucleus pulposus. Preferably, the modulator or composition is distributed substantially uniformly or uniformly within or throughout an IVD, preferably throughout a nucleus pulposus.

In one example, the modulator or composition is administered to a plurality of sites or in a patterned manner so as to permit said modulator or composition to disperse or distribute evenly throughout the nucleus pulposus.

The skilled artisan will be aware of methods for determining the distribution or uniformity of distribution of a composition as described herein according to any embodiment. For example, the composition comprises a radio-opaque composition, and the distribution is determined by performing an X-ray or a MRI to detect the distribution of the radio-opaque composition, which is indicative of the distribution or uniformity of distribution of the composition of the present invention.

In one example, a method as described herein according to any embodiment comprises administering a modulator of GDF-6 signaling or a composition as described herein according to any embodiment for a time and under conditions to induce or enhance collagen synthesis in an IVD and/or to increase or enhance the level of collagen in an IVD, e.g., the level of collagen-1 and/or collagen-2 in an IVD.

In another example, a modulator of GDF-6 signaling or composition of the invention is administered by a process comprising administering a nucleic acid encoding a modulator of GDF-6 signaling to a subject under conditions sufficient for transcription and translation of said nucleic acid to occur. For example, the nucleic acid is administered to an IVD or cell or tissue thereof.

In a still further example, a modulator of GDF-6 signaling is administered by a process comprising administering a medical device comprising the modulator of GDF-6 signaling to a subject, e.g., to an IVD in a subject, e.g., a medical device described herein according to any embodiment. For example, the modulator or composition is administered via a medical device comprising a delivery conduit having a proximal end attachable to a source of the modulator of GDF-6 signaling or the composition and an emitter structure at a distal end of the delivery conduit, wherein the emitter structure defines a plurality of spaced discharge apertures through which the modulator or composition is delivered.

As will be apparent to the skilled artisan, the present invention also provides a method for preventing or delaying or treating IVD degeneration in a subject and/or a method for inducing or enhancing IVD regeneration in a subject. The method steps described supra shall be taken to apply mutatis mutandis to these embodiments of the invention.

The therapeutic method described herein is not to be limited to a single application of a GDF-6 signaling modulator or composition comprising same. The present invention also contemplates repeated administration of a GDF-6 signaling modulator or a composition as described herein according to any embodiment e.g., to extend the period over which beneficial effects are derived.

In another example, the therapeutic method of the invention additionally comprises providing or obtaining a composition as described herein according to any embodiment or information concerning same.

In another example, the present invention provides a method of treatment of a subject in need thereof, said method comprising:
(i) identifying a subject suffering from or developing a spinal disorder and/or spinal pain and/or IVD degeneration;
(ii) obtaining a modulator of GDF-6 signaling or a composition as described herein according to any embodiment; and
(iii) administering said modulator or composition to said subject, e.g., as described herein.

The present invention also provides a method of treatment of a subject in need thereof, said method comprising:
(i) identifying a subject suffering from or developing a spinal disorder and/or spinal pain and/or IVD degeneration; and
(ii) recommending administration of a modulator of GDF-6 signaling or a composition as described herein according to any embodiment.

Alternatively, the method of treatment comprises administering or recommending administration of a modulator of GDF-6 signaling or a composition as described herein according to any embodiment to a subject previously identified as suffering from a spinal disorder and/or spinal pain and/or IVD degeneration.

The present invention also provides for the use of an amount of a modulator of GDF-6 signaling sufficient to reduce, delay or prevent IVD degeneration in a subject and/or to induce and/or enhance IVD regeneration in a subject in the manufacture of a medicament for the treatment of a spinal disorder and/or spinal pain and/or IVD degeneration.

The present invention also provides a method for administering a modulator of GDF-6 signaling or composition comprising a modulator of GDF-6 signaling to a subject comprising:
   accessing a region of an IVD by surgical intervention or injection;
   providing or obtaining a medical device comprising the modulator or composition wherein the medical device comprises a delivery conduit having a proximal end attachable to a source of the modulator of GDF-6 signaling or the composition and an emitter structure at a distal end of the delivery conduit, wherein the emitter structure defines a plurality of spaced discharge apertures through which the modulator or composition is delivered;

inserting the emitter structure of the medical device at least partially into the accessed region of the IVD;

manipulating the emitter structure so that the emitter structure is positioned within the IVD and/or at least partially surrounds or is positioned within the nucleus pulposus and/or a region of the IVD defined by an internal wall of the annulus fibrosus;

discharging the modulator or composition through the apertures of the device so as to administer said modulator or composition to a plurality of sites within the ND in a single administration and/or at least partially surrounds or is positioned within the nucleus pulposus and/or a region of the ND defined by an internal wall of the annulus fibrosus, thereby administering the modulator or composition to the subject.

The present invention also provides a process for preventing or delaying or treating a spinal disorder and/or spinal pain in a subject, said method comprising administering a modulator of GDF-6 signaling or composition comprising a modulator of GDF-6 signaling to a subject suffering from a spinal disorder and/or spinal pain for a time and under conditions sufficient to reduce, delay or prevent intervertebral disc (ND) degeneration in the subject and/or to induce and/or enhance intervertebral disc regeneration in the subject, wherein said process comprises administering the modulator or composition to a subject in need thereof by performing the method described in the previous paragraph and resting the subject for a time and under conditions sufficient to reduce, delay or prevent intervertebral disc (IVD) degeneration and/or to induce and/or enhance intervertebral disc regeneration.

The present invention also provides a kit comprising:
(i) a composition for modulating GDF-6 signaling in an intervertebral disc or a cell or tissue thereof sufficient to reduce, delay or prevent intervertebral disc degeneration in a subject and/or to induce and/or enhance intervertebral disc regeneration in a subject, said composition comprising (a) an amount of a modulator of GDF-6 signaling; and (b) a suitable carrier or excipient; and
(ii) instructions for administering the composition to an intevertebral disc of a subject.

In one example, the composition in said kit comprises a stem cell comprising or expressing a modulator of GDF-6 signaling.

In another example, the composition in said kit comprises an amount of a modulator of GDF-6 signaling sufficient to enhance or induce collagen synthesis in an intervertebral disc or a cell or tissue thereof.

In a further example the composition in said kit is a slow release composition.

In a still further example, the composition in said kit has a viscosity that permits it to disperse or distribute evenly throughout the nucleus pulposus of a subject.

DEFINITIONS

This specification contains nucleotide and amino acid sequence information prepared using PatentIn Version 3.4, presented herein after the claims. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (e.g. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only.

Functionally-equivalent products, compositions and methods are clearly within the scope of the invention, as described herein.

BRIEF DESCRIPTION OF THE DRAWINGS

FIG. 1, Panel b is a copy of a photomicrograph showing staining of a section from an IVD of a rat for GDF-6 immunoreactivity. GDF-6 is detected in nucleus pulposus cells.

FIG. 1, Panel c is a copy of a photomicrograph showing staining of a section from an IVD of a human for GDF-6 immunoreactivity. GDF-6 is not detected in annular fibrosus cells.

FIG. 1, Panel d is a copy of a photomicrograph showing staining of a section from an IVD of a human for GDF-6 immunoreactivity. GDF-6 is detected in nucleus pulposus cells.

FIG. 10 shows a schematic, plan view of the device of FIG. 8.

FIG. 11 shows, on an enlarged scale, a distal part of the device encircled by circle 'A' in FIG. 10.

DETAILED DESCRIPTION OF THE PREFERRED EMBODIMENTS

1. Modulators of GDF-6 Signaling

Figure 1:
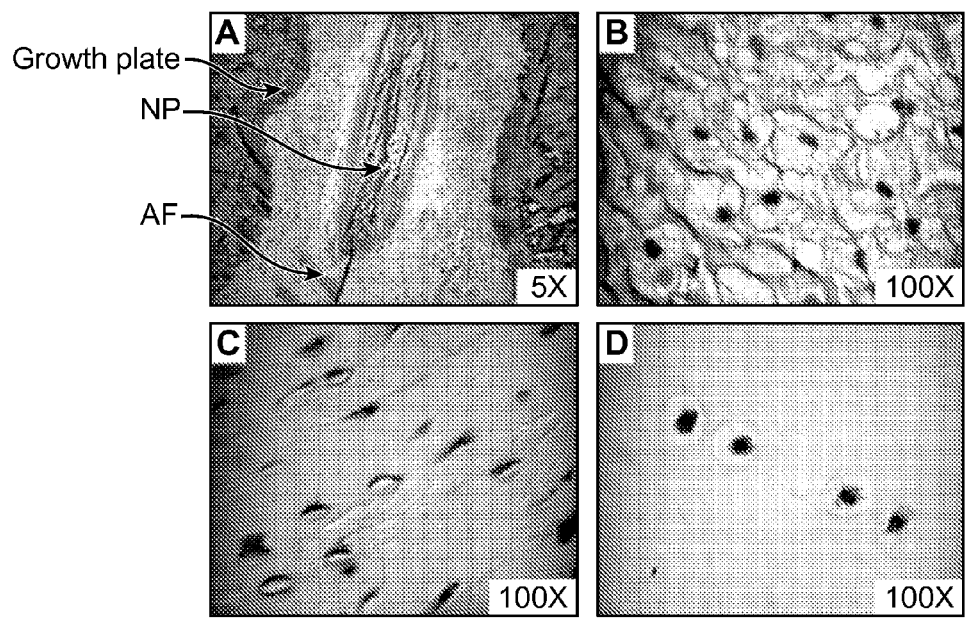
FIG. 1, Panel a is a is a copy of a photomicrograph showing staining of a rat vertebral section from rat for GDF-6 immunoreactivity. GDF-6 is detected in nucleus pulposus cells of the rat and within the growth plate of the vertebrae.

A composition as described herein comprises any one or more modulators of GDF-6 signaling in an IVD or cell or tissue thereof in a subject. For example, a modulator enhances GDF-6 signaling in an IVD or cell or tissue thereof in a subject. Such a modulator is also referred to as a GDF-6 signaling enhancer or a GDF-6 signaling agonist.

The present invention contemplates any modulator of GDF-6 signaling. For example, the modulator is a peptide, a polypeptide, a nucleic acid, an antibody, an antibody fragment or a small molecule.

1.1 Polypeptide Modulators

In one example, a modulator of GDF-6 signaling in an IVD or cell or tissue thereof is a peptide or polypeptide. For example, a modulator is a peptide or polypeptide that mediates GDF-6 signaling in an IVD or cell or tissue thereof. For example, a modulator is a polypeptide individually or collectively selected from the group consisting of:
(i) a polypeptide selected from the group consisting of GDF-6, MSX-1, MSX-2, BMPR-1A, BMPR-IB, BMPR-II, Smad-1, Smad-5, Smad-8 and Smad-4;
(ii) an active fragment of (i);
(iii) an analog of (i) or (ii); and
(iv) a derivative of any one of (i) to (iii).

By "individually" is meant that the invention encompasses the recited polypeptides or groups of polypeptides separately, and that, notwithstanding that individual polypeptides or groups of polypeptides may not be separately listed herein the accompanying claims may define such polypeptides or groups of polypeptides separately and divisibly from each other.

By "collectively" is meant that the invention encompasses any number or combination of the recited polypeptides or groups of polypeptides, and that, notwithstanding that such numbers or combinations of polypeptides or groups of peptides may not be specifically listed herein the accompanying claims may define such combinations or sub-combinations separately and divisibly from any other combination of polypeptides or groups of polypeptides.

By "active fragment" is meant a portion of a polypeptide that retains the ability of that polypeptide to modulate GDF-6 signaling. An active fragment may have the same level of activity as the original protein or an enhanced or reduced level of activity compared to the level of activity of the original protein. Methods for determining GDF-6 activity will be apparent to the skilled artisan and/or described herein.

In one preferred example of the invention, the modulator of GDF-6 signaling in an IVD or cell or tissue thereof is a GDF-6 polypeptide or an active fragment thereof. As used herein, the term "GDF-6" shall be taken to mean a polypeptide comprising an amino acid sequence at least about 80% identical to the sequence set forth in SEQ ID NO: 2 or 3 or encoded by a nucleic acid comprising the sequence set forth in SEQ ID NO: 1, wherein said polypeptide is capable of modulating GDF-6 signaling in an ND or cell or tissue thereof. Such a GDF-6 polypeptide is useful because it binds to a transmembrane receptor and enhances GDF-6 signaling in an IVD or cell or tissue thereof. Accordingly, it is not necessary for the polypeptide to enter a cell to induce GDF-6 signaling.

Preferably, the polypeptide has at least about 90% identity or 95% identity or 98% identity or 99% identity to the sequence set forth in SEQ ID NO: 2 or 3 or encoded by a nucleic acid comprising the sequence set forth in SEQ ID NO: 1, wherein said polypeptide is capable of modulating GDF-6 signaling in an IVD or cell or tissue thereof.

In determining whether or not two sequences fall within these defined percentage identity limits, those skilled in the art will be aware that it is possible to conduct a side-by-side comparison of the sequences. In such comparisons or alignments, differences will arise in the positioning of non-identical residues depending upon the algorithm used to perform the alignment. In the present context, references to percentage identities and similarities between two or more sequences shall be taken to refer to the number of identical and similar residues respectively, between said sequences as determined using any standard algorithm known to those skilled in the art. For example, nucleotide identities and similarities are calculated using software of the Computer Genetics Group, Inc., University Research Park, Maddison, Wis., United States of America, e.g., using the GAP program of Devereaux et al., *Nucl. Acids Res.* 12, 387-395, 1984, which utilizes the algorithm of Needleman and Wunsch, *J. Mol. Biol.* 48, 443-453, 1970. Alternatively, the CLUSTAL W algorithm of Thompson et al., *Nucl. Acids Res.* 22, 4673-4680, 1994, is used to obtain an alignment of multiple sequences, wherein it is necessary or desirable to maximize the number of identical/similar residues and to minimize the number and/or length of sequence gaps in the alignment. Sequence alignments can also be performed using a variety of other commercially available sequence analysis programs, such as, for example, the BLAST program available at NCBI.

In a preferred example, an active fragment of GDF-6 is an isolated peptide having GDF-6 signaling activity or an analog or derivative thereof, wherein said peptide consists of the sequence of a C-terminal fragment of a GDF-6 polypeptide or an analog or derivative thereof and optionally comprises an N-terminal methionine residue. In one example, the peptide, analog or derivative does not comprise all of the pro-region of a GDF-6 polypeptide. In another example, the peptide, analog or derivative consists of about 120 amino acids derived from the C-terminus of native GDF-6. In a further example, the peptide, analog or derivative comprises sufficient cysteine residues to form homodimers and/or heterodimers under non-reducing conditions. For example, the peptide comprises a sequence set forth in any one of SEQ ID NOs: 24 or 25 or a sequence having at least about 90% identity to any one of SEQ ID NOs: SEQ ID NO: 24 or 25. In this respect, the sequence set forth in SEQ ID NO: 25 is that of an active fragment of GDF-6 fused at its carboxy-terminus to a FLAG epitope and a TEV protease cleavage site. In one example, the peptide comprises an N-terminal methionine residue.

In another example, the peptide having GDF-6 signaling activity or an analog or derivative thereof is a retro-peptide analog, e.g., comprising a sequence set forth in SEQ ID NO: 34 or 35.

In another example, the isolated peptide having GDF-6 signaling activity or an analog or derivative thereof comprises one or more D-amino acids.

In a further example, the isolated peptide having GDF-6 signaling activity or an analog or derivative thereof is a retro-inverted analog, e.g., comprising a sequence set forth in SEQ ID NO: 36 or 37.

As used herein, the term "consisting essentially of" shall be taken to mean that the active fragment comprises the recited sequence and any other unstated features that do not materially affect the GDF-6 signaling modulatory properties of the active fragment.

The term "consisting of" means that the active fragment only has the recited sequence.

In one example, a GDF-6 polypeptide or active fragment thereof or analog or derivative thereof comprises a pair of subunits disulfide bonded to produce a dimer. In this respect, the dimer can contain two GDF-6 polypeptides or two active fragments or two analogs or two derivatives, or mixtures of a GDF-6 polypeptide and/or active fragment and/or analog and/or derivative. For example, the dimer comprises a GDF-6 polypeptide and an active fragment or a GDF-6 polypeptide and an analog and/or an active fragment and an analog or a GDF-6 polypeptide and a derivative or an active fragment and a derivative or an analog and a derivative.

In another example, the polypeptide is a MSX-1 polypeptide or an active fragment thereof. As used herein, the term "MSX-1" shall be taken to mean a polypeptide comprising an amino acid sequence at least about 80% identical to the sequence set forth in SEQ ID NO: 5 or encoded by a nucleic acid comprising the sequence set forth in SEQ ID NO: 4, wherein said polypeptide is capable of modulating GDF-6 signaling in an IVD or cell or tissue thereof.

Preferably, the polypeptide has at least about 90% identity or 95% identity or 98% identity or 99% identity to the sequence set forth in SEQ ID NO: 5 or encoded by a nucleic acid comprising the sequence set forth in SEQ ID NO: 4, wherein said polypeptide is capable of modulating GDF-6 signaling in an IVD or cell or tissue thereof.

In one example, a MSX1 polypeptide or active fragment thereof or analog or derivative thereof comprises a pair of MSX1 subunits bound to one another to produce a dimer. In this respect, the dimer can contain two MSX1 polypeptides or two active fragments or two analogs or two derivatives, or mixtures of a MSX1 polypeptide and/or active fragment and/or analog and/or derivative. For example, the dimer comprises a MSX1 polypeptide and an active fragment or a MSX1 polypeptide and an analog and/or an active fragment and an analog or a MSX1 polypeptide and a derivative or an active fragment and a derivative or an analog and a derivative.

In another example, the MSX1 polypeptide or active fragment thereof or analog or derivative thereof is dimerized with a Dlx1 protein, e.g., as described in Zhang et al., *Mol. and Cell. Biol.* 17: 2920-2932, 1997.

In another example, the polypeptide is a MSX-2 polypeptide or an active fragment thereof. As used herein, the term "MSX-2" shall be taken to mean a polypeptide comprising an amino acid sequence at least about 80% identical to the sequence set forth in SEQ ID NO: 7 or encoded by a nucleic acid comprising the sequence set forth in SEQ ID NO: 6, wherein said polypeptide is capable of modulating GDF-6 signaling in an IVD or cell or tissue thereof.

Preferably, the polypeptide has at least about 90% identity or 95% identity or 98% identity or 99% identity to the sequence set forth in SEQ ID NO: 7 or encoded by a nucleic acid comprising the sequence set forth in SEQ ID NO: 6, wherein said polypeptide is capable of modulating GDF-6 signaling in an IVD or cell or tissue thereof.

The sequence of additional peptide or polypeptide modulators of GDF-6 signaling are readily derivable from publicly available databases, such as, for example, the Genbank database available from NCBI. Moreover, methods for determining a peptide or polypeptide having GDF-6 modulatory activity will be apparent to the skilled artisan, e.g., based on the description herein.

The present invention also clearly extends to variants of a GDF-6 modulatory peptide or polypeptide described herein, such as derivatives and/or analogs, by modification to the sequences provided herein. The invention also extends to homologs i.e., functionally-equivalent peptides or polypeptide having related sequences to the sequences provided herein.

It is understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which specific amino acids may be substituted or deleted. Particular embodiments encompass variants that have one, two, three, four, five or more variations in the amino acid sequence relative to a base peptide subject to the retention of an ability to modulate GDF-6 signaling and, preferably reduce or prevent or delay IVD degeneration and/or enhance or induce IVD regeneration. Of course, a plurality of variants may be made and used in accordance with the invention.

A modulator of GDF-6 signaling, e.g., a GDF-6 polypeptide or functional fragment thereof may also be glycosylated. Glycosylation is the modification of a protein by addition of one or more oligosaccharide groups. There are usually two types of glycosylation: O-linked oligosaccharides are attached to serine or threonine residues while N-linked oligosaccharides are attached to asparagine residues when they are part of the sequence Asn-X-Ser/Thr, where X can be any amino acid except proline. Glycosylation can dramatically affect the physical properties of proteins and can also be important in protein stability, secretion, half-life, and subcellular localization. In some embodiments, the modulator of GDF-6 signaling comprise N-linked oligosaccharaides. In other embodiments, the modulator of GDF-6 signaling comprise O-linked oligosaccharides. In yet other embodiments, the modulator of GDF-6 signaling of this inventions comprise both N-linked and O-linked oligosaccharides. In some embodiments, the glycosylation pattern of the modulator of GDF-6 signaling may be modified to control the carbohydrate composition of the glycoprotein.

Based on the definition of "modulator of GDF-6 signaling" herein above, the skilled artisan will be aware that a bone morphogenetic protein (BMP)-2, BMP-4, BMP-7 (syn. osteogenic protein (OP)-1) and/or BMP-14 is not a modulator of GDF-6 signaling.

Accordingly, the term "modulator of GDF-6 signaling" does not encompass BMP-2, BMP-4, BMP-7/OP-1 or BMP-14.

Peptide and Polypeptide Derivatives

As used herein the term "derivative" shall be taken to mean a peptide or polypeptide that is derived from a peptide or polypeptide modulator of GDF-6 signaling as described herein, e.g., a fragment or processed form of the peptide or polypeptide, or a molecule comprising one or more amino acid substitutions, or comprising additional amino acid residues or non-amino acid substituents, relative to the base peptide or polypeptide from which it is derived. The term "derivative" also encompasses fusion proteins comprising a peptide of the invention.

Exemplary fusion protein comprises a label, such as, for example, an epitope, e.g., a FLAG epitope or a V5 epitope or an HA epitope. Such a tag is useful for, for example, purifying the fusion protein. Preferably, the label is a FLAG epitope.

A "conservative amino acid substitution" is one in which an amino acid residue is replaced with another amino acid residue without disturbing the overall structure of the peptide. Such changes tend to rely on similarity in hydrophilicity and/or polarity of the substituent. The size and/or charge of the side chains also are relevant factors in determining which substitutions are conservative. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

Those skilled in the art are well aware that the following substitutions are permissible conservative substitutions (i) substitutions involving arginine, lysine and histidine; (ii) substitutions involving alanine, glycine and serine; and (iii) substitutions involving phenylalanine, tryptophan and tyrosine.

The importance of the hydropathic amino acid index in conferring interactive biological function on a protein is generally understood in the art (Kyte & Doolittle, *J. Mol. Biol.* 157, 105-132, 1982). It is known that certain amino acids may be substituted for other amino acids having a similar hydropathic index or score and still retain a similar biological activity. The hydropathic index of amino acids also may be considered in determining a conservative substitution that produces a functionally equivalent molecule. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within .+/−0.2 is preferred. More preferably, the substitution will involve amino acids having hydropathic indices within .+/−0.1, and more preferably within about +/−0.05.

Non-amino acid substituents may be linked covalently to a peptide e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound. For example, particular amino acid residues may be derivatized or chemically modified in order to enhance the stability of the peptide or to permit coupling of the peptide to other agents, particularly lipids.

Chemical moieties may be linked covalently to a peptide or polypeptide e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound.

An "amino terminal capping group" of a peptide or polypeptide described herein is any chemical compound or moiety that is covalently linked or conjugated to the amino terminal amino acid residue of a peptide compound. An amino terminal capping group may be useful to inhibit or prevent intramolecular cyclization or intermolecular polymerization, to protect the amino terminus from an undesirable reaction with other molecules, to provide additional antioxidative activity, or to provide a combination of these properties. A peptide or polypeptide that possesses an amino terminal capping group may possess other beneficial activities as compared with the uncapped peptide, such as enhanced efficacy or reduced side effects. Examples of amino terminal capping groups that are useful in preparing a peptide or polypeptide include, but are not limited to, 1 to 6 naturally occurring L-amino acid residues, preferably, 1-6 lysine residues, 1-6 arginine residues, or a combination of lysine and arginine residues; urethanes; urea compounds; lipoic acid ("Lip"); glucose-3-O-glycolic acid moiety ("Gga"); or an acyl group that is covalently linked to the amino terminal amino acid residue of a peptide, wherein such acyl groups useful in the compositions of the invention may have a carbonyl group and a hydrocarbon chain that ranges from one carbon atom (e.g., as in an acetyl moiety) to up to 25 carbons (e.g., palmitoyl group, "Palm" (16:0) and docosahexaenoyl group, "DHA" (C22:6-3)). Furthermore, the carbon chain of the acyl group may be saturated, as in Palm, or unsaturated, as in DHA. It is understood that when an acid, such as docosahexaenoic acid, palmitic acid, or lipoic acid is designated as an amino terminal capping group, the resultant peptide compound is the condensed product of the uncapped peptide and the acid.

A "carboxy terminal capping group" of a peptide or polypeptide is any chemical compound or moiety that is covalently linked or conjugated to the carboxy terminal amino acid residue of the peptide or polypeptide. A peptide or polypeptide possessing a carboxy terminal capping group may also possess other beneficial activities as compared with the uncapped peptide, such as enhanced efficacy, reduced side effects, enhanced hydrophilicity, enhanced hydrophobicity. Carboxy terminal capping groups that are particularly useful include primary or secondary amines that are linked by an amide bond to the α-carboxyl group of the carboxy terminal amino acid of the peptide or polypeptide. Other carboxy-terminal capping groups useful in the invention include aliphatic primary and secondary alcohols and aromatic phenolic derivatives, including flavenoids, with 1 to 26 carbon atoms, which form esters when linked to the carboxylic acid group of the carboxy terminal amino acid residue of a peptide or polypeptide described herein.

Other chemical modifications of a peptide or polypeptide, include, for example, glycosylation, acetylation (including N-terminal acetylation), carboxylation, carbonylation, phosphorylation, PEGylation, amidation, addition of trans olefin, substitution of α-hydrogens with methyl groups, derivatization by known protecting/blocking groups, circularization, inhibition of proteolytic cleavage (e.g., using D amino acids), linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, etc.

Peptide Analogs

In another example of the invention, a peptide or polypeptide analog having GDF-6 signaling modulatory activity is prepared. As used herein, the term "analog" shall be taken to mean a peptide or polypeptide that is modified to comprise one or more non-naturally-occurring amino acids.

Analogs may also comprise sterically similar compounds that mimic critical subdomains of a peptide or polypeptide. Such "peptidomimetics" are produced by modeling and chemical design processes known to those of skill in the art.

Preferred analogs of a GDF-6 signaling modulatory peptides or polypeptides comprise one or more non-naturally occurring amino acids or amino acid analogs. For example, a peptide or polypeptide modulator comprises one or more naturally occurring non-genetically encoded L-amino acids, synthetic L-amino acids or D-enantiomers of an amino acid. For example, the peptide comprises only D-amino acids. For example, the analog comprises one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine 4-chlorophenylalanine, 2-fluorophenylalanine, 3-fluorophenylalanine, 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, ρ-aminophenylalanine, N-methylvaline, homocysteine, homoserine, ε-amino hexanoic acid, δ-amino valeric acid, 2,3-diaminobutyric acid and mixtures thereof.

Other amino acid residues that are useful for making the peptides or polypeptides or analogs thereof can be found, e.g., in Fasman, 1989, CRC Practical Handbook of Biochemistry and Molecular Biology, CRC Press, Inc., and the references cited therein.

The present invention additionally encompasses an isostere of a peptide or polypeptide described herein. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[$CH_2S$], ψ[$CH_2NH$], ψ[$CSNH_2$], ψ[NHCO], ψ[$COCH_2$], and ψ[(E) or (Z) CH=CH]. In the nomenclature used above, ψ indicates the absence of an amide bond. The structure that replaces the amide group is specified within the brackets.

Other modifications include, for example, an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In another example, a peptide analog is a retro peptide or polypeptide (see, for example, Goodman et al., *Accounts of Chemical Research*, 12:1-7, 1979). A retro peptide or polypeptide comprises a reversed amino acid sequence of a peptide modulator described herein. For example, the retro-peptide comprises a sequence set forth in SEQ ID NO: 34 or 35.

In a further example, an analog of a peptide described herein is a retro-inverso peptide or polypeptide (Sela and Zisman, *FASEB J.* 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverso peptide or polypeptide analogs are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., *Nature*, 368, 744-746 (1994); Brady et al., *Nature*, 368, 692-693 (1994). The net result of combining D-enantiomers and reverse synthesis is that the positions of carbonyl and amino groups in each amide bond are exchanged, while the position of the side-chain groups at each alpha carbon is preserved. An advantage of retro-inverso peptides is their enhanced activity in vivo due to improved resistance to proteolytic degradation, i.e., the peptide has enhanced stability. (e.g., Chorev et al., Trends Biotech. 13, 438-445, 1995).

Retro-inverso or retroinverso peptide or polypeptide analogs may be complete or partial. Complete retro-inverso peptides or polypeptides are those in which a complete sequence of a peptide described herein is reversed and the chirality of each amino acid other than glycine in a sequence is inverted. The exclusion of glycine is based on the fact that glycine does not have a chiral analog. Partial retro-inverso peptide or polypeptide analogs are those in which only some of the peptide bonds are reversed and the chirality of only those amino acid residues in the reversed portion is inverted. In one example, a retro-inverso peptide analog comprises a sequence set forth in SEQ ID NO: 36 or 37.

Protein Transduction Domains

Some peptides or polypeptides must enter a cell to exert their biological activity. To facilitate peptide entry into a cell, the peptide or polypeptide may be conjugated to (e.g., expressed as a fusion with) a protein transduction domain. As used herein, the term "protein transduction domain" shall be taken to mean a peptide or protein that is capable of enhancing, increasing or assisting penetration or uptake of a compound conjugated to the protein transduction domain into a cell either in vitro or in vivo. Those skilled in the art will be aware that synthetic or recombinant peptides can be delivered into cells through association with a protein transduction domain such as the TAT sequence from HIV or the Penetratin sequence from the Antennapaedia homeodomain protein (see, for example, Temsamani and Vidal, *Drug Discovery Today* 9: 1012-1019, 2004, for review).

A suitable protein transduction domain will be apparent to the skilled artisan and includes, for example, HIV-1 TAT basic region (e.g., SEQ ID NO: 8) or polyarginine (e.g., SEQ ID NO: 9).

For example, a HIV-1 TAT basic region has been shown to be capable of delivering a polypeptide into an IVD cell, e.g., US Patent Publication No. 20040197867.

Additional suitable protein transduction domains are described, for example, by Zhao and Weisledder *Medicinal Research Reviews*, 24: 1-12, 2004; or by Wagstaff and Jam, *Current Medicinal Chemistry*, 13: 1371-1387, 2006; or in US Patent Publication No. 20040197867.

Linkers

A peptide or polypeptide modulator of GDF-6 signaling may be linked to another peptidyl moiety (e.g., for immunodetection such as a FLAG epitope, or for targeting such as a protein transduction domain), albeit separated there from by a linker.

Preferred linkers facilitate the independent folding of each peptidyl moiety in the assembled peptide or polypeptide, thereby reducing steric hindrance of one moiety by another moiety. The amino acid composition of a linker peptide is important for stability and folding of a fusion protein, rather than a specific sequence (Robinson and Sauer *Proc. Natl. Acad. Sci.* 95: 5929-5934, 1998).

Suitable linkers will be apparent to the skilled artisan and are predominantly hydrophilic, i.e. the residues in the linker are hydrophilic.

It is also often unfavorable to utilize a linker sequence having a high propensity to adopt α-helix or β-strand structures, which could limit the flexibility of the peptidyl moieties and reduce functionality. Accordingly, preferred linkers may have a preference to adopt extended conformations.

Preferred linkers comprise a high content of glycine and/or serine residues. Linkers comprising glycine and/or serine have a high freedom degree for linking of two proteins, i.e., they enable the fused proteins to fold and produce functional proteins.

Glycine-rich linkers are particularly preferred because they force the linker to adopt a loop conformation. The absence of a β-carbon from glycine also permits the polypeptide backbone to access dihedral angles that are energetically forbidden for other amino acids. A particularly preferred linker in the present context consists of polyglycine i.e., between about 2 and 6 glycine residues, or a single glycine residue.

Chemical Synthesis of Peptides, Polypeptides and Analogs Thereof.

GDF-6 modulatory peptides or polypeptides and any derivatives, analogs or homologs thereof are readily synthesized from their determined amino acid sequences using standard techniques, e.g., using BOC or FMOC chemistry. Synthetic peptides and polypeptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, *J. Am. Chem. Soc.*, 85:2149-2154, 1963, or the base-labile Nα-amino protected 9-fluorenylmethoxycarbonyl (Fmoc) amino acids described by Carpino and Han, *J. Org. Chem.*, 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

The Merrifield method of synthesis (Merrifield, *J Am Chem Soc*, 85:2149-2154, 1963) and the myriad of available improvements on that technology are described in the art (see e.g., Synthetic Peptides: A User's Guide, Grant, ed. (1992) W.H. Freeman & Co., New York, pp. 382; Jones (1994) The Chemical Synthesis of Peptides, Clarendon Press, Oxford, pp. 230.); Barany, G. and Merrifield, R. B. (1979) in *The Peptides* (Gross, E. and Meienhofer, J. eds.), vol. 2, pp. 1-284, Academic Press, New York; Wiinsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart; Bodanszky, M. (1984) *Principles of Peptide Synthesis*, Springer-Verlag, Heidelberg; Bodanszky, M. & Bodanszky, A. (1984) *The Practice of Peptide Synthesis*, Springer-Verlag, Heidelberg; Bodanszky, M. (1985) *Int. J. Peptide Protein Res.* 25, 449-474.

Generally, chemical synthesis methods comprise the sequential addition of one or more amino acids to a growing peptide chain. Normally, either the amino or carboxyl group of the first amino, acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a peptide of the present invention or an analog or derivative thereof.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

A peptide, polypeptide, analog or derivative as described herein can also be chemically prepared by other methods such as by the method of simultaneous multiple peptide synthesis. See, e.g., Houghten *Proc. Natl. Acad. Sci. USA* 82: 5131-5135, 1985 or U.S. Pat. No. 4,631,211.

Synthetic peptides may also be produced using techniques known in the art and described, for example, in Stewart and Young (In: Solid Phase Synthesis, Second Edition, Pierce Chemical Co., Rockford, Ill. (1984) and/or Fields and Noble (*Int. J. Pept. Protein Res.*, 35:161-214, 1990), or using automated synthesizers.

Recombinant Peptide Production

Alternatively, or in addition, a peptide or polypeptide or analogue or derivative thereof or fusion protein comprising same is produced as a recombinant protein. To facilitate the production of a recombinant peptide or fusion protein nucleic acid encoding same is preferably isolated or synthesized. Typically the nucleic acid encoding the recombinant protein is/are isolated using a known method, such as, for example, amplification (e.g., using PCR or splice overlap extension) or isolated from nucleic acid from an organism using one or more restriction enzymes or isolated from a library of nucleic acids. Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For expressing protein by recombinant means, a protein-encoding nucleic acid is placed in operable connection with a promoter or other regulatory sequence capable of regulating expression in a cell-free system or cellular system. For example, nucleic acid comprising a sequence that encodes a peptide is placed in operable connection with a suitable promoter and maintained in a suitable cell for a time and under conditions sufficient for expression to occur. Nucleic acid encoding a peptide or polypeptide modulator of GDF-6 signaling is described herein or is derived from the publicly available amino acid sequence or the publicly available nucleotide sequence.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Preferred promoters can contain additional copies of one or more specific regulatory elements to further enhance expression and/or alter the spatial expression and/or temporal expression of said nucleic acid.

As used herein, the term "in operable connection with", "in connection with" or "operably linked to" means positioning a promoter relative to a nucleic acid such that expression of the nucleic acid is controlled by the promoter. For example, a promoter is generally positioned 5' (upstream) to the nucleic acid, the expression of which it controls. To construct heterologous promoter/nucleic acid combinations (e.g., promoter/nucleic acid encoding a polypeptide), it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

Should it be preferred that a peptide or polypeptide of the invention is expressed in vitro a suitable promoter includes, but is not limited to a T3 or a T7 bacteriophage promoter (Hanes and Plückthun *Proc. Natl. Acad. Sci. USA,* 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the Ipp promoter, temperature-sensitive XL or XR promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO or pBAD/thio-TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer Inc., CT, USA); the pQE series of expression vectors (QIAGEN, CA, USA), or the pL series of expression vectors (Invitrogen), amongst others.

Typical promoters suitable for expression in eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRαtkneo (Muller et al., *Mol. Cell. Biol.,* 11, 1785, 1991).

A wide range of additional host/vector systems suitable for expressing a peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

1.2 Nucleic Acid Modulators

In another example, a modulator is a nucleic acid. For example, the modulator is a nucleic acid that encodes a polypeptide modulator as described herein above.

In one example, a nucleic acid modulator encodes a polypeptide selected from the group consisting of:
(i) a nucleic acid encoding a polypeptide selected from the group consisting of GDF-6, MSX-1, MSX-2, BMPR-1A, BMPR-IB, BMPR-II, Smad-1, Smad-5, Smad-8 and Smad-4; and
(ii) a nucleic acid encoding an active fragment of a polypeptide selected from the group consisting of GDF-6, MSX-1, MSX-2, BMPR-1A, BMPR-IB, BMPR-II, Smad-1, Smad-5, Smad-8 and Smad-4.

In one preferred example of the invention, a modulator of GDF-6 signaling in an IVD or cell or tissue thereof is a nucleic acid encoding a GDF-6 polypeptide or an active fragment thereof. For example, the nucleic acid comprises a sequence at least about 80% identical to the sequence set forth in SEQ ID NO: 1, wherein said nucleic acid encodes a polypeptide capable of modulating GDF-6 signaling in an IVD or cell or tissue thereof. Preferably, the nucleic acid has at least about 90% identity or 95% identity or 98% identity or 99% identity to the sequence set forth in SEQ ID NO: 1, wherein said nucleic acid encodes a polypeptide capable of modulating GDF-6 signaling in an IVD or cell or tissue thereof.

In another example, a modulator of GDF-6 signaling in an IVD or cell or tissue thereof is a nucleic acid that encodes a MSX-1 polypeptide or an active fragment thereof. For example, a sequence at least about 80% identical to the sequence set forth in SEQ ID NO: 4, wherein said nucleic acid encodes a polypeptide capable of modulating GDF-6 signaling in an IVD or cell or tissue thereof. Preferably, the nucleic acid has at least about 90% identity or 95% identity or 98% identity or 99% identity to the sequence set forth in SEQ ID NO: 4, wherein said nucleic acid encodes a polypeptide capable of modulating GDF-6 signaling in an IVD or cell or tissue thereof.

In another example, a modulator of GDF-6 signaling in an IVD or cell or tissue thereof is a nucleic acid that encodes a MSX-2 polypeptide or an active fragment thereof. For example, the nucleic acid comprises a sequence at least about 80% identical to the sequence set forth in SEQ ID NO: 6, wherein said nucleic acid encodes a polypeptide capable of modulating GDF-6 signaling in an IVD or cell or tissue thereof. Preferably, the nucleic acid has at least about 90% identity or 95% identity or 98% identity or 99% identity to the sequence set forth in SEQ ID NO: 6, wherein said nucleic acid encodes a polypeptide capable of modulating GDF-6 signaling in an IVD or cell or tissue thereof.

The nucleotide sequence of additional nucleic acids capable of encoding a peptide or polypeptide modulator of GDF-6 signaling are readily derivable from publicly available databases, such as, for example, the Genbank database available from NCBI. Moreover, methods for determining a peptide or polypeptide having GDF-6 modulatory activity will be apparent to the skilled artisan, e.g., based on the description herein.

For example, the nucleic acid modulator is a nucleic acid encoding a polypeptide modulator described herein above operably-linked to a promoter for inducing expression in an IVD or a cell or tissue thereof. For example, the nucleic acid is linked to a promoter operable in a variety of cells of a subject, such as, for example, a viral promoter, e.g., a CMV promoter (e.g., a CMV-IE promoter) or a SV-40 promoter. The nucleic acid may also be linked to a promoter that expresses a nucleic acid in an IVD or cell or tissue thereof in nature, such as, for example, a collagen promoter or a matrix metalloproteinase promoter. Additional suitable promoters are described herein and shall be taken to apply mutatis mutandis to the present embodiment of the invention.

Preferably, the nucleic acid modulator of GDF-6 signaling in an IVD or cell or tissue thereof is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present invention, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001).

For example, each of the components of the expression construct is amplified from a suitable template nucleic acid using, for example, PCR and subsequently cloned into a suitable expression construct, such as for example, a plasmid or a phagemid. Alternatively, the nucleic acid required for the assay is, for example, excised from a suitable source, for example, using a restriction endonuclease and cloned into a suitable expression construct.

Vectors suitable for such an expression construct are known in the art and/or described herein. For example, an expression vector suitable for the method of the present invention in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP16 vector (Clontech) or a vector of the pcDNA vector suite (Invitrogen).

The skilled artisan will be aware of additional vectors and sources of such vectors, such as, for example, Invitrogen Corporation, Clontech or Promega.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SW), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:274-2378 (1989); Miller et al., *J. Virol.* 65:2220-2224 (1991); PCT/US94/05700; Miller and Rosman *BioTechniques* 7:980-990, 1989; Miller, A. D. *Human Gene Therapy* 1:5-14, 1990; Scarpa et al) *Virology* 180:849-852, 1991; Burns et al. *Proc. Natl. Acad. Sci. USA* 90:8033-8037, 1993.).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 8:3988-3996, 1988; Vincent et al. (1990) Vaccines 90 (Cold Spring Harbor Laboratory Press); *Carter Current Opinion in Biotechnology* 3:533-539, 1992; Muzyczka. *Current Topics in Microbiol. and Immunol.* 158:97-129, 1992; Kotin, *Human Gene Therapy* 5:793-801, 1994; Shelling and Smith *Gene Therapy* 1:165-169, 1994; and Zhou et al. *J. Exp. Med.* 179:1867-1875, 1994.

Additional viral vectors useful for delivering an expression construct of the invention include, for example, those derived from the pox family of viruses, such as vaccinia virus and avian poxvirus or an alphavirus or a conjugate virus vector (e.g. that described in Fisher-Hoch et al., *Proc. Natl. Acad. Sci. USA* 86:317-321, 1989).

The skilled artisan will be aware based on the foregoing description that the present invention also provides a composition comprising (i) a virus comprising a nucleic acid encoding a modulator of GDF-6 signaling in an IVD or a cell or tissue thereof sufficient to reduce, delay or prevent IVD degeneration in a subject and/or to induce and/or enhance IVD regeneration in a subject and a suitable carrier or excipient.

1.3 Cell-Based Modulators

The present invention also encompasses a composition comprising a cell, e.g., a stem cell comprising and/or expressing a modulator of GDF-6 signaling in an IVD or cell or tissue thereof. For example, the cell is transformed, transfected or transduced with a nucleic acid capable of expressing a peptide or polypeptide modulator of GDF-6 signaling, e.g., as described supra.

In one example, the cell is isolated from an IVD. For example, the cell is a nucleus pulposus cell or an annulus fibrosus cell. For example, the cell is isolated from a subject to be treated. For example, an IVD cell is isolated from a subject, e.g., using a syringe or by surgery. The cell is then transfected, transduced or transformed with a nucleic acid, e.g., an expression construct, capable of expressing a peptide or polypeptide modulator of GDF-6 signaling in said cell. Such a cell may then be introduced into a subject suffering from a spinal disorder and/or spinal pain.

In a preferred example, a cell is a stem cell. For example, a cell is a stem cell capable of differentiating into a cell in an IVD. Such a cell is useful for populating an IVD to which it is administered and reduce, prevent or delay IVD degeneration and/or enhance or induce IVD regeneration. Suitable stem cells will be apparent to the skilled artisan and include, a mesenchymal stem cell or a bone marrow stromal cell.

A suitable cell includes, for example, multipotent cells such as those described by Jiang, et al. (Nature, Vol. 418, p. 41-49, 2002).

Alternatively, a bone-marrow mesenchymal stem cell is isolated from a subject, e.g., a subject in need of treatment, and transformed, transfected or transduced with a nucleic acid capable of expressing a peptide or polypeptide modulator of GDF-6 signaling. Methods for isolating and/or administering a bone-marrow stromal cell will be apparent to the skilled artisan and/or described, for example, in Richardson et al., Stem Cells, 24: 707-716, 2006.

For example, a natural source of mesenchymal stem cells include bone marrow (e.g., with and without previous bleeding), peripheral blood (e.g., with and without enhancement from marrow), umbilical cord, fat, muscle, blood vessels, periosteum and perichondrium. Stem cells may be isolated from such a source by any suitable method, typically involving cell fractionation and concentration. Suitable methods are known in the art and include Ficoll-Paque methodology or concentration of mesenchymal stem cells using antibodies directed to mesenchymal stem cell markers which are immobilized, for example in an affinity chromatography column or to a substratum in a "panning" scheme.

Preferably a stem cell is allogenic (i.e., from the same species as a subject to be treated, and, preferably from the subject to be treated), as opposed to xenogenic (i.e., from a different species). If the cells are allogenic, but not autologous, it is preferred if the cells are of a similar tissue type (e.g. have similar MHC/HLA haplotypes). It is particularly preferred if the cells are autologous (i.e., are derived from the subject to which they are administered). Such autologous cells have the advantage of being less prone to rejection compared to other allogenic (or xenogenic) cells. Also, the use of autologous cells avoids any issue of "doping" (e.g., with "foreign" DNA). Accordingly, one example of the invention comprises obtaining a mesenchymal stem cell from a subject, transforming or transfecting the stem cell with a nucleic acid encoding a peptide or polypeptide modulator of GDF-6 signaling. It will be appreciated that some of the cells may be saved for use at a later date, and typically such cells are frozen under conditions that retains their viability. It will be appreciated that the cells may be obtained and enriched (expanded if necessary) before IVD degeneration in a subject, and kept for immediate administration when necessary.

Alternatively, or in addition, a bone-marrow stem cell comprising or expressing a modulator of GDF-6 signaling is cultured with a cell isolated from an IVD, e.g., a nucleus pulposus cell, prior to administration to a subject. Such co-cultivation induces differentiation of the stem cell into a cell similar to an IVD cell (Richardson et al., supra).

In one example, the cell is a chondrocyte, e.g., a progenitor cell capable of differentiating into an IVD cell, e.g., a nucleus pulposus cell or an annulus fibrosus cell. Chondrocytes generally express a marker such as, for example, Type II Collagen; Collagen IX; Aggrecan; Link Protein; S100; or Biglycan. The skilled artisan will be aware of methods for producing or isolating such a chondrocyte. For example, as exemplified herein, contacting a mesenchymal stem cell, e.g., a bone marrow mesenchymal stem cell with GDF-6 for a time and under conditions sufficient for differentiation to occur causes the cell to differentiate into a chondrocyte. Such a chondrocyte is then suitable for administration to a subject to treat IVD degeneration and/or spinal pain and/or to induce IVD regeneration. Preferably, the chondrocyte has been modified to comprise or express a modulator of GDF-6 signaling.

In another example, an isolated stem cell, e.g., a bone marrow mesenchymal stem cell is contacted with a transforming growth factor (TGF)-β3 protein and/or a BMP-2 protein and/or a GDF-6 protein to induce differentiation into a chondrocyte cell, preferably a nucleus pulposus-like cell. Suitable methods for inducing differentiation are exemplified herein.

In one example, the composition described herein according to any embodiment, comprises a liquid suspension of cells comprising or expressing a modulator of GDF-6 signaling. For example, the liquid suspension is a suspension of cells in a medium that contains appropriate biological signals to encourage the differentiation of the mesenchymal stem cells into an IVD-type cell, and/or to discourage the differentiation of the cells into cell types that are not useful (e.g., bone tissue). The liquid suspension may be one which gels in situ, for example because of the temperature at the injury site of the patient, or because it is mixed with another agent that causes gelling.

In one example of the present invention, the cell additionally expresses a catalytic subunit of telomerase, e.g., encoded by a TERT gene or transcript. For example, the cell is genetically modified to express a catalytic subunit of telomerase. Such cells produce increased levels of collagen, e.g., collagen type 1 and/or collagen type 2. Suitable cells and methods for producing those cells are described, for example, in applicant's co-pending International Patent Application No. PCT/AU2006/000550.

In one example, a cell is isolated from a subject, e.g., an IVD cell and is transfected with an expression vector or expression construct comprising a nucleic acid encoding TERT operably linked to a promoter active in said cell. In one example, the cell is additionally transfected with a nucleic acid encoding a modulator of GDF-6 signaling. Methods for transfecting cells, e.g., IVD cells will be apparent to the skilled artisan and/or described herein and/or described in International Patent Application No. PCT/AU2006/000550. The resulting recombinant cell is then administered to a subject using a method described herein.

As will be apparent to the skilled artisan based on the foregoing description, the present invention also provides a method additionally comprising isolating or obtaining a stem cell. Such a method may additionally comprise producing a stem cell comprising or expressing a modulator of GDF-6 signaling, e.g., by performing a process comprising transforming or transfecting a stem cell with a nucleic acid that encodes a peptide or polypeptide modulator of GDF-6 signaling.

The present invention also provides a method for obtaining a chondrocyte or chondrocyte-like cell or a nucleus pulposus-like cell, said method comprising contacting a stem cell or a progenitor cell or a multipotent cell or a totipotent cell with an inducer of GDF-6 signaling, preferably, a GDF-6 polypeptide or active fragment thereof for a time and under conditions for the cell to differentiate, wherein following differentiation the cell is a chondrocyte or chondrocyte-like cell or a nucleus pulposus-like cell.

In one example, the stem cell or the progenitor cell or the multipotent cell is a mesenchymal stem cell, preferably a bone marrow mesenchymal stem cell.

In another example, the method additionally comprises contacting the stem cell or a progenitor cell or a multipotent cell or totipotent cell with a TGF-133 polypeptide and/or a BMP2 polypeptide.

The present invention also provides a chondrocyte or chondrocyte-like cell or a nucleus pulposus-like cell produced by a method described herein according to any embodiment.

The present invention also provides a method of treating preventing or delaying or treating a spinal disorder and/or spinal pain in a subject, said method comprising administering a chondrocyte or chondrocyte-like cell or a nucleus pulposus-like cell produced by a method described herein according to any embodiment to a subject suffering from a spinal disorder and/or spinal pain for a time and under conditions sufficient to reduce, delay or prevent intervertebral disc (IVD) degeneration in the subject and/or to induce and/or enhance intervertebral disc regeneration in the subject.

1.4 Assays to Identify a Modulator of GDF-6 Signaling

The skilled artisan will be aware of suitable methods for determining a compound capable of modulating GDF-6 signaling.

For example, a cell expressing a reporter gene, e.g., β-galactosidase or a fluorescent protein (e.g., green fluorescent protein) is placed under control of a BRE promoter, which is induced in the presence of GDF-6 signaling. The cell is then contacted with a test compound and the level of reporter gene expression is determined. A compound that enhances or reduces GDF-6 signaling compared to a cell that has not been contacted with a compound is considered a modulator of GDF-6 signaling. Such a method is described, for example, in Mazerbourgh et al., *J. Biol. Chem.*, 280: 32122-32132, 2005.

Alternatively, or in addition, a cell is contacted with a test compound for a time and under conditions sufficient for GDF-6 signaling to occur and protein isolated from said cell. The level of phosphorylated Smad 1, Smad 5 and/or Smad 8 is then determined, e.g., by Western blotting using an anti-phospho Smad 1, Smad 5 or Smad 8 antibody (e.g., as available from Amersham Pharmacia). A compound that enhances or reduces the level of phosphorylated Smad 1, Smad 5 and/or Smad 8 in a cell compared to a cell that is not contacted with the compound is then considered a modulator of GDF-6 signaling. Such an assay is described, for example, in Mazerbourgh et al., supra.

In one example, the method described in either of the previous two paragraphs is performed in a cell from an IVD, e.g., a nucleus pulposus cell or an annulus fibrosus cell or in a cell in an IVD organ culture. Such an assay is useful for identifying a compound that modulated GDF-6 signaling in an IVD or cell or tissue thereof.

For example, GDF-6 signaling modulators may be identified by their ability to enhance or reduce the binding of two or more members of the GDF-6 signaling pathway to one another, e.g., a GDF-6 polypeptide to a GDF-6 receptor. For example, an assay is performed in which a labeled GDF-6 is contacted to a GDF-6 receptor in the presence or absence of a test compound. Following washing, the level of bound label is detected. A compound that enhances or reduces the level of label bound to the GDF-6 receptor is considered a modulator of GDF-6 signaling. Alternatively, or in addition, a GDF-6 signaling modulator is identified by their ability to enhance or inhibit protein interactions in the GDF-6 signaling cascade.

For example, a reverse hybrid assay or forward hybrid assay is employed to identify a test compound inhibits or reduces or enhances an interaction between any of the following proteins: GDF-6 and/or MSX-1 and/or MSX-2 and/or BMPR-1A and/or BMPR-IB and/or BMPR-II and/or Smad-1 and/or Smad-5 and/or Smad-8 and/or Smad-4. Reverse hybrid methods will be apparent to the skilled artisan and/or described in Watt et al. (U.S. Ser. No. 09/227,652) or Erickson et al. (WO95/26400).

1.5 Assays to Determine Modulators of IVD Degeneration and/or Regeneration

The skilled artisan will also be aware of a suitable method to determine a compound and/or an amount of a compound that reduces, prevents or delays IVD degeneration and/or enhances IVD regeneration.

For example, an assay is performed in a cultured cell, e.g., a cell from an WD, e.g., a nucleus pulposus cell or an annulus fibrosus cell or a similar cell or cell line, or a stem cell. For example, a cell is contacted with a test compound for a time and under conditions sufficient to modulate GDF-6 signaling and the level of a marker of IVD degeneration and/or regeneration, e.g., proteoglycan content and/or collagen content or production is determined. For example, a compound that enhances proteoglycan content of a cell and/or collagen content or production of a cell compare to a cell that is not contacted with the compound is considered reduces, prevents or delays IVD degeneration and/or enhances IVD regeneration.

Methods for determining the level of proteoglycan in a cell will be apparent to the skilled artisan and includes, for example, an assay to detect sulphated glycosaminoglycan using the metachromatic dye 1,9-dimethylmethylene blue (e.g., as described in Melrose et al., *J Orthop Res* 10:665-676, 1992; and Melrose et al., Matrix 14:61-75, 1994).

An assay for detecting collagen content of a cell includes, for example, an assay to detect hydroxyproline (e.g., essentially as described in Melrose et al., *J Orthop Res* 10:665-676, 1992; and Melrose et al., *Matrix* 14:61-75, 1994). Alternatively, or in addition, immunohistochemistry and/or immunofluorescence is used to detect the level of a collagen in a cell, e.g., Collagen Type I, Collagen Type II, Collagen Type IV, Collagen Type VI and Collagen Type X. Alternatively, or in addition, uptake of H-proline by a cell is indicative of the level of collagen synthesis by the cell.

Alternatively, or in addition a compound is administered to an animal model of ND degeneration, such as for example, an animal model described herein. The effect of the compound is then determined, e.g., the water content of an ND and/or the height of an IVD to which a compound has been administered is compared to the same parameter of an IVD to which the compound has not been administered. Improvement of the parameter indicates that the compound reduces, prevents or delays ND degeneration and/or enhances IVD regeneration. Alternatively, the parameter in a treated IVD is compared to the same parameter in a non-degenerating IVD, and a similar level is indicative of a compound that reduces, prevents or delays IVD degeneration and/or enhances IVD regeneration.

Additional in vivo assays are exemplified herein.

2. Formulations

The GDF-6 signaling modulatory composition as described herein according to any embodiment can be formulated readily for administration to a subject in need thereof e.g., by admixing the composition with a suitable carrier and/or excipient.

The terms "carrier" and "excipient" refer to carriers and excipients that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the formulation. In one example, the carrier does not produce significant local or systemic adverse effect in recipients at the dosages and concentrations employed for treatment.

Suitable carriers for this invention include those conventionally used, e.g., water, saline, aqueous dextrose, lactose, Ringer's solution, a buffered solution, hyaluronan and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

Preferred carriers and excipients do not adversely affect the ability of a GDF-6 signaling modulator to reduce, prevent or delay IVD degeneration and/or adversely affect the ability of a GDF-6 signaling modulator to enhance or induce IVD regeneration.

In one example, the carrier or excipient provides a buffering activity to maintain the compound at a suitable pH to thereby exert its biological activity, e.g., the carrier or excipient is phosphate buffered saline (PBS). PBS represents an attractive carrier or excipient because it interacts with compounds minimally and permits rapid release of the compound. In such a case, the composition of the invention may be produced as a liquid or direct application to an IVD or a region surrounding or adjacent to an IVD, e.g., by injection.

In another example, the composition of the invention is formulated with a co-polymer. For example, Puolakkainen et al., *J. Surg. Res.*, 58: 321-329 describe a poly(ethylene oxide)-poly(propylene oxide) block copolymer designated Pluronic F-127. Pluronic F-127 has been used as a carrier for a variety of peptides and proteins in addition to nucleic acid based compounds. This carrier exhibits thermoreversability, relative inertness toward protein and nucleic acid and low toxicity.

In a further example, the carrier is a hydrogel. In this respect, a hydrogel is a three dimensional network of cross-linked hydrophilic polymers in the form of a gel substantially composed of water, preferably but not limited to gels being greater than 90% water. Hydrogel can carry a net positive or net negative charge, or may be neutral. A typical net negative charged hydrogel is alginate. Hydrogels carrying a net positive charge may be typified by extracellular matrix components such as collagen and laminin. Examples of commercially available extracellular matrix components include Matrigel™ and Vitrogen™. An example of a net neutral hydrogel is highly crosslinked polyethylene oxide, or polyvinylalcohol. For example, biopol hydrogel is a poly(ethylene oxide) cross-linked hydrogel that interacts with aqueous solutions and swells to an equilibrium value, retaining a significant portion of the aqueous solution within its structure. Hydrogels have been shown to be suitable for delivery of a number of compounds, including proteins or peptides (Pitt et al., *Int. J. Pharm.*, 59: 173, 1990.

In a further example, the carrier is a hydroxypropyl methylcellulose (HPMC) or a hydroxypropyl cellulose (HPC). Such carriers may be formulated as a liquid, a gel or a cream.

Optionally, the carrier additionally comprises n-methyl-2-pyrrolidine (NMP) to enhance uptake of a topical composition therein.

In the case of a cell-based therapeutic a preferred carrier includes a hyaluronan gel. Alternatively, or in addition, a suitable hydrogel for administration of a cell or peptide or nucleic acid is described in US Patent Publication No. 20060115457.

In a further example, a GDF-6 signaling modulator is formulated with polyethylene glycol (PEG) as a delivery material. The PEG group(s) may be of any convenient molecular weight and may be linear or branched. For example, the composition comprises PEG. Alternatively, or in addition, the GDF-6 signaling modulator is covalently linked to the PEG group(s). Methods for PEGylating proteins are known in the art.

In another example, the clearance of a GDF-6 signaling modulator is delayed to extend the effective half-life of the GDF-6 modulator at the site of action (i.e., within an IVD, e.g., within a nucleus pulposus and/or within a region of an IVD defined by an annulus fibrosus) by appropriate formulation e.g., for sustained-release of the GDF-6 signaling modulator and/or for slow delivery of the GDF-6 signaling modulator. Formulations comprising gels, hydrogels, microspheres or biocompatible polymers, including bioresorbable polymers, are particularly suited to such applications. Suitable formulations for such applications may comprise, for example, polylactic/polyglycolic acid polymers, liposomes, collagen, polyethylene glycol (PEG), hyaluronic acid/fibrin matrices, hyaluronic acid, fibrin, chitosan, gelatin, SABER™ System (sucrose acetate isobutyrate (SAIB)), DURIN™ (biodegradabale polymer for drug loaded implants), MICRO-DUR™ (biodegradable polymers/microencapsulation) and DUROS™ (mini-osmotic pump). Biocompatible polymeric materials include elastic or elastomeric materials, hydrogels or other hydrophilic polymers, or composites thereof. Suitable elastomers include silicone, polyurethane, copolymers of silicone and polyurethane, polyolefins, such as polyisobutylene and polyisoprene, neoprene, nitrile, vulcanized rubber and combinations thereof. Suitable hydrogels include natural hydrogels, and those formed from polyvinyl alcohol, acrylamides such as polyacrylic acid and poly (acrylonitrile-acrylic acid), polyurethanes, polyethylene glycol, poly (N-vinyl-2-pyrrolidone), acrylates such as poly (2-hydroxy ethyl methacrylate) and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include naturally occurring materials such as glucomannan gel, hyaluronic acid, polysaccharides, such as cross-linked carboxyl-containing polysaccharides, and combinations thereof.

Formulations of the present invention can be subjected to conventional pharmaceutical expedients, such as sterilization, and can contain a conventional pharmaceutical additive, such as a preservative and/or a stabilizing agent and/or a wetting agent and/or an emulsifying agent and/or a salt for adjusting osmotic pressure and/or a buffer and/or other additives known in the art. Other acceptable components in the composition of the invention include, but are not limited to, isotonicity-modifying agents such as water and/or saline and/or a buffer including phosphate, citrate, succinate, acetic acid, or other organic acids or their salts.

In one example, a formulation of the invention includes one or more stabilizers, reducing agents, anti-oxidants and/or anti-oxidant chelating agents. The use of buffers, stabilizers, reducing agents, anti-oxidants and chelating agents in the preparation of compositions, is known in the art and described, for example, in Wang et al. *J. Parent. Drug Assn.* 34:452-462, 1980; Wang et al. *J. Parent. Sci. Tech.* 42:S4-S26 (Supplement), 1988. Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. Suitable salts and isotonicifiers include sodium chloride, dextrose, mannitol, sucrose, trehalose, or the like. Where the carrier is a liquid, it is preferred that the carrier is hypotonic or isotonic with oral, conjunctival, or dermal fluids and has a pH within the range of 4.5-8.5. Where the carrier is in powdered form, it is preferred that the carrier is also within an acceptable non-toxic pH range.

In another example, a formulation as described herein according to any embodiment additionally comprises a liposome carrier or excipient to facilitate uptake of a GDF-6 signaling modulator into a cell. Liposomes are considered to interact with a cell by stable absorption, endocytosis, lipid transfer, and/or fusion (Egerdie et al., *J. Urol.* 142:390, 1989). For example, liposomes comprise molecular films, which fuse with cells and provide optimal conditions for wound healing (K. Reimer et al., *Dermatology* 195(suppl. 2):93, 1999). Generally, liposomes have low antigenicity and can be used to encapsulate and deliver components that cause undesirable immune responses in patients (Natsume et al., *Jpn. J. Cancer Res.* 91:363-367, 2000)

For example, anionic or neutral liposomes often possess excellent colloidal stability, since substantially no aggregation occurs between the carrier and the environment. Consequently their biodistribution is excellent, and their potential for irritation and cytotoxicity is low.

Alternatively, cationic liposomal systems, e.g. as described in Mauer et al., *Molecular Membrane Biology*, 16: 129-140, 1999 or Maeidan et al., *BBA* 1464: 251-261, 2000 are useful for delivering compounds into a cell. Such cationic systems provide high loading efficiencies. Moreover, PEGylated cationic liposomes show enhanced circulation times in vivo (Semple *BBA* 1510, 152-166, 2001).

Amphoteric liposomes are a recently described class of liposomes having an anionic or neutral charge at pH 7.4 and a cationic charge at pH 4. Examples of these liposomes are described, for example, in WO 02/066490, WO 02/066012 and WO 03/070735. Amphoteric liposomes have been found to have a good biodistribution and to be well tolerated in animals and they can encapsulate nucleic acid molecules with high efficiency.

U.S. Ser. No. 09/738,046 and U.S. Ser. No. 10/218,797 describe liposome formulations suitable for the delivery of peptides or proteins into a cell.

In one example, a carrier or excipient comprises poly(m-ethyl methacrylate) (PMMA), optionally chondroitin sulphate (CS), an amphiphilic macromonomer (MT), 2-hydroxyethyl methacrylate (HEMA) and, optionally, acrylic acid (AA), as described in Larraz et al., *J. Tissue Eng. and Regen. Med.*, 1: 120-127, 2007.

In the case of a nucleic acid based modulator of GDF-6 signaling a carrier or excipient preferably comprises a lipid-based agent, e.g., a cationic lipid. For example, the carrier or excipient comprises a cationic lipid, such as 2,3-dioleyloxy-N-[2(sperminecarboxyamido)ethyl]-N,N-dimethyl-1-propanaminium trifluoroacetate), Lipofectin, Lipofectace, DOTAP, DOTMA (N-[1-(2,3-dioleyloxy)propyl]-N,N,N-trimethylammonium chloride), CDAB (cetyldimethylethylammonium bromide), CTAB (cetyltrimethylethylammonium bromide), DDAB (dimethyldioctadecylammonium bromide), MBC (methylbenzethonium chloride), FuGENE (Roche) or stearylamine. Other suitable lipids are disclosed, for example in U.S. Pat. No. 5,855,910, International Patent Publication No. WO 02/072068 and International Patent Publication No. WO 00/30444.

3. Medical Devices

The present invention also provides a medical device comprising an amount of a modulator of GDF-6 signaling in an IVD or a cell or tissue thereof sufficient to reduce, delay or prevent IVD degeneration in a subject and/or to induce and/or enhance IVD regeneration in a subject or comprising a composition as described herein according to any embodiment.

For example, the medical device is a syringe comprising a composition described herein according to any embodiment.

In one example, the medical device comprising the modulator of GDF-6 signaling is a device comprising a delivery conduit having a proximal end attachable to a source of the GDF-6 signaling modulator and an emitter structure at a distal end of the delivery conduit, wherein the emitter structure defines a plurality of spaced discharge apertures through which the GDF-6 signaling modulator is delivered to a plurality of sites or in a patterned manner within the IVD and/or within a nucleus pulposus and/or adjacent to a nucleus pulposus and/or within a region of an IVD defined by an annulus fibrosus and wherein the emitter structure is configured to promote diffuse distribution of the GDF-6 signaling modulator within or throughout the IVD, e.g., within a nucleus pulposus and/or adjacent to a nucleus pulposus and/or within a region of an IVD defined by an annulus fibrosus. Preferably, the apertures are dimensioned to achieve a substantially uniform discharge rate of the GDF-6 signaling modulator or composition of the invention through all of the apertures.

The emitter structure of such a device may be steerable. Thus the emitter structure may include a pull wire attached to the emitter structure, either within a lumen of the emitter structure or embedded in a wall of the emitter structure. Instead, the device may include a guide element for guiding the emitter structure into an operative position at the site in which diffuse distribution of the GDF-6 signaling modulator or composition of the invention is promoted. The guide element may be a guide wire of a preformed shape extending through a lumen of the emitter structure. The guide wire may, for example, be of a shape memory alloy such as Nitinol®.

A wall of the emitter structure in such a device may be reinforced to maintain the integrity of the emitter structure in situ. More particularly, the emitter structure may be reinforced to inhibit collapsing of the lumen of the emitter structure as a result of pressure applied to the IVD or to the nucleus pulposus of an IVD or pressure applied adjacent to or surrounding the IVD.

For example, the emitter structure of such a device may be shaped to form a loop at the site of the IVD or the nucleus pulposus or a region of the IVD defined by an annulus fibrosus in the patient's body. In another embodiment, the emitter structure may be substantially annular. In still a further embodiment, the emitter structure may be forked into a plurality of branches. By "forked" is meant more than two branches.

The emitter structure of such a device may also be formed integrally with the delivery conduit as a one-piece unit. The device may include a working cannula via which the unit is able to be delivered into an IVD and/or into a nucleus puplosus and/or into a region of an ND defined by an annulus fibrosus percutaneously in a minimally invasive manner.

The emitter structure of such a device may also carry at least one radio-opaque marker.

Each aperture of such a device may include a flow control device for inhibiting back flow of the GDF-6 signaling modulator or composition of the invention into the emitter structure. The flow control device may be a one-way valve. The flow control device may be adjusted to improve the flow of formulations of higher viscosity.

The present invention clearly encompasses a system for the delivery of a GDF-6 signaling modulator or a composition of the present invention into an ND and/or into a nucleus puplosus and/or into a region of an IVD defined by an annulus fibrosus and/or adjacent to at least a portion of a nucleus pulposus, said system comprising a device as described according to any embodiment hereof, for example with reference to any one or more of FIGS. 8 to 18, and a source of the GDF-6 signaling modulator or composition of the present invention attached to the proximal end of the delivery conduit of the device. The source of the GDF-6 signaling modulator or composition can be a fluid dispenser, such as a syringe.

In a further example, the present invention provides a medical device for the delivery of a GDF-6 signaling modulator or composition of the present invention into an ND and/or into a nucleus puplosus and/or into a region of an IVD defined by an annulus fibrosus, and/or adjacent to at least a portion of a nucleus pulposus wherein the medical device comprises a delivery conduit having a proximal end attachable to a source of the GDF-6 signaling modulator or composition of the present invention and an emitter structure at a distal end of the delivery conduit, wherein the emitter structure is at least partially receivable within an interior of the IVD, preferably within a nucleus pulposus and/or within a region of an ND defined by an annulus fibrosus and/or adjacent to at least a portion of a nucleus pulposus and defining a plurality of spaced discharge apertures through which the GDF-6 signaling modulator or composition is delivered into the IVD and/or into the nucleus puplosus and/or into the region of an IVD defined by an annulus fibrosus and/or adjacent to at least a portion of a nucleus pulposus and wherein the emitter structure is configured to extend about a part of the IVD, e.g., a nucleus pulposus or a region of an IVD defined by an annulus fibrosus and/or adjacent to at least a portion of a nucleus pulposus to thereby promote administration of the GDF-6 modulator or composition to a plurality of sites or in a patterned manner within the IVD and/or nucleus puplosus and/or region of an IVD defined by an annulus fibrosus and/or adjacent to at least a portion of a nucleus pulposus, e.g., to promote diffuse or substantially uniform distribution of the GDF-6 signaling modulator or composition throughout the IVD and/or nucleus puplosus and/or region of an IVD defined by an annulus fibrosus.

In another example, the medical device comprises a synthetic or natural-sourced matrix configured in size and shape to fit the defect site to be repaired, e.g., an IVD or a nucleus pulposus or a region of an IVD defined by an annulus fibrosus.

In another example, the medical device comprises a spinal implant. For example, the spinal implant is for treating an IVD while retaining an intact annulus fibrosus, the device including a compressible fibrous body configurable to a compressed state for passage through an opening in the annulus fibrosus and into a disc cavity defined by the annulus fibrosus. The body is also configurable to an expanded state to reside within the disc cavity and have a dimension greater than the opening so as to resist expulsion from the opening. The body incorporates an effective amount of a modulator of GDF-6 signaling, or a cell (e.g., a stem cell, a nucleus pulposus cell or an annulus fibrosus cell comprising or expressing said modulator of GDF-6 signaling) or a composition of the present invention. Such a device is described, for example, in US Patent Publication No. 20020173851.

Alternatively, the device comprises a fibrous body sized for passage through an opening in the annulus fibrosus and into a disc cavity defined by the annulus fibrosus. The body is formed of fibers having coated thereon a solid carrier matrix incorporating a modulator of GDF-6 signaling or a composition of the present invention.

A medical device encompassed by the present invention, especially any implant, may be partially or completely bioresorbable. In addition, the body may be sized and configured to provide temporary or permanent prosthetic function, by being dimensioned to participate in the distribution of compressive loads between adjacent vertebral bodies. For example, the body may be adapted to physically maintain a space in the disc as new tissue is generated, and provide a substrate for tissue ingrowth which locks the implant in place and reinforces regenerated tissues to help maintain disc space height. Alternatively, the body may be non-prosthetic, while delivering a modulator of GDF-6 signaling. In such non-prosthetic applications, the device can be dimensioned, or can be formed of a material having compressive properties, such that it does not participate in the distribution of loads between the adjacent vertebral bodies.

A spinal disc implant contemplated by the present invention is fabricated in any of a variety of shapes, as desired for a particular application. Whilst, the implant may assume a variety of shapes, it is typically shaped to conform to the shape of the natural nucleus pulposus, at least when in its hydrated and/or relaxed configuration. Thus, the implant is preferably substantially elliptical when in its hydrated and/or relaxed configuration. In other forms of the invention, the shape of the implant in its hydrated and/or relaxed configuration is generally annular-shaped, cylindrical-shaped, or otherwise shaped as required to conform to a cavity in an IVD.

Suitable spinal disc implants are also shaped in a manner to allow easy implantation into a spinal disc nucleus space. Accordingly, the implant may have a narrow, tubular shape when in its dehydrated and/or straightened configuration, and may include at least one narrow or pointed end to facilitate implantation through a small annulus hole.

A spinal disc implant for use in the invention may be formed from a wide variety of biocompatible polymeric materials, including elastic materials, such as elastomeric materials, hydrogels or other hydrophilic polymers, or composites thereof. Suitable elastomers include silicone, polyurethane, copolymers of silicone and polyurethane, polyolefins, such as polyisobutylene and polyisoprene, neoprene, nitrile, vulcanized rubber and combinations thereof. Suitable hydrogels include natural hydrogels, and those formed from polyvinyl alcohol, acrylamides such as polyacrylic acid and poly (acrylonitrile-acrylic acid), polyurethanes, polyethylene glycol, poly (N-vinyl-2-pyrrolidone), acrylates such as poly (2-hydroxy ethyl methacrylate) and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include naturally occurring materials such as glucomannan gel, hyaluronic acid, polysaccharides, such as cross-linked carboxyl-containing polysaccharides, and combinations thereof. The nature of the materials employed to form the elastic body should be selected so the formed implants have sufficient load bearing capacity. In preferred embodiments, a compressive strength of at least about 0.1 Mpa is desired, however compressive strengths in the range of about 1 Mpa to about 20 Mpa are more preferred.

Additional suitable implants will be apparent to the skilled artisan and are described, for example, in International Application No. PCT/AU2006/000267.

4. Modes of Administration

The present invention contemplates any mode of administration of a modulator of GDF-6 signaling or a composition as described herein according to any embodiment in a method of treatment. For example, the present invention contemplates administration surgically or by injection or a combination thereof. Those skilled in the art will recognize that, notwithstanding implants and stents may be delivered readily by surgical means, and injectable formulations are generally delivered to the IVD region by injection, these modes of administration are not mutually exclusive. For example, an implant or stent may be amenable by virtue of its small size, flexibility or other physicochemical properties to be administered by injection.

Preferred means for injection of a GDF-6 modulatory composition include intravenous, subcutaneous, percutaneous, intramuscular and intradiscal routes. (e.g., intradiscal injection or intradiscal implant), the only requirement being that the GDF-6 modulatory compound is delivered to the region of the IVD in an amount effective to modulate the GDF-6 signaling pathway therein. Preferably, the composition or GDF-6 modulator is delivered into an IVD, more preferably into a nucleus puplosus and/or a region of an IVD defined by an annulus fibrosus.

For example, a polypeptide or protein modulator or cell expressing same is injected into an IVD, preferably, into a nucleus pulposus and/or adjacent to at least a portion of a nucleus pulposus and/or into a region of an IVD defined by an annulus fibrosus or into a region surrounding or adjacent to an IVD. Preferably, a polypeptide or protein modulator or cell expressing same or composition as described herein according to any embodiment is administered to a plurality of sites or locations or positions within an IVD, preferably within a nucleus pulposus and/or within a region of an IVD defined by an annulus fibrosus. Preferably, following a period of time sufficient to diffusion of the composition or modulator, the modulator or composition is distributed substantially uniformly or uniformly within an IVD and/or within a nucleus pulposus and/or within a region of an IVD defined by an annulus fibrosus. For example, a suitable route of administration is intradiscal administration, intrathecal administration or intraganglionic administration (see, e.g., TEXTBOOK OF PAIN, Wall and Melzack, Eds. Harcourt Brace, 4th Ed, 1999). One particularly useful method involves administering by discography as generally described by Carragee et al., *Spine* 24): 2542-2547, 1999.

In another example, a modulator of GDF-6 signaling or a composition as described herein according to any embodiment is administered by intradiscal injection or intradiscal implant.

In another example, a modulator of GDF-6 signaling is administered to or within an IVD and/or to or within a nucleus pulposus and/or adjacent to at least a portion of a nucleus pulposus and/or to or within a region of an IVD defined by an annulus fibrosus using a medical device as according to any embodiment hereof that comprises the GDF-6 signaling modulator or composition of the present invention such as, for example, in accordance with Example 9. For example, the GDF-6 signaling modulator can be administered to or within an IVD or to or within a nucleus pulposus and/or adjacent to at least a portion of a nucleus pulposus and/or to or within a region of an IVD defined by an annulus fibrosus by a process comprising:

accessing the region of the IVD such as by surgical intervention or by injection e.g., percutaneously using a cannula;

providing a medical device comprising a modulator of GDF-6 signaling or a composition of the present invention wherein the medical device comprises a delivery conduit having a proximal end attachable to a source of the GDF-6 signaling modulator or the composition and an emitter structure at a distal end of the delivery conduit, wherein the emitter structure defines a plurality of spaced discharge apertures through which the GDF-6 signaling modulator or composition is deliverable to the IVD or to the nucleus pulposus and/or adjacent to at least a portion of a nucleus pulposus and/or to the region of an IVD defined by an annulus fibrosus and wherein the emitter structure is configured to administer the GDF-6 signaling modulator or composition to a plurality of sites within the IVD and/or nucleus puplosus and/or region of the ND defined by the annulus fibrosus;

inserting the emitter structure of the medical device at least partially into the accessed region of the IVD;

manipulating the emitter structure so that the emitter structure at least partially surrounds or is positioned within the nucleus pulposus and/or region of the IVD defined by the annulus fibrosus and/or adjacent to at least a portion of a nucleus pulposus; and discharging the GDF-6 signaling modulator or composition through the apertures so as to administer the GDF-6 signaling modulator or composition to a plurality of sites within the ND and/or nucleus puplosus and/or region of the ND defined by the annulus fibrosus and/or adjacent to at least a portion of a nucleus pulposus, e.g., to promote diffuse and preferably uniform distribution of the GDF-6 signaling modulator or composition within the IVD and/or nucleus puplosus and/or region of the IVD defined by the annulus fibrosus and/or adjacent to at least a portion of a nucleus pulposus.

For example, the GDF-6 signaling modulator or composition of the present invention can be administered to or within an IVD or to or within a nucleus pulposus and/or to or within a region of an IVD defined by an annulus fibrosus and/or adjacent to at least a portion of a nucleus pulposus by a process comprising:

accessing the region of the IVD such as by surgical intervention or by injection e.g., percutaneously using a cannula;

providing a medical device comprising a modulator of GDF-6 signaling or composition of the present invention wherein the medical device comprises a delivery conduit having a proximal end attachable to a source of the GDF-6 signaling modulator or composition and an emitter structure at a distal end of the delivery conduit, wherein the emitter structure is at least partially receivable within an interior of the IVD and defining a plurality of spaced discharge apertures through which the GDF-6 signaling modulator or composition is delivered to a part of the ND, preferably to a nucleus pulposus and/or a region of an IVD defined by an annulus fibrosus and/or adjacent to at least a portion of a nucleus pulposus and wherein the emitter structure is configured to administer the GDF-6 signaling modulator or composition to a plurality of sites within the IVD and/or nucleus puplosus and/or region of the IVD defined by the annulus fibrosus and/or adjacent to at least a portion of a nucleus pulposus;

inserting the emitter structure of the medical device at least partially into the accessed region of the IVD;

manipulating the emitter structure so that the emitter structure at least partially surrounds or is positioned within the nucleus pulposus and/or region of the IVD defined by the annulus fibrosus and/or adjacent to at least a portion of a nucleus pulposus; and discharging the GDF-6 signaling modulator through the apertures so as to administer the GDF-6 signaling modulator or composition to a plurality of sites within the IVD and/or nucleus puplosus and/or region of the IVD defined by the annulus fibrosus and/or adjacent to at least a portion of a nucleus pulposus, e.g., to promote diffuse and preferably uniform distribution of the GDF-6 signaling modulator or composition within the IVD and/or nucleus puplosus and/or region of the IVD defined by the annulus fibrosus and/or adjacent to at least a portion of a nucleus pulposus.

In use, it is preferred to guide an emitter structure supra to the site of the IVD in an inoperative configuration and, when positioned at the site, to configure the emitter structure in an operative configuration to thereby at least partially surround or be positioned within a nucleus pulposus and/or region of the IVD defined by the annulus fibrosus. Thus, the emitter structure can be guided into its operative configuration.

It is also preferred to apply a substantially uniform flow rate of the GDF-6 modulator or composition through all of the apertures of the emitter structure.

The present invention further encompasses the performing of an annulotomy in an annulus of the IVD and distributing the GDF-6 modulator or composition to a plurality of sites or in a patterned manner within the disc, and/or the implanting a medical device comprising the GDF-6 modulator or composition. Implantations may be performed following a nucleotomy or without the need for a nucleotomy depending on the state of degeneration of the disc.

Preferred means for deploying the emitter structure include endoscopic visualization means and/or by fluoroscopic guidance techniques. As will be known to the skilled artisan, such techniques may require formulations of the GDF-6 signaling modulator that include at least one radio-opaque marker.

It is also preferred to substantially prevent back-flow of the GDF-6 signaling modulator or composition through the apertures in the emitter structure when delivery of the composition has been completed.

In the case of a nucleic acid modulator of GDF-6 signaling, the modulator or composition may be administered by particle bombardment or by liposome mediated delivery. Alternative methods for the delivery of nucleic acid modulators include, for example, microseeding (Erikkson et al., *J. Surg. Res.*, 78: 85-91, 1998), microfabricated needles (Henry et al., *J. Pharm. Sci.*, 87: 922-925, 1998), puncture mediated DNA transfer (Ciernik et al., *Hum. Gene Ther.*, 7: 893-899, 1996), lipid or liposome mediated delivery (Li et al., *In Vitro Cell Devel., Biol.*, 29A: 258-260, 1993; or Alexander et al., *Hum. Mol. Genet.*, 4: 2279-2285, 1995).

Alternatively, or in addition, a nucleic acid modulator is delivered by a viral-mediated process, e.g., an adenovirus or a retrovirus.

5. Dosage of Therapeutic GDF-6 Modulatory Composition

Selecting an administration regimen for a therapeutic composition depends on several factors, including the serum or tissue turnover rate of the entity, the level of symptoms, the immunogenicity of a modulator of GDF-6 signaling, and the accessibility of the target cells in the biological matrix. Preferably, an administration regimen maximizes the amount of therapeutic compound delivered to the patient consistent with an acceptable level of side effects. Accordingly, the amount of composition delivered depends in part on the particular entity and the severity of the condition being treated. Guidance in selecting appropriate doses of peptides are available (see, e.g., Milgrom, et al. *New Engl. J. Med.* 341:1966-1973, 1999; Slamon, et al. *New Engl. J. Med.* 344:783-792, 2001; Beniaminovitz, et al. *New Engl. J. Med.* 342:613-619, 2000; Ghosh, et al. *New Engl. J. Med* 348:24-32, 2003; or Lipsky, et al. *New Engl. J. Med.* 343:1594-1602, 2000).

In one example, a modulator of GDF-6 signaling is administered in a single bolus dosage. Alternatively, a peptide or polypeptide is provided, for example, by continuous infusion, or by doses at intervals of, e.g., one day, one week, or 1-7 times per week. Preferably, a modulator of GDF-6 signaling or a composition comprising said modulator is administered to a plurality of sites or in a patterned manner within an IVD, preferably within a nucleus pulposus or within a region of an IVD defined by an annulus fibrosus and/or adjacent to at least a portion of a nucleus pulposus. A preferred dose protocol is one involving the maximal dose or dose frequency that avoids significant undesirable side effects. A total weekly dose depends on the type and activity of the compound being used. For example, such a dose is at least about 0.05 µg/kg body weight, or at least about 0.2 µg/kg, or at least about 0.5 µg/kg, or at least about 1 µg/kg, or at least about 10 µg/kg, or at least about 100 µg/kg, or at least about 0.2 mg/kg, or at least about 1.0 mg/kg, or at least about 2.0 mg/kg, or at least about 10 mg/kg, or at least about 25 mg/kg, or at least about 50 mg/kg (see, e.g., Yang, et al. *New Engl. J. Med.* 349:427-434, 2003; or Herold, et al. *New Engl. J. Med.* 346:1692-1698, 2002).

An effective amount of a modulator of GDF-6 signaling for a particular patient may vary depending on factors such as the condition being treated, the overall health of the patient, the method route and dose of administration and the severity of side affects, see, e.g., Maynard, et al. (1996) A Handbook of SOPs for Good Clinical Practice, Interpharm Press, Boca Raton, Fla.; or Dent (2001) Good Laboratory and Good Clinical Practice, Urch Publ., London, UK.

Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects. Important diagnostic measures include those of symptoms of the disease and/or disorder being treated. Preferably, a compound that will be used is derived from or adapted for use in the same species as the subject targeted for treatment, thereby minimizing a humoral response to the reagent.

An effective amount of therapeutic will decrease disease symptoms, for example, as described supra, typically by at least about 10%; usually by at least about 20%; preferably at least about 30%; more preferably at least about 40%, and more preferably by at least about 50%.

The present invention is described further in the following non-limiting examples.

Example 1

Mutations in GDF-6 are Associated with Aberrant IVD Development 1.1 Materials and Methods
Subjects A large family of subjects suffering from an autosomal dominant form of Klippel-Feil Syndrome (KFS) was identified (designated KF2-01). The affected subjects had large block fusions of vertebrae within in the spine, or isolated cervical fusions, or fusions of cervical, thoracic and lumbar vertebrae, indicating that these subjects had aberrant IVD development.

FISH Chromosome Inversion Analysis

Cytogenetic analyses of the KF2-01 family indicated the presence of inversion breakpoints located on 8q22.2 and 8q23.316. From the National Center for Biotechnology Information (NCBI) database a contiguous array of bacterial artificial chromosome (BAC) clones from the genomic regions flanking the inversion were selected. FISH chromosome analysis was performed as follows: metaphase spreads were prepared from PHA-stimulated lymphocytes, cultured at 37° C. for 72 hr. High resolution analysis of elongated chromosomes was carried out using dual-colour fluorescence. Total DNA isolated from BAC clones (Invitrogen, Australia) was nick-translated using fluorescent labelled dUTP (spectrum green and spectrum red, Vysis Inc.). Hybridization to metaphase chromosomes was performed essentially as described in Pinkel et al., *Proc. Natl Acad. Sci. USA*, 83: 2934-2938, 1986. For each slide, 400 ng of fluorescent labelled DNA was used. Before hybridization, the labelled probe was annealed with a 400-fold excess amount of Cot-DNA (Immunodiagnostics Pty Ltd, Australia) at 37° C. for 45 min. Chromosomes were counterstained with DAPI or propidium iodide diluted in anti-fade solution pH8. Fifty metaphases were analysed for each hybridization. Images were captured and merged using an Imstar digital FISH imaging system (Immunodiagnostics, Australia).

Inversion Breakpoint Analysis

The FISH screening strategy was based on the principle that any BAC clone/probe which spanned a breakpoint would display a split/dual hybridization signal. Two BAC clones (AC026561 and AC012238) were identified from either end of the inversion that gave split signals. To clone the proximal inversion breakpoint a set of forward PCR primers were designed at 5-kb intervals across the region of interest in each breakpoint BAC (AC026561 and AC012238), respectively. The forward primers from both BACs were combined to yield a unique PCR amplification product from patient DNA which contained the proximal inversion breakpoint. Primers used to amplify the proximal inversion breakpoint from affected KF2-01 family members were: 1F primer 5'-ATCCCTTAGT-TGAACACAAAAAGCACAAGC-3' (from BAC AC026561) (SEQ ID NO: 10) and the 2F primer 5'-TTC-TATAAAGATCATCCATGCTAAACACTG-3' (from BAC AC012238) (SEQ ID NO: 11). To clone the distal inversion breakpoint this PCR protocol was repeated using a mixed reverse primer set comprising: 1R primer 5'-TGTAT-GAGAGTTTTGGTGGTTCCACATC-3' (SEQ ID NO: 12), and 2R 5'-GATAAGGACTGAGATATGCCCTGGT-3' (SEQ ID NO: 13).

Long-range breakpoint PCR was performed in a 25 μl reaction mixture containing 50 ng of genomic DNA, 0.2 μM of each primer, 200 μM dNTPs, and 1 U Elongase enzyme (Life Technologies). An initial 3 min denaturation step at 95° C.; 32 cycles of denaturation at 95° C. for 30 s, annealing at 60° C. for 30 s and extension at 72° C. for 7 min; followed by a final extension at 68° C. for 3 min. PCR products were purified using QIAquick Spin PCR purification kit (QIAGEN) before sequencing.

DNA Sequencing

DNA sequencing was performed using the ABI Big Dye Terminator version 3.1 cycle sequencing kit essentially according to manufacturer's instructions (i.e. 5 ng (5 μL) purified PCR amplicon, 4 μL reaction pre-mix, 2 μL 5× sequencing buffer, 3.2 pmol (2 μL) appropriate primer and 7 μL deionized water were added in a 96-well microtiter plate. The plate was transferred to a PCR thermocycler (MJ Research PTC-200) and cycled at: 96° C. for 1 min; 25 cycles at 96° C. for 10 s, 50° C. for 5 s and 60° C. for 4 min. Sequencing products were purified using ABI Centri-Sep spin columns. Resuspended samples were resolved on an ABI 377 DNA sequencer, essentially according to the manufacturer's instructions and sequences analyzed using the BioEdit biological sequence alignment editor (v 5.0.9.1; Tom Hall, Isis Pharmaceuticals).

Mutation Screening

The 2 exons of GDF6 were screened by automated sequencing, including at least 50 bp into the intron boundaries. The transcription start codon resides in exon 1. Primers were designed using the Primer3 program and were synthesised by Invitrogen Australia. PCR was performed in a 25 μl, reaction mixture containing 50 ng genomic DNA, 0.2 μM of each primer, 200 μM dNTPs in 1×PCR buffer with 5% DMSO and 0.25 U Taq polymerase (Promega). Before thermal cycling, samples were denatured at 95° C. for 4 min followed by five touch down cycles of 95° C. for 40 s denaturation, 65° C. for 40 s annealing and 72° C. for 50 s extension; then 28 cycles of 95° C. for 40 s denaturation, 60° C. for 40 s annealing and 72° C. for 50 s extension with a final extension at 72° C. for 10 min (Corbett Research CG1-96). PCR products were resolved by electrophoresis in 1.4% agarose gels and purified using the Promega Wizard gel purification system before bi-directional sequencing.

Protein Sequence Alignment

Sequence alignments were carried out using ClustalW software. Proteins from aligned species included *Homo sapiens, Macaca mulatta, Mus musculus, Rattus norvegicus, Xenopus laevis, Danio rerio* and *Tetraodon nigroviridis*. GDF6 secondary structure was predicted for GDF6 using PROF 19. The cysteine knot was prepared in comparison with GDF520 using PyMOL graphics system (Delano Scientific USA).

Analysis of Conserved Noncoding Sequences (CNSs)

To determine if any conserved DNA elements were located in the breakpoint region a comparative analysis of genomic sequences from multiple species was performed. The breakpoint occurs between GDF6 (630-kb 3') and C8orf37 (hypothetical protein LOC157657) (180-kb 5'). The genomic sequence in the interval between GDF6 and C8orf37 were extracted from the Ensembl and NCBI GenBank databases for human, chimpanzee, dog, mouse, rat, chicken, and opossum and analysis for CNSs using VISTA software with the human sequence as the reference sequence (Frazer et al., *Nucl. Acid Res.*, 32: W273-279, 2004).

A CNS was defined to be 100 bp ungapped alignment with at least 70% identity. The human gene annotation was obtained from the Ensembl database and the repeat information was obtained from RepeatMasker.

Tissue Collection

The nucleus pulposus (NP) and out region of the annulus fibrosus (AF) were collected fresh from 1 subject (age 16) undergoing a lumbar total disc replacement surgery.

One normal Spraugue-Dawley male rat weighting 380 g was anesthetised and humanly sacrificed before the lumbar spinal disc and vertebrae were immediately dissected.

Immunohistochemistry of Human and Rat Vertebrae

All tissue specimens were immediately fixed in 10% neutral buffered formalin for 5 hour and washed with PBS followed by embedding in paraffin. Animal disc tissue was decalcified (RDO solution, Lomb Scientific Australia) for 24 h. 4 μM mid-sagittal serial sections were cut and mounted on Super Plus slides (Lomb Scientific). Hematoxylin-eosin (H&E) staining was performed for general histological examinations. For Alcian blue staining (proteoglycan), and Safranin-O staining (newly deposited matrix), serial sections were de-waxed in xylene and re-hydrated through graded ethanol and stained in Alcian blue solution (1% W/V, pH 4.2) or Safranin-O for 15 min. Nuclei were counter stained with nuclear red solution.

For immunohistochemical staining, slides were deparaffinized and hydrated through graded ethanol and equilibrated in Tris-HCl (pH 7.6) buffer. Antigen retrieval was achieved using DAKA Target Retrieval Solution. Endogenous peroxidase activity was quenched with 3% (v/v) $H_2O_2$ and nonspecific binding blocked with 10% skimmed milk powder in Tris buffered HCl. Primary rabbit anti-human GDF-6 polyclonal (GDF6) (1:500 dilution, Alpha Diagnostic Int.) was incubated on the slides for 1 hour at room temperature, washed and treated with MULTILINK solution (DAKO, Australia) followed by incubation with streptavidin conjugated peroxidase. The sections were visualized with 3,3'-diaminobenzidine hydrochloride solution (DAB, DAKO) and counterstained with Haematoxylin. Negative controls were treated in a similar manner.

1.2 Results

Inversion Breakpoint Localized within GDF6 Locus

To identify the location of breakpoints on 8q22.2 and 8q23.316 in KFS subjects FISH chromosome analysis using chromosome 8 specific BAC probes was performed. Two BACs (AC026561 and AC012238) were identified that spanned the respective breakpoints which gave unique split hybridization signals on chromosome 8q (confirmed in twenty metaphases). Breakpoint specific PCR screening verified cosegregation of the inversion with the disease phenotype in twenty affected and four unaffected KF2-01 family members. Breakpoint PCR amplicons were sequenced and the proximal and distal breakpoints identified at nucleotide position 96544749 and 116078713, respectively, on chromosome 8q. The full length of the inverted segment was 19,533,963 bp. No additional rearrangement or DNA loss was associated with either breakpoint. Both inversion breakpoints were localized within extensive intergenic regions significant distances from neighbouring genes.

The distal breakpoint occurred within an intergenic region 1.6 Mb 5' from CSMD3 and 400 kb 3' from the TRPS1 human disease gene. CSMD3 is expressed predominantly in fetal brain24, and TRPS1 mutations are causative in trichorhinophalangeal syndrome type I. The TRPS1 gene was not disrupted by the inversion. TRPS1 patients with previously characterized deletions in this same region 3' of the TRPS1 gene did not present with KFS-like phenotypes (Ludecke et al., *Am. J. Hum. Genet.*, 68: 81-91, 2001).

The proximal KF2-01 inversion breakpoint also occurred within an intergenic region 180 kb 5' of transcript C8orf37 (hypothetical protein LOC157657) and 630 kb 3' of GDF6. C8orf37 is a transcription unit of unknown function and GDF6, a member of the BMP family of secreted signalling molecules, is implicated in skeletal development. This genomic region between GDF6 and C8orf37 is known to harbor GDF6 long range enhancer elements (Mortlock et al., *Genome Res.*, 13: 2069-2081, 2003). Regions rich in conserved non-coding sequences adjacent to the breakpoint were identified. With the exception of GDF6, no other genes located adjacent to the KF2-01 inversion breakpoints have recognised developmental or biological roles or known expression patterns which overlap with the KF2-01 familial phenotype.

GDF6 expression was also observed within nucleus pulposus cells of both rat and human adult IVDs (FIG. 1). As a strong candidate for KFS, GDF6 was subsequently screened for mutations in our large cohort of patients.

GDF6 Missense Mutations in KFS Patients

GDF6 coding regions and associated exon splice sites were sequenced in 105 patients with de novo or inherited cases of KFS. Two new polymorphisms were identified in both the KFS and control populations screened; c.506+28C>A and c.1036G>C (p.SER312SER) at a frequency of approximately 4% of the population tested. Two different missense mutations were identified in three unrelated cases of KFS. In each case, the mutation was not detected in 174 controls (i.e. 348 chromosomes tested) giving ~95% power to distinguish a normal sequence variant from a mutation (Collins et al., *Am. J. Hum. Genet.*, 71: 1251-1252, 2002. None of the base substitutions found was present in the NCBI dbSNP database.

GDF6A249E Missense Variant

A heterozygous (c.846C>A) missense mutation segregating with KFS patterns of vertebral fusion (always inclusive of the C2-3 fusion) was also identified. The mutation (c.846C>A) in exon 2 resulted in the substitution of glutamic acid for alanine 249 (GDF6A249E) within the GDF6 prodomain. The GDF6A249E missense variant segregated with the KFS phenotype in the family and was absent from unaffected family members and ethnically matched normal controls.

Recurrent GDF6L289P Missense Variant

A recurrent heterozygous missense mutation c.966T>C was identified in two unrelated patients with sporadic KFS. Sequencing identified a recurrent missense mutation (c.966T>C) in exon 2 which resulted in the substitution of leucine for proline at position 289 GDF6L289P.

The missense mutations identified in the present study both cause amino acid changes in a region of GDF6 that is predicted to be required for GDF6 homodimerization and/or heterodimerization and, as a consequence GDF-6 signaling. Accordingly, these results indicate that disruption of GDF-6 signaling results in KFS syndrome, and, as a consequence aberrant IVD development and/or maintenance. This is supported by the persistence of GDF6 expression in the nucleus pulposus cells of the adult vertebral disc (FIG. 1) may indicate an extended role for GDF6 in disc maintenance.

Example 2

Over Expression of MSX-1 or MSX-2 in IVD Cells Induces Collagen Formation and Extracellular Matrix Formation 2.1 Materials and Methods Nucleus Pulposus Cultures Nucleus pulposus tissue were visually separated from annulus fibrosus and aseptically procured from a cadaveric sheep spine (2 years of age) into sterile saline. Tissues were cut into ~1 mm$^2$ pieces and then digested overnight with 0.025% collagenase solution in a shaking incubator at 37° C. Isolated cells were grown in 10% fetal calf serum (FCS) with 1% antibiotics (P/S/F) in DMEM (Invitrogen, Carlsbad, Calif.) culture media until confluency.

Lipofectamine Transfection

Transfection was performed with either 80 ng or 240 ng of an expression vector including a nucleic acid encoding MSX1 or MSX2 with an empty expression vector premixed with 18 μl Lipofectamine 2000 in Opti-MEM (Invitrogen) using 6-well plates (3×10$^5$ cells per well for six wells), essentially according to manufacturer's instructions. At two days post-transfection, cells were selected and maintained with 600 μg G-418 Sulfate (Invitrogen) per ml of culture media.

Relative quantitation of MSX1 or 2 activity was determined using a MSX1/2 ELISA$^{PLUS}$ Kit essentially according to manufacturer's instructions. Relative activity was determined by the following calculation: $[((Abs_{sample}-Abs_{heat\ inactivated\ sample})/Abs_{internal\ standard})/((Abs_{positive\ control}-Abs_{lysis\ buffer})/Abs_{internal\ standard})]\times 100$.

Cell Viability Assay

Cell survival was measured with MTS Cell Proliferation Assay kit (Promega, Madison, Wis.) using cells (1×10$^4$)/well plated in 96 well plates. Assays were performed as specified by the manufacturer where only viable cells are able to metabolically reduce tetrazolium salts to formazan salts, detected directly on a spectrophotometer at 490 nm Collagen Synthesis Collagen synthesis was assessed by [3H]-proline incorporation. L-[2, 3-3H] Proline (Perkin Elmer, Sydney Australia) was added to culture medium at a concentration of 2 μCi/200 μL media. Cells were incubated for 24 hours. Cells were then harvested after washing with 95% ethanol and PBS. Radioactivity of cells was counted in a liquid scintillation counter.

Proteoglycan Synthesis

Proteoglycan synthesis was assessed by [35S]-sulfate incorporation. [35S]-sulfate (Perkin Elmer, Sydney Australia) was added to cell cultures at 2 μCi per well and allowed to incubate for 24 hours. Cells washed with 95% ethanol and PBS and harvested. Radioactivity of the cells was counted in a liquid scintillation counter as a representative of proteoglycan synthesis.

2.2 Results

Anulus fibrosus cells or nucleus pulposus cells were isolated from sheep IVDs and cultured for three passages. Following this period cells were transfected with an expression vector expressing MSX-1 or MSX-2 under control of the CMV promoter or a control vector (empty expression vector). Cells were transfected with two different concentrations of expression vector (i.e., 80 ng or 240 ng).

Figure 2:
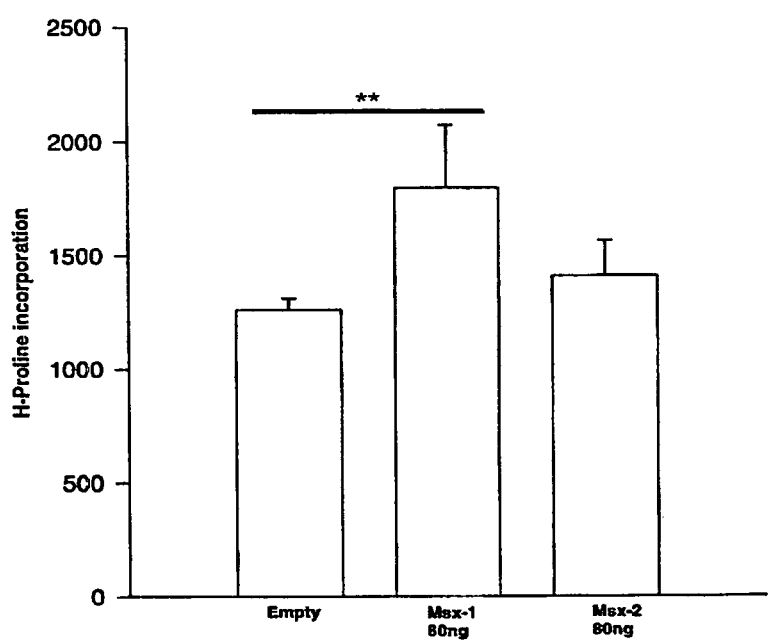
FIG. 2 is a graphical representation showing the level of H-proline incorporation into annulus fibrosus cells transfected with 80 ng of a vector expressing MSX-1 or MSX-2 or an empty vector (control). H-proline incorporation is indicative of collagen synthesis. Cells transfected with MSX-1 show significantly increased H-proline incorporation than control cells. **, p<0.01
Figure 3:
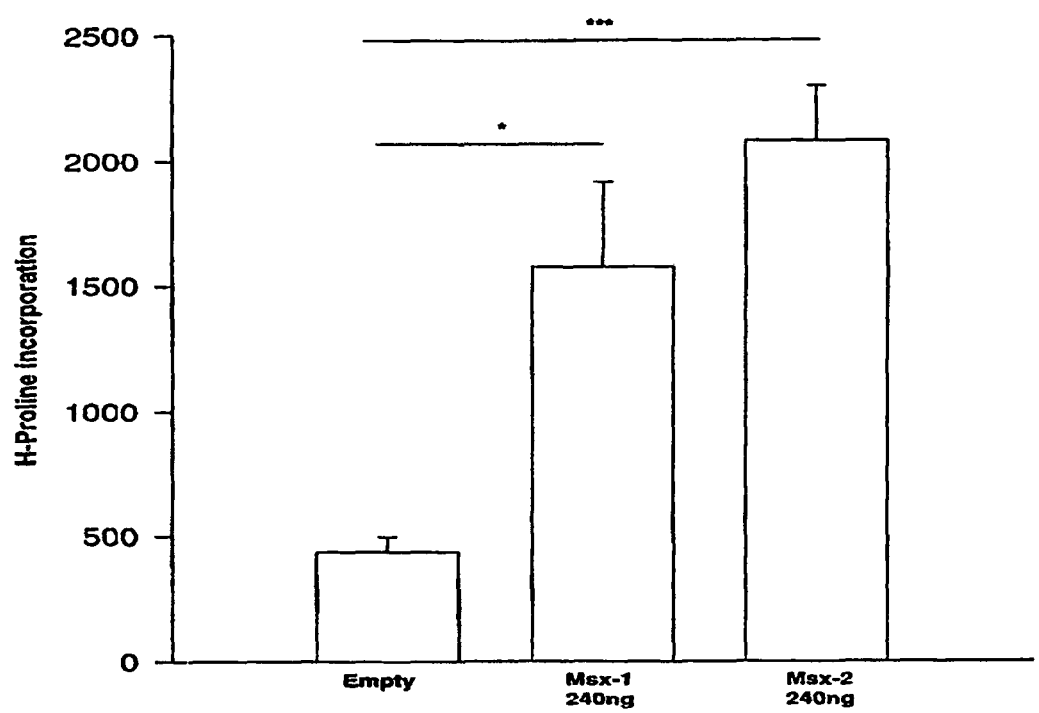
FIG. 3 is a graphical representation showing the level of H-proline incorporation into annulus fibrosus cells transfected with 140 ng of a vector expressing MSX-1 or MSX-2 or an empty vector (control). Cells transfected with MSX-1 or with MSX-2 show significantly increased H-proline incorporation than control cells. *, p<0.05; ***, p<0.001.

Following a suitable period for the introduced nucleic acids to be expressed, cells were assayed for collagen production, by determining the level of incorporation of H-proline into cells. As shown in FIG. 2, at the 80 ng dosage level, MSX-1 induced a significant increase in collagen synthesis in anulus fibrosus cells. At the 240 ng dosage, both MSX-1 and MSX-2 induced a significant increase in collagen synthesis in annulus fibrosus cells compared to control cells (FIG. 3).

Figure 4:
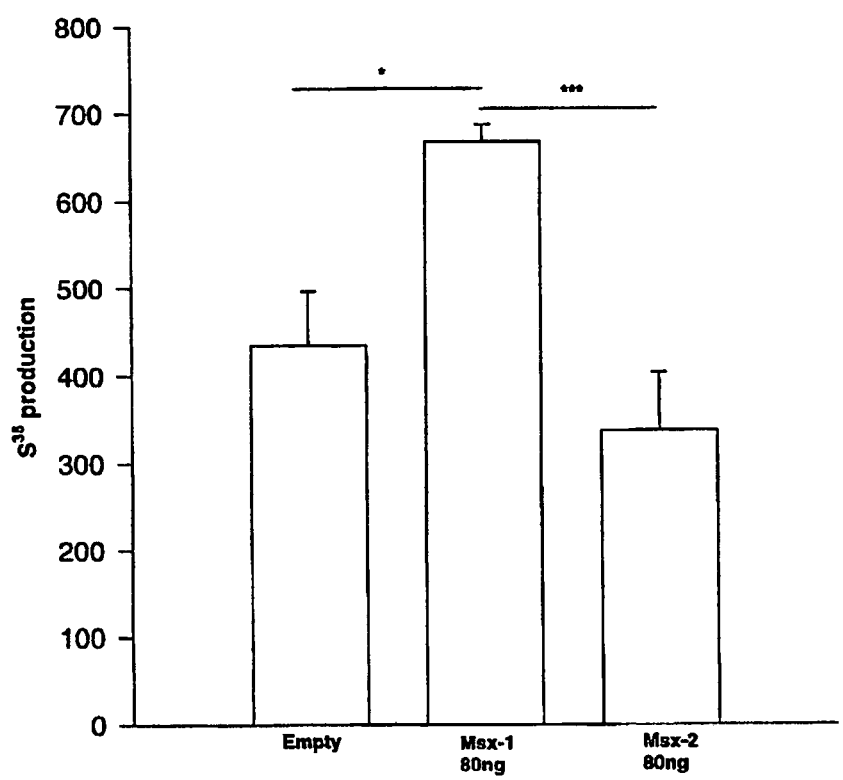
FIG. 4 is a graphical representation showing the level of $^{35}S$ incorporation into extracellular matrix produced by annulus fibrosus cells transfected with 80 ng of a vector expressing MSX-1 or MSX-2 or an empty vector (control). Cells transfected with MSX-1 show significantly increased $^{35}S$ incorporation than control cells. *, p<0.05; ***, p<0.001.
Figure 5:
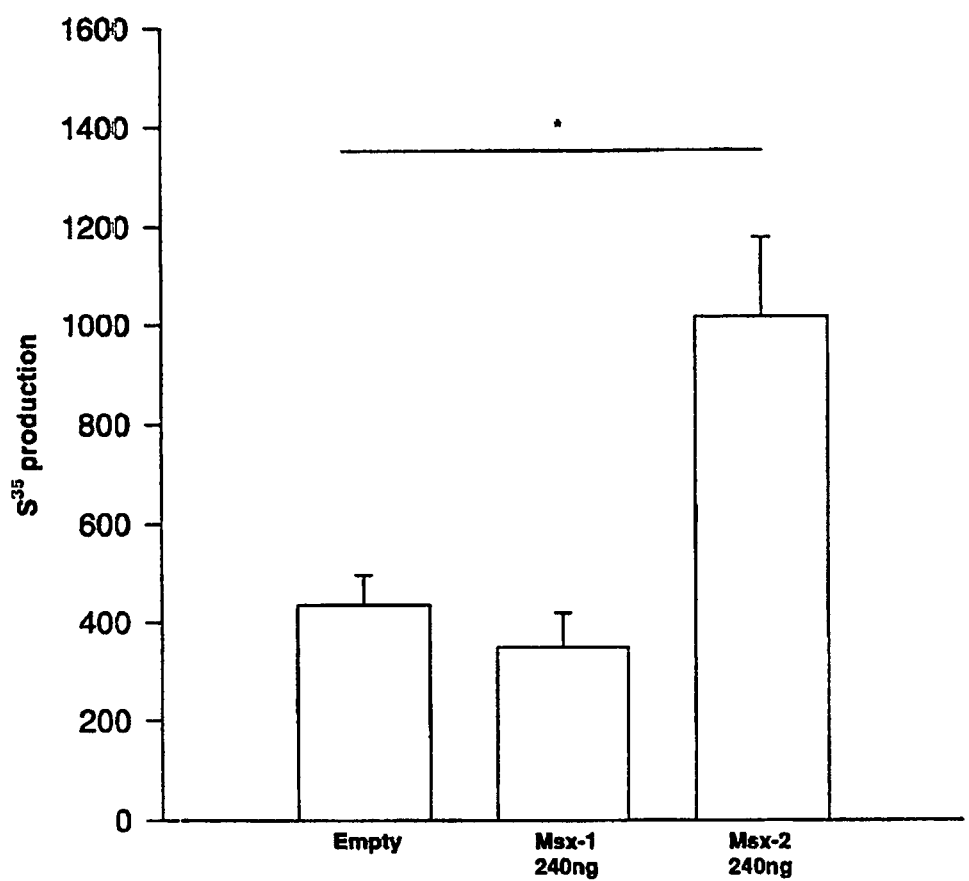
FIG. 5 is a graphical representation showing the level of $^{35}S$ incorporation into extracellular matrix produced by annulus fibrosus cells transfected with 140 ng of a vector expressing MSX-1 or MSX-2 or an empty vector (control). Cells transfected with MSX-2 show significantly increased $^{35}S$ incorporation than control cells. *, p<0.05.

Cells were also assayed to determine the level of extracellular matrix production, be determining the level of $^{35}$S incorporation into a culture. As shown in FIG. 4, 80 ng of nucleic acid encoding MSX-1 significantly increased extracellular matrix production compared to control cells. Moreover, 240 ng of nucleic acid encoding MSX-2 significantly increased the level of extracellular matrix production above control cells (FIG. 5).

Figure 6:
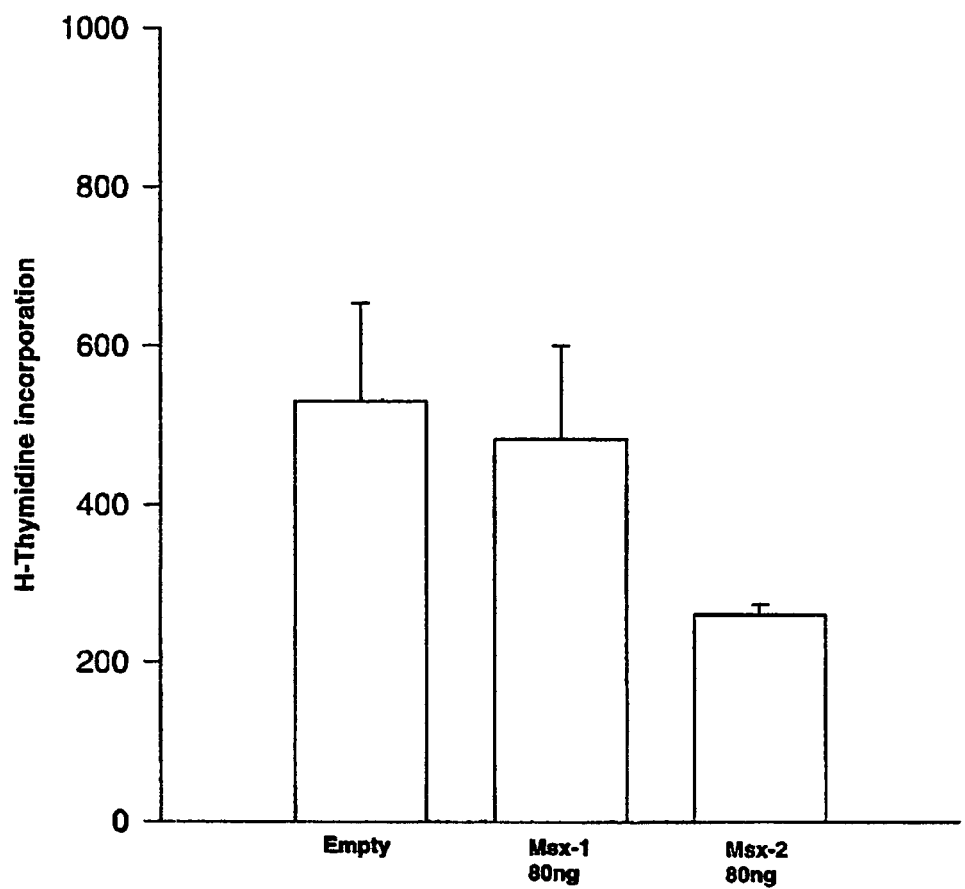
FIG. 6 is a graphical representation showing the level of H-thymidine incorporation (indicative of cell proliferation) in annulus fibrosus cells transfected with 80 ng of a vector expressing MSX-1 or MSX-2 or an empty vector (control). MSX-1 and MSX-2 do not significantly alter H-thymidine incorporation.
Figure 7:
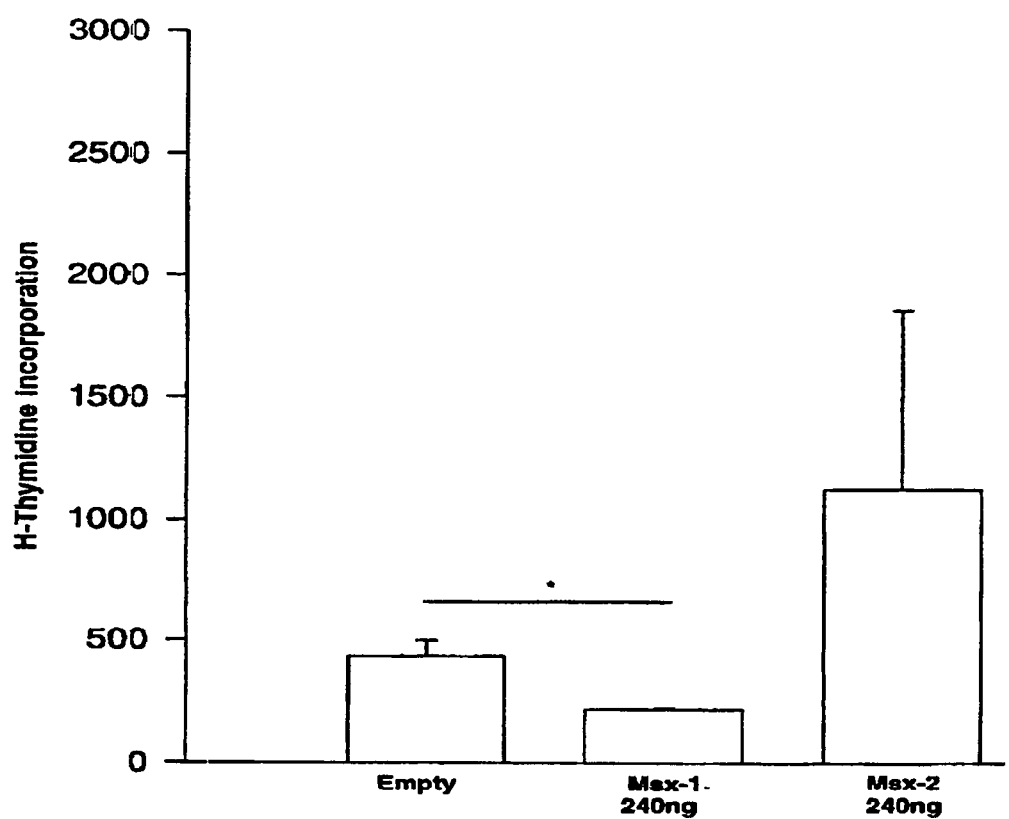
FIG. 7 is a graphical representation showing the level of H-thymidine incorporation in annulus fibrosus cells transfected with 140 ng of a vector expressing MSX-1 or MSX-2 or an empty vector (control). MSX-1 and MSX-2 do not significantly alter H-thymidine incorporation.

As shown in FIGS. 6 and 7, ectopic expression of MSX-1 or MSX-2 did not significantly alter the incorporation of H-thymidine by transformed cells, i.e., did not increase cell proliferation in annulus fibrosus cells.

These results indicate that MSX-1 and/or MSX-2 are capable of inducing changes in IVD cells associated with IVD regeneration.

Example 3

Additional Characterization of Cells Over Expressing MSX1 or MSX2

3.1 Cell Cultures

Sheep nucleus pulposus cells are produced as described in Example 2

Human nucleus pulposus cultures are produced by collecting nucleus pulposus from eight subjects undergoing lumbar total disc replacement surgery (age: 48±16 years). All discs demonstrate moderate signs of disc degeneration on MRI including decreased water content and a decrease in disc height. Discarded nucleus pulposus tissues are immediately subjected to 0.025% collagenase digestion overnight. Primary cultures are grown in a complete medium containing DMEM (Invitrogen, Carlsbad, Calif.) 10% fetal calf serum, 1% penicillin/streptomycin for 10-12 days to become confluent. Cells are subcultured at concentration of $1 \times 10^5$/ml for 2-3 days before treatment. All experiments are completed using the second passages of cells.

Cells are transfected and analyzed essentially as described in Example 2.

3.2 Extracellular Matrix mRNA Detection

RNA extraction from pooled aliquots of six flasks for each of control and transfected cells is performed with RNeasy Mini Kit (Qiagen, Hilden, Germany) and concentrated with a vacuum centrifuge. RNA is digested with DNase I Amplification Grade (Invitrogen) prior to the ImProm-II™ Reverse Transcription System (Promega, Madison, Wis.) for the generation of cDNA using Oligo(dT)$_{15}$ primers and 6.3 mM MgCl$_2$ per reaction essentially in accordance with manufacturer's instructions.

Expression levels of collagen Type 1, Collagen Type 2, Aggrecan and GAPDH is determined using the following primers: Collagen Type-1: [Forward] AGACATCCCAC-CAATCACCT (SEQ ID NO: 14) [Reverse] AGATCACGT-CATCGCACAAC (SEQ ID NO: 15); Collagen Type-2: [Forward] AACACTGCCAACGTCCAGATG (SEQ ID NO: 16); [Reverse] TCGTCCAGATAGGCAATGCTG (SEQ ID NO: 17); Aggrecan: [Forward] ACGTGATCCTCACGGCAAA (SEQ ID NO: 18); [Reverse]GTGAAAGGCTCCTCAGGT-TCTG (SEQ ID NO: 19); GAPDH: [Forward] ACCCAGAA-GACTGTGGATGG (SEQ ID NO: 20) [Reverse] AGAG-GCAGGGATGATGTTCT (SEQ ID NO: 21). Real time reactions are performed in triplicates with Platinum® Syber® Green qPCR SuperMix UDG (Invitrogen) using a Rotor-Gene Thermal cycler (Corbett Research, Sydney, Australia) programmed for: 50° C., 95° C. for 2 min hold each, 50 cycles of (94° C., 30 sec; 60° C., 30 sec with a 1° C. drop per cycle for the first five cycles; 73° C., 1 min). Gene expression of transfected cells relative to controls is analyzed using the relative expression software tool (RES©) [Pfaffl 02]. Statistical significance is determined by the pair wise fixed reallocation randomization test provided with the software.

3.3 Western Blot Analysis

The cells are harvested in lysis buffer containing a protease inhibitor cocktail (500 µg/ml AEBSF and 1 µg/l E-64, leupeptin, pepstatin-A at 2 µg/ml each). Protein (20-40 µg) is resolved on a 7.5% or 12% (v/v) SDS-PAGE gel. Proteins are transferred onto a PVDF membrane. Subsequently the membrane is probed with goat anti-Collagen-II polyclonal antibody (1:500, Santa Cruz Biotechnology), or anti-caspase-3 monoclonal antibody or anti-cleaved caspase-3 monoclonal antibody (1:1000 and 800, Cell Signalling technology) for 60 minutes. Membranes are then washed prior to addition of the corresponding secondary antibody conjugated with peroxidase (Chemicon, Temecula, Calif.) at a 1:1000 dilution for 30 minutes. A chemiluminescence detection system (Pierce) is then used for the visualisation of labeled proteins. Blots are stripped and re-probed with mouse anti-β-Actin monoclonal antibody (1:10000, Sigma) to ensure equal amounts of protein are loaded per lane. Visualized bands are semi-quantified by densitometry (Model GS-700/690, Bio-Rad, Hercules, Calif., USA).

3.4 Immunofluorescence Staining (Collagen-II and Aggrecan)

Immunofluorescence staining is performed after fixation with 4% paraformaldehyde of cells cultured on glass cover slips. Non-specific binding is then blocked with 5% normal donkey or sheep serum for 30 minutes. Primary goat anti-collagen type-II polyclonal (1:200) or mouse anti-human aggrecan monoclonal antibodies (1:150, Chemicon) are incubated on individual slides for 1 hour. Cells are repeatedly washed and secondary antibodies; donkey anti-goat or sheep anti-mouse IgG conjugated with FITC (Chemicon) is applied at 1:500 dilutions. Cells on mounted cover-slip are visualized using a fluorescence microscope (Leitz, Wetzlar). Negative controls are treated in a similar manner but with the omission of primary antibody and are consistently included in each experiment.

3.5 Alkaline Phosphatase Production

To ensure that MSX-1 or MSX-2 over expression results in the production of disc cells and not in the production of bone cells, Alkaline phosphatase (AP) activity is determined by lysing cells with 0.1% Triton X-100 in PBS buffer and lysates were then incubated for 30 minutes at 37° C. with the AP substrate, p-nitrophenylphosphate (Sigma-Aldrich) at 2.5 µg/ml. The levels of p-nitrophenol (PNP) production were measured by a spectrophotometer and concentrations were determined by comparison with a standard curve created with known amounts of p-nitrophenol. AP activity is expressed as nanomoles of PNP generated per microgram of total cellular protein per minute.

3.6 Proteoglycan Synthesis

Cell cultures were maintained in complete medium containing 10 µCi/ml of [$^{35}$S]-sulfate (Amersham Biosciences Corp., Australia) for 8 hours.

Proteoglycans were extracted from cells or medium with 4 M guanidinium hydrochloride (in 50 mmol sodium acetate pH 5.8 containing 0.1 M 6-amino-hexanoic-acid, 50 mmol benzamidine HCl, 10 mmol EDTA, and 5 mmol N-ethylmaleimide) at 4° C. for 24 hours. Total synthesis was determined by combining radioisotope incorporation of both the cells and condition medium using a rapid filtration assay (essentially as described in Masuda et al., *Anal Biochem*, 217: 167-175, 1994). Proteoglycans (PG) were precipitated by alcian blue (Sigma). The newly synthesized proteoglycans was detected by using a [beta]-liquid scintillation counter. Rates of [$^{35}$S]-incorporation were expressed as nmols [$^{35}$S]-incorporated/µg DNA.

Example 4

In Vivo Models of IVD Degeneration 4.1 Rabbit Model

Adolescent New Zealand white rabbits (weighing 3.5-4 kg) are anaesthetized and two non-contiguous discs (L2/3 and L4/5) are punctured with an 18G needle using a left retroperitoneal approach, to induce disc degeneration. Four weeks later, eight rabbits were sacrificed for baseline assessments of the annular puncture.

4.2 Sheep Model

Sheep are fasted for 24 hours prior to surgery and then anaesthetized. A lateral plain X-ray is taken to verify normal lumbar spine anatomy. A skin incision is made on the left side immediately anterior to the transverse processes of the spine and the lumbar spine exposed by blunt dissection using an anterior muscle-splitting technique. Sheep will receive controlled annular lesions in their L1-L2, L3-L4 and L5-L6 discs by incision through the left anterolateral annulus fibrosus parallel and adjacent to the cranial endplate using a scalpel blade to create a lesion measuring approximately 4 mm long and approximately 5 mm deep. The intervening lumbar discs (L2-L3, L4-L5) will not be incised. A non-operated disc remains between treated discs to allow for adequate anchorage of FSUs in subsequent mechanical testing. A wire suture will be used to identify the craniad operated level for later identification purposes both in X-rays and for morphological identification.

Three months after induction of the annular lesions the sheep will be killed and the lumbar spines will be radiographed to evaluate disc calcification, excised and processed for biomechanical and histochemical analyses, and, after the biomechanical testing the same discs zonally dissected for compositional analyses.

Example 5

Treatment of IVD Degeneration with Recombinant GDF-6

5.1 Administration of GDF-6 to Animals

Recombinant human GDF-6 is obtained from a commercial source, such as, for example, US Biological, MA, USA.

Animal models as described in Example 4 are treated with recombinant GDF-6. For example, incised discs receive one of three therapies administered using a standard needle or essentially as described in Example 9 hereof, (I) no treatment, (II) lactose solution or (III) lactose containing GDF-6. In all animals the L3-L4 disc receives an annular lesion with no treatment. In one group of animals the L1-L2 discs are treated with lactose solution only and the L5-L6 disc are treated with lactose plus GDF-6. In another group of animals the treatments in the L1-L2 and L5-L6 discs are reversed to avoid any potential outcome bias associated with spinal level.

5.2 Radiological and MRI Assessments

Disc height is radiographically monitored biweekly from the day of administration of the above-treatment to 24 weeks post-administration. Intervertebral height is expressed as the disc height index (DHI) (Percent DHI (% DHI=(postoperative DHI/preoperative DHI)×100). At 4-, 8-, 12- and 24-weeks after injection, an MRI of the spinal column is taken to grade the level of degeneration based on modified Thompson grade (MRI, 1=normal, 4 severely degenerated) (Masuda et al., Spine 30:5, 2004)

5.3 Proteoglycan and Collagen Contents of Disc Tissues

Samples of annulus fibrosus and nucleus pulposis are diced over ice and representative portions of each tissue zone of known wet weight is freeze dried to a constant weight. The difference between the starting and final weights of the tissues is indicative of water content of the tissue. Triplicate portions (1-2 mg) of the dried tissues are hydrolyzed in 6M HCl at 110° C. for 16 h and aliquots of the neutralized digests assayed for hydroxyproline as a measure of the tissue collagen content (essentially as described in Melrose et al., J Orthop Res 10:665-676, 1992; and Melrose et al., Matrix 14:61-75, 1994. Triplicate portions of dried tissues are digested with papain and aliquots of the solubilized tissue assayed for sulphated glycosaminoglycan using the metachromatic dye 1,9-dimethylmethylene blue as a measure of tissue proteoglycan (see Melrose et al., 1992 and 1994, supra).

5.4 Histochemical and Immunohistochemical Analyses

Spinal motion segments that are designated for histochemical analysis are isolated by cutting through the cranial and caudal vertebral bodies close to the cartilaginous endplates. Entire disc specimens including the adjacent vertebral body segments are fixed en bloc in either 10% neutral buffered formalin or Histochoice™ for 56 h and decalcified in several changes of 10% formic acid in 5% NBF for 2 weeks with constant agitation until complete decalcification is confirmed using a Faxitron HP43855A X-ray cabinet (Hewlett Packard, McMinnville, USA).

Sagittal slices (5 mm thick) of the decalcified disc-vertebral body specimens are dehydrated through graded ethanol solutions by standard histological methods and embedded in paraffin wax. Paraffin sections 4 µm thick are prepared for histochemical staining and mounted on Superfrost Plus glass microscope slides (Menzel-Glaser) and dried.

Sections are deparaffinized in xylene and rehydrated through graded ethanol washes (100-70% v/v) to water.

Sections from all blocks are stained with haematoxylin and eosin. These sections are examined by a histopathologist who compares the histological characteristics of those levels that receive annular incision only with those that are incised and receive GDF-6. A four-point semi-quantitative grading system is used to assess the microscopic features. Collagen architecture is also examined in sections stained with Masson's trichrome and picro-sirius red using polarized light microscopy.

For immunohistochemistry endogenous peroxidase activity is blocked by incubating the tissue sections with 3% $H_2O_2$. Tissue sections are then treated with combinations of chondroitinase ABC (0.25 U/ml) in 20 mM Tris-acetate buffer pH 8.0 for 1 h at 37° C., bovine testicular hyaluronidase 1000 U/ml for 1 h at 37° C. in phosphate buffer pH 5.0, followed by washes in 20 mM Tris-HCl pH 7.2 0.5M NaCl (TBS) or proteinase-K (DAKO S3020) for 6 min at room temperature to expose antigenic epitopes. The tissues are then blocked for 1 h in 20% normal swine serum and probed with a number of primary antibodies to large and small proteoglycans and collagens, Aggrecan, Perlecan, Versican, Decorin, Biglycan, Fibromodulin, Collagen Type I, Collagen Type II, Collagen Type IV, Collagen Type VI and Collagen Type X. Negative control sections are also processed either omitting primary antibody or substituting an irrelevant isotype matched primary antibody for the authentic primary antibody of interest. Horseradish peroxidase or alkaline phosphatase conjugated secondary antibodies are used for detection using 0.05% 3,3'-diaminobenzidene dihydrochloride and 0.03% $H_2O_2$ in TBS or Nova RED substrates. The stained slides are examined by bright-field microscopy and photographed using a Leica MPS 60 photomicroscope digital camera system.

5.5 Biomechanical Assessment of Spinal Motion Segments

Non-destructive biomechanical range of motion (ROM) analysis is conducted on each functional spinal unit (FSU) in various planes of motion (flexion-extension, lateral bending, compression and torsion). Each FSU comprises two adjacent vertebrae, the intervening disc and associated ligaments.

Four FSUs are tested: non-operated control levels; levels that are incised; levels that are incised and treated with GDF-6 and carrier and levels that are incised and treated with carrier alone. Each FSU is mounted in two aluminum alloy cups and secured with cold cure dental cement. Care is taken to ensure that the IVD is aligned with the cups. Prior to the commencement of testing each FSU is preloaded to a constant until a reproducible state of hydration is achieved. This constant stress is used as the baseline prior to each test. The constant stress simulates relaxed standing and is based on in-vivo measurement of intradiscal pressure (Wilke H-J et al., *Spine* 24:755-62, 1999). A torsional load and flexion-extension, lateral bending load is applied over 10 cycles whilst under a constant axial load. A cyclic axial load is applied to investigate the axial compression response of the IVD.

Example 6

Intracellular Delivery of MSX-1 and/or MSX-2

6.1 Peptides

MSX-1 or MSX-2 polypeptide fused to a HIV-1 tat protein transduction domain and a hexa-histidine tag is produced by recombinant means. As a control a beta galactosidase protein fused to a HIV-1 tat protein transduction domain and a hexa-histidine tag is produced. Recombinant protein is isolated using a nickel-NTA column.

6.2 Cells

Sprague-Dawley rats aged 11 months are euthanized and IVD tissue from the lumbar spine and tail harvested under sterile conditions. Annulus fibrosus and nucleus pulposus are separately dissected and diced. The IVD tissue is placed in Dulbecco's modified Eagle's medium and Ham's F12 medium (DMEM/F-12; GIBCO BRL, Grand Island, N.Y., U.S.A.) containing 100 unit/ml penicillin and 100 mg/ml streptomycin. The IVD tissue is treated with 0.2% pronase (Sigma Chemical, St. Louis, Mo., U.S.A.) in the medium for 1 hour at 37° C. and then treated with 0.025% collagenase (Sigma Chemical, St. Louis, Mo., U.S.A.) for 6 hours at 37° C. Isolated cells are washed and filtered through a 70 mm mesh (Falcon, Franklin Lakes, N.J., U.S.A.) into 75 cm$^2$ flasks with 12 ml DMEM/F-12 medium containing 10% fetal bovine serum (FBS), 100 unit/ml penicillin, 100 mg/ml streptomycin, 2 mM L-glutamine and 50 mg/ml ascorbate. The cells are grown at 37° C. in 5% $CO_2$ with humidification. The culture media is changed every 2 days for approximately 8 days.

When the primary culture of IVD cells become confluent, the cells are sub-cultured into 6-well plates at 400,000 cells per well. Three days later, the cells are treated with either the MSX-1 fusion protein or a MSX-2 fusion protein or both fusion proteins or the LacZ fusion protein. Cell number is determined at day 0 by counting a control well using a hemocytometer. Cells are maintained in the presence of the peptide for two weeks. The medium is changed every 3 days during the experiment.

The sulfated-glycosaminoglycan (sGAG) content of the culture media is assayed using the 1,9-dimethylmethylene blue (DMMB) method. The culture media 2 ml is centrifuged (5000×G for 30 minutes) to concentrate the sGAG using the Centricon YM-50 centrifugal filter (Millipore Co., Bedford, Mass., U.S.A.). The sample solution (20 ml) is mixed gently with 200 ml DMMB dye solution in a 96-well microtiter plate, and the optical density (OD) was checked immediately at 520 nm wavelength filter. A standard curve is constructed using serial dilutions of chondroitin sulfate (Sigma Chemical, St. Louis, Mo., U.S.A.). Total sGAG in the media is normalized by DNA content and presented as a ratio to the untreated control.

The cell number is determined by the DNA content of each well, and DNA content is measured with a Hoechst dye 33258 (Polysciences, Warrington, Pa., U.S.A.) method. Cultured cells are removed from the plate by exposure to papain (10 units/ml). Cells are pelleted and incubated at 60° C. for 3 hours. A twenty microliter aliquot of the papain digest is mixed with 200 ml of Hoechst dye 33258 solution in a 96-well fluoroplate. Emission and excitation spectra are measured in Luminescence Spectrometer LS 50B (Perkin-Elmer, Wellesly, Mass., U.S.A.) at 456 nm and 365 nm, respectively. Standard curves are generated at the time of each measurement using known concentrations of calf thymus DNA (Sigma Chemical, St. Louis, Mo., U.S.A.).

Recombinant peptides are administered to an animal model (e.g., as described in Example 4) using a standard needle or as described in Example 9 hereof. The effect of the peptides on the animals is determined essentially as described in Example 5.

Example 7

Treatment of IVD Degeneration with Adenovirus Expressing MSX-1 or MSX-2

7.1 Adenoviral Constructs

Recombinant type 5 human adenoviral vectors with complete deletion of the E1A and E1B regions and a partial deletion of the E3 region of the viral genome are used in this study (Bett et al., *Proc Natl Acad Sci USA* 91: 8802-8806, 1994). A therapeutic vector contains a cDNA encoding MSX-1 or MSX-2 gene under control of the cytomegalovirus promoter (AD-MSX) at a concentration of $5 \times 10^{12}$ pfu/ml. Control adenoviral vector contains the beta-galactosidase gene under control of the cytomegalovirus promoter (Ad-beta-gal), also at a concentration of $5 \times 10^{12}$ pfu/ml.

7.2 Administration of Ad-GDF-6 and Ad-beta-gal

Rabbits treated as described in Example 4 are anesthetized. Viral solution comprising therapeutic vector or control vector (7.5 µl of a solution comprising $3.75 \times 10^{10}$ pfu) as described above under section 7.1, is administered to a punctured disc that has been induced to undergo disc degeneration, or alternatively, a control disc. Therapeutic vector is administered into one disc in each animal and control vector is administered into a separate disc in each animal. Administration is achieved using a standard needle (e.g., a 19-gauge needle and a Hamilton microsyringe) or essentially as described in Example 9 hereof.

Animals are analyzed essentially as described in Example 5.

Example 8

Treatment Using Stem Cells Expressing GDF-6 and/or MSX-1 and/or MSX-2

8.1 Expression Constructs

Nucleic acid encoding GDF-6 or MSX-1 or MSX-2 under control of a CMV promoter is inserted into an HIV-1-based self-inactivating (SIN) lentiviral vector (pHRSINcPPT-SEW). As a control, a vector expressing the eGFP reporter gene under the control of the spleen focus-forming virus (SFFV) LTR is used.

8.2 Isolation, Purification and Expansion of Mesenchymal Stem Cells (MSCs)

Bone marrow cells are collected by flushing the femurs, tibias and iliac crests from New Zealand white rabbits with PBS supplemented with 2% fetal bovine serum (FBS; Gibco, Paisley, UK). Red blood cell-depleted bone marrow mononuclear cells (BMMNCs) are plated at a density of $10^6$ cells/$cm^2$ in mesenchymal medium with mesenchymal supplements (Stem Cell Technologies, Vancouver, Canada), further supplemented with 100 IU/ml penicillin and 100 µg/ml streptomycin (Gibco). Non-adherent cells are eliminated by a half medium change at day 3 and the whole medium is replaced weekly with fresh medium. The cells are grown for 2-3 weeks until attaining near confluence. The whole adherent fraction is then detached by trypsinization and re-plated using a 1:3 dilution factor. Subsequent passing and seeding of the cells is performed at a density of 5000 cells/$cm^2$. To enrich MSCs, adherent cells from passage 2 (P2) and 3 (P3) are stained with anti-CD45-CyChrome and CD11b-PE (BD Biosciences, Oxford, UK), or a combination of CD45 and biotin-conjugated lineage (Lin) cocktail antibodies (Stem Cell Technologies) followed by streptavidin-PE. The negative fraction from both cell surface antigens is sorted using the flow-activated sorter Vantage (Becton-Dickinson, Oxford, UK). Enriched MSC populations are cultured under the same conditions as described above.

8.3 In Vitro Lentivirus-Mediated Gene (eGFP) Transfer into MSCs

Transduction of MSCs is performed with the expression constructs as described above under section 8.1. For transduction, $1 \times 10^4$ purified MSCs from passage 4 (purP4) are seeded into individual wells of a 12-well plate. The following day virus particles are added at multiplicity of infection (m.o.i.) of 5, 10, 30 or 50 and transduction is performed for 20 hours. Cells transduced with an eGFP expressing vector are harvested on day 1, 3 and 5 after virus removal and analyzed for eGFP expression by flow cytometry.

8.4 Treatment of Animals Using Transduced Stem Cells

Rabbits treated as described in Example 4 to induce IVD degeneration are treated with the transduced stem cells prepared as described above under section 8.3. Transduced stem cells ($2 \times 10^6$), that are obtained a few days post-viral removal to minimize further expansion, are administered directly into the treated IVD of the rabbits using a standard needle or as described in Example 9 hereof. Rabbits are analyzed essentially as described in Example 4 and 5 to determine the effect of stem cell infusion, i.e., re-population and repair of the degenerated IVD.

8.5 Tissue Processing and Immunohistochemistry

To determine the survival of stem cells, cells expressing eGFP in control administrations are stained for eGFP expressions. Tissues are fixed in 10% neutral buffered formaldehyde (NBF), embedded in paraffin and in some cases the other half of each tissue is cryo-embedded. Each embedded tissue is sectioned between 10 to 15 levels with a 70 to 100 µm gap between each one. Each level is serially sectioned at least 4 times. Sections (4 µm thick) are screened for the presence of eGFP either by staining with an eGFP antibody (Santa Cruz Biotechnology), or by direct visualization using a fluorescent microscope (Zeiss AxioVision2™, Zeiss, Welwyn Garden City, UK).

Example 9

Use of a Device for the Delivery of GDF-6 Signaling Modulator to an IVD or a Region Adjacent or Surrounding an IVD in an Animal Model Recombinant GDF-6 (Example 5) and/or recombinant MSX-1 (Example 6) and/or recombinant MSX-2 (Example 6) is administered to the animal models described in Example 4 hereof, essentially following the protocols described in Examples 5 and 6, with the exception that the GF6-modulatory composition is formulated in lactose solution and in a hydrogel or co-polymer for administration to an IVD or a region adjacent or surrounding an IVD using the device exemplified in FIGS. 8-18.

Figure 8:
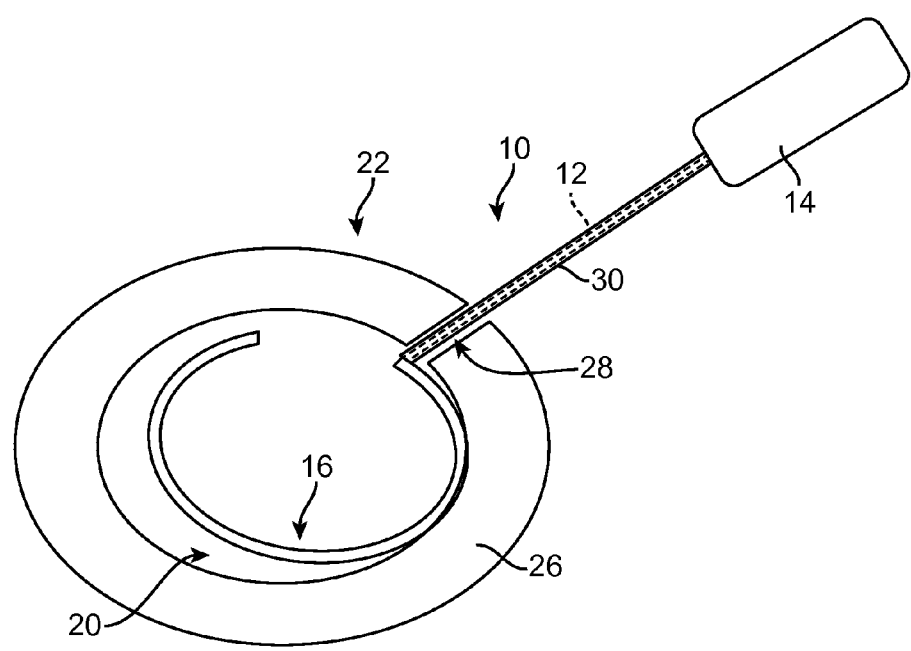
FIG. 8 shows a schematic, three dimensional view of a device for use in the delivery of a GDF-6 signaling modulator or other composition as described herein to an IVD or a region adjacent or surrounding an IVD in a subject.
Figure 9:
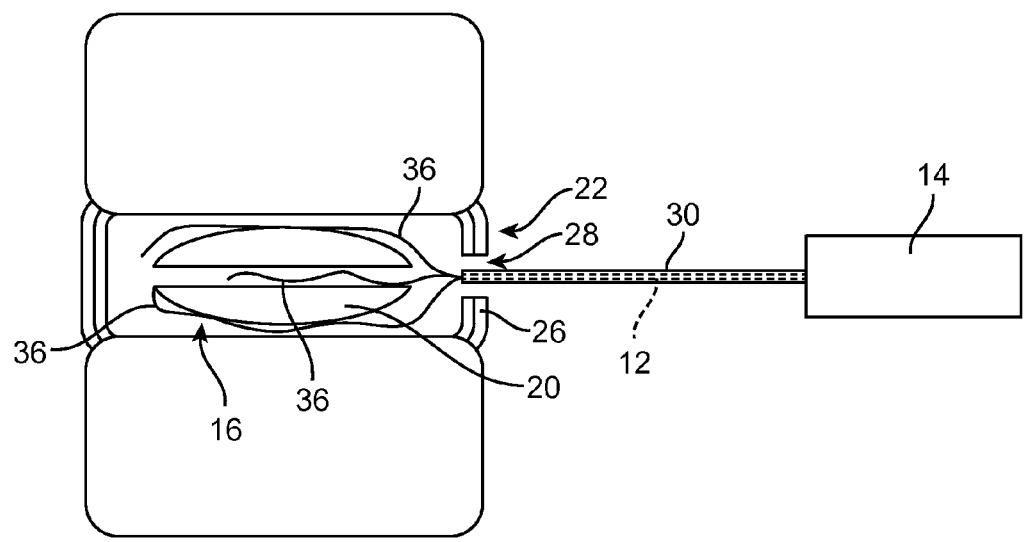
FIG. 9 shows a schematic, three dimensional side view of a second embodiment of a device for the delivery of a GDF-6 signaling modulator to a site in a patient's body at which tissue is to be treated.
Figure 12:
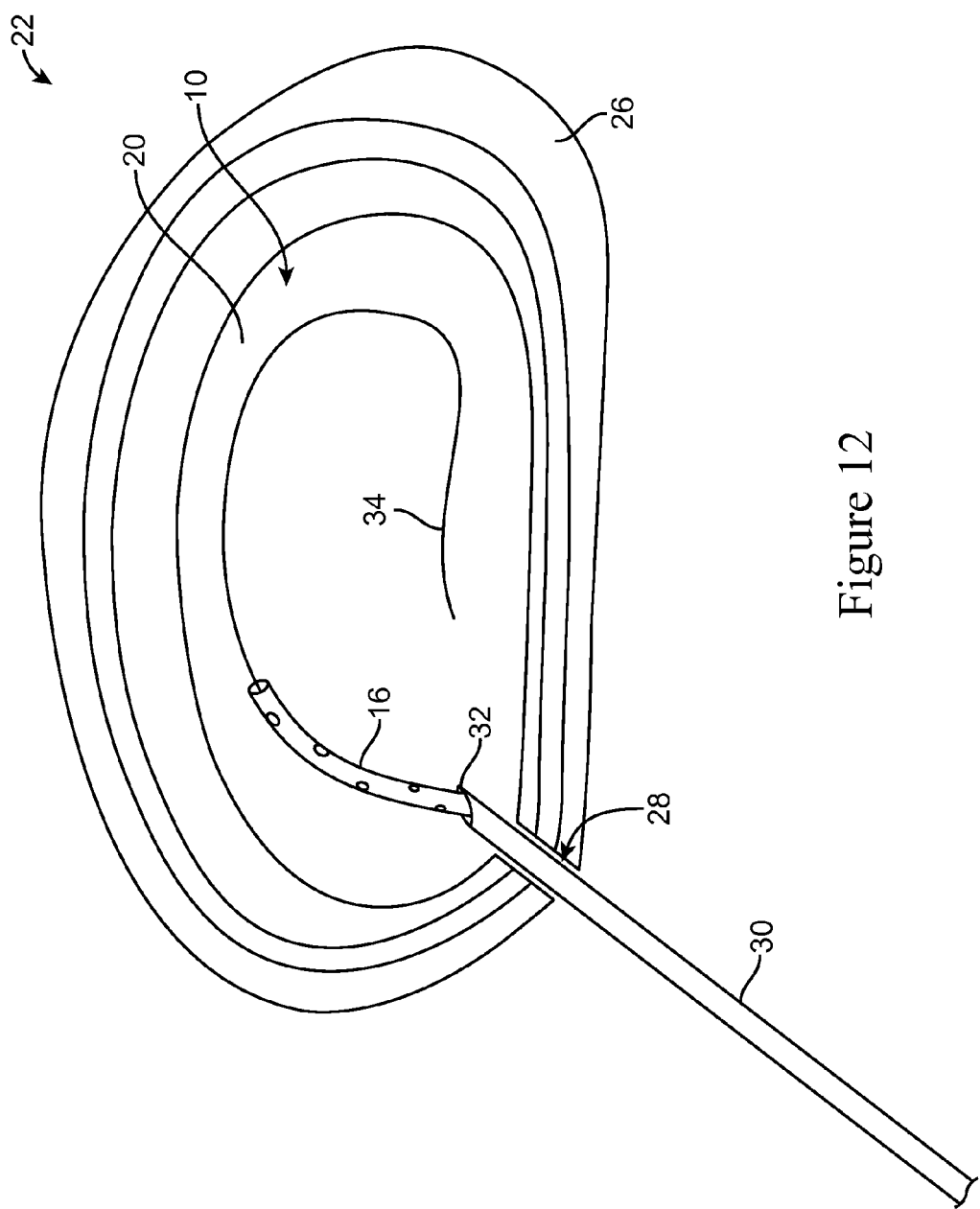
FIG. 12 shows a schematic, sectional plan view of a third embodiment of a device for the delivery of a GDF-6 signaling modulator to a site in a patient's body at which tissue is to be treated.
Figure 13:
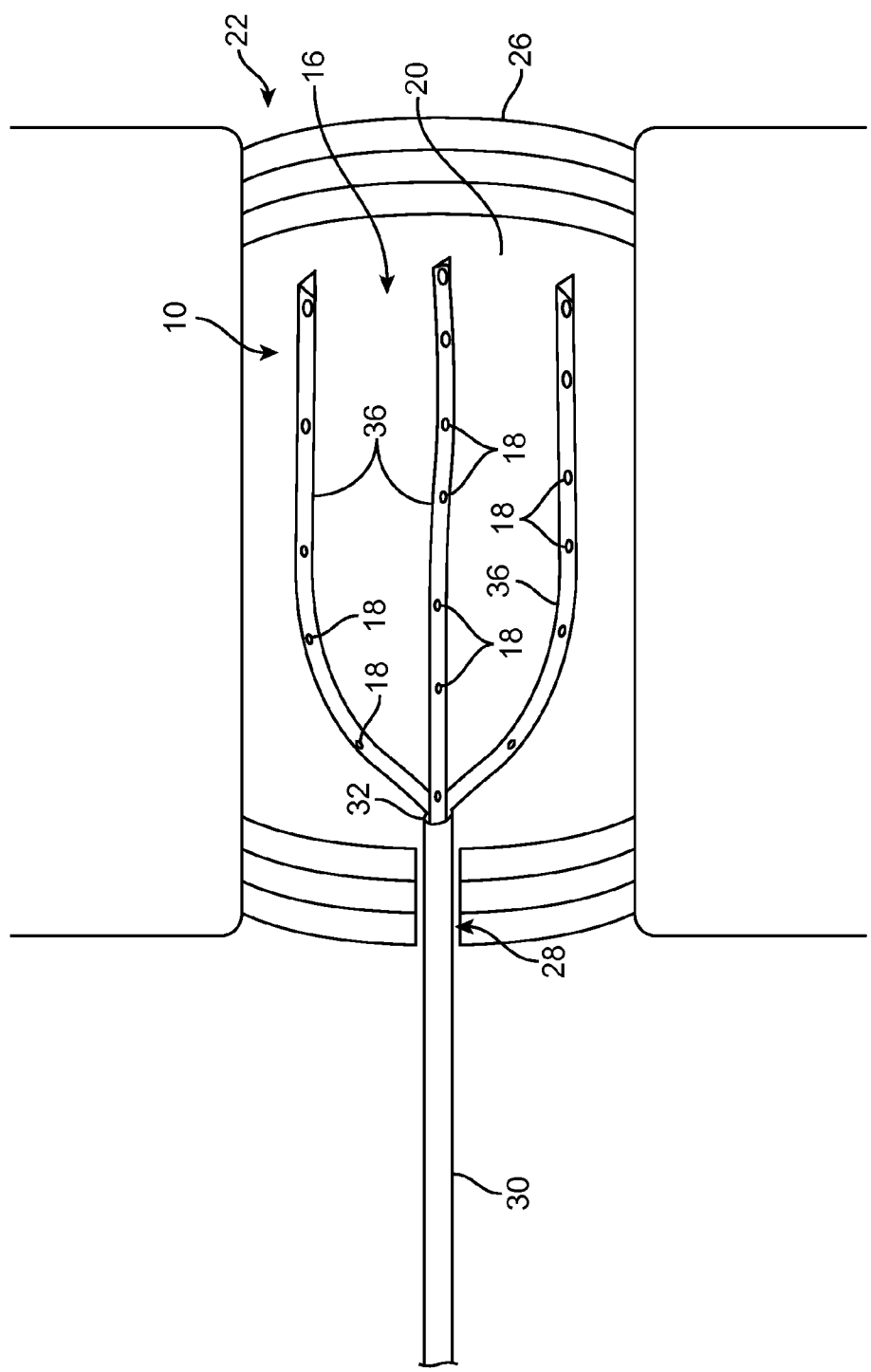
FIG. 13 shows a sectional side view of the device of FIG. 9.
Figure 14:
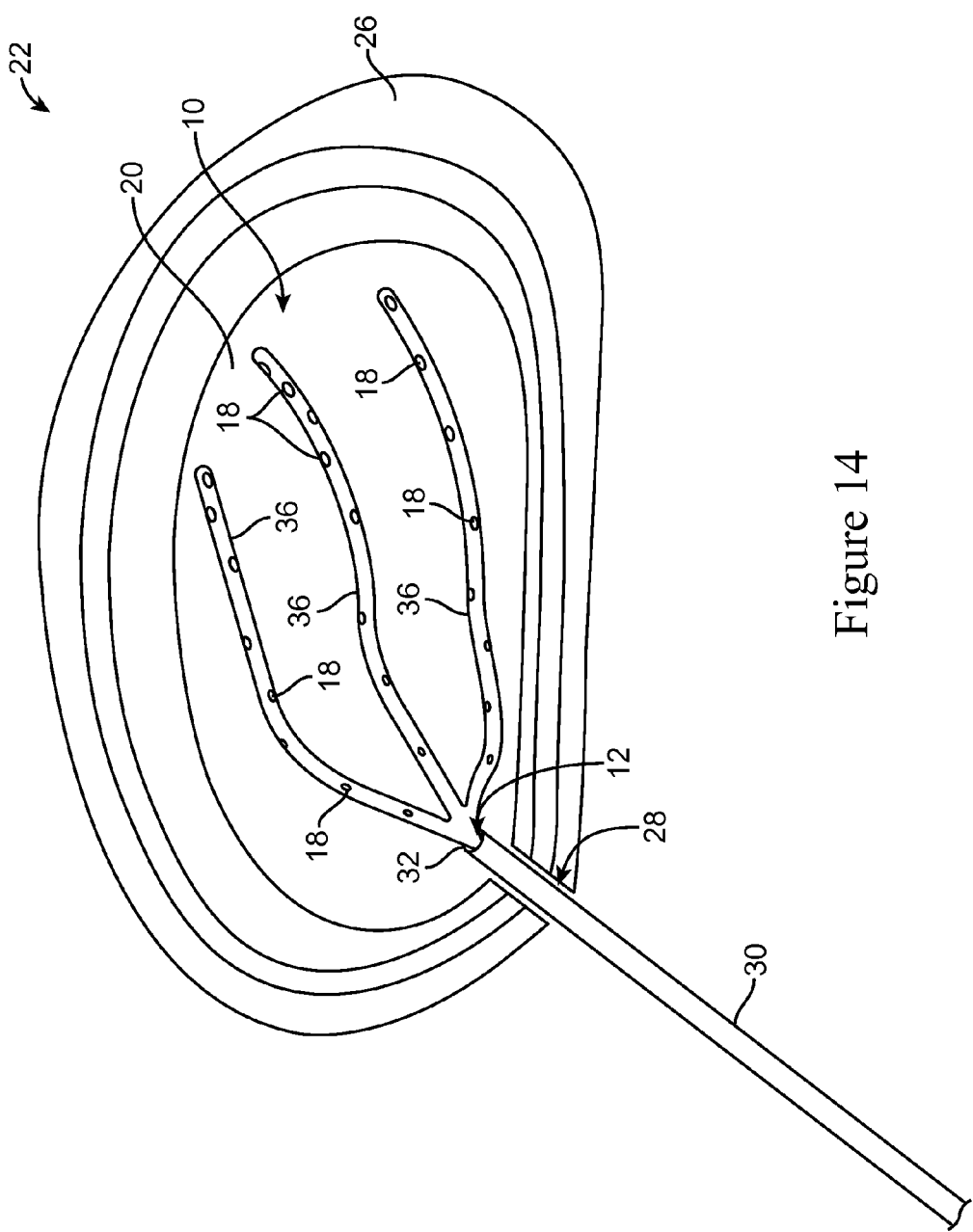
FIG. 14 shows a schematic, sectional plan view of the device of FIG. 9.
Figure 15:
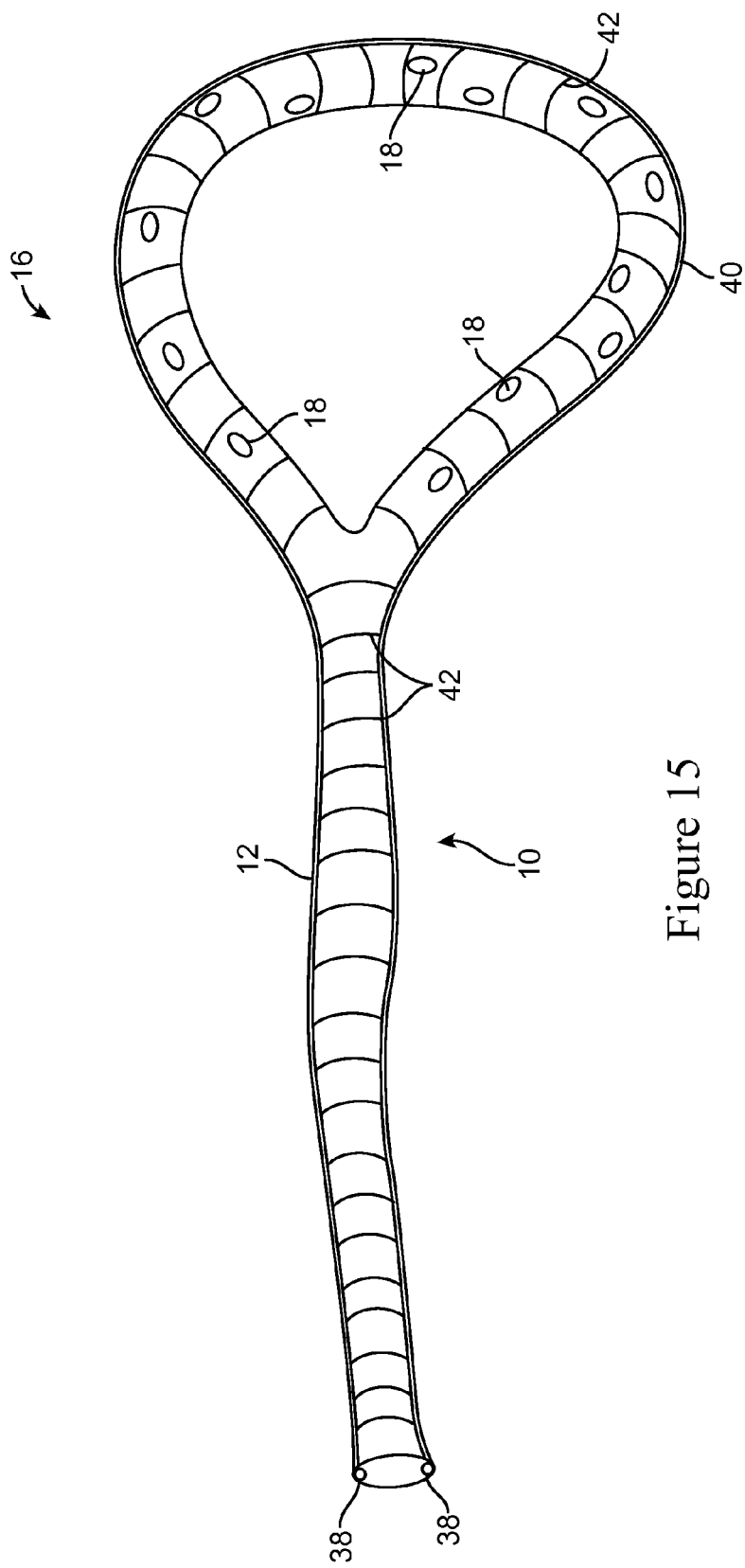
FIG. 15 shows a schematic, plan view of a fourth embodiment of a device for the delivery of a GDF-6 signaling modulator to a site in a patient's body at which tissue is to be treated.
Figure 16:
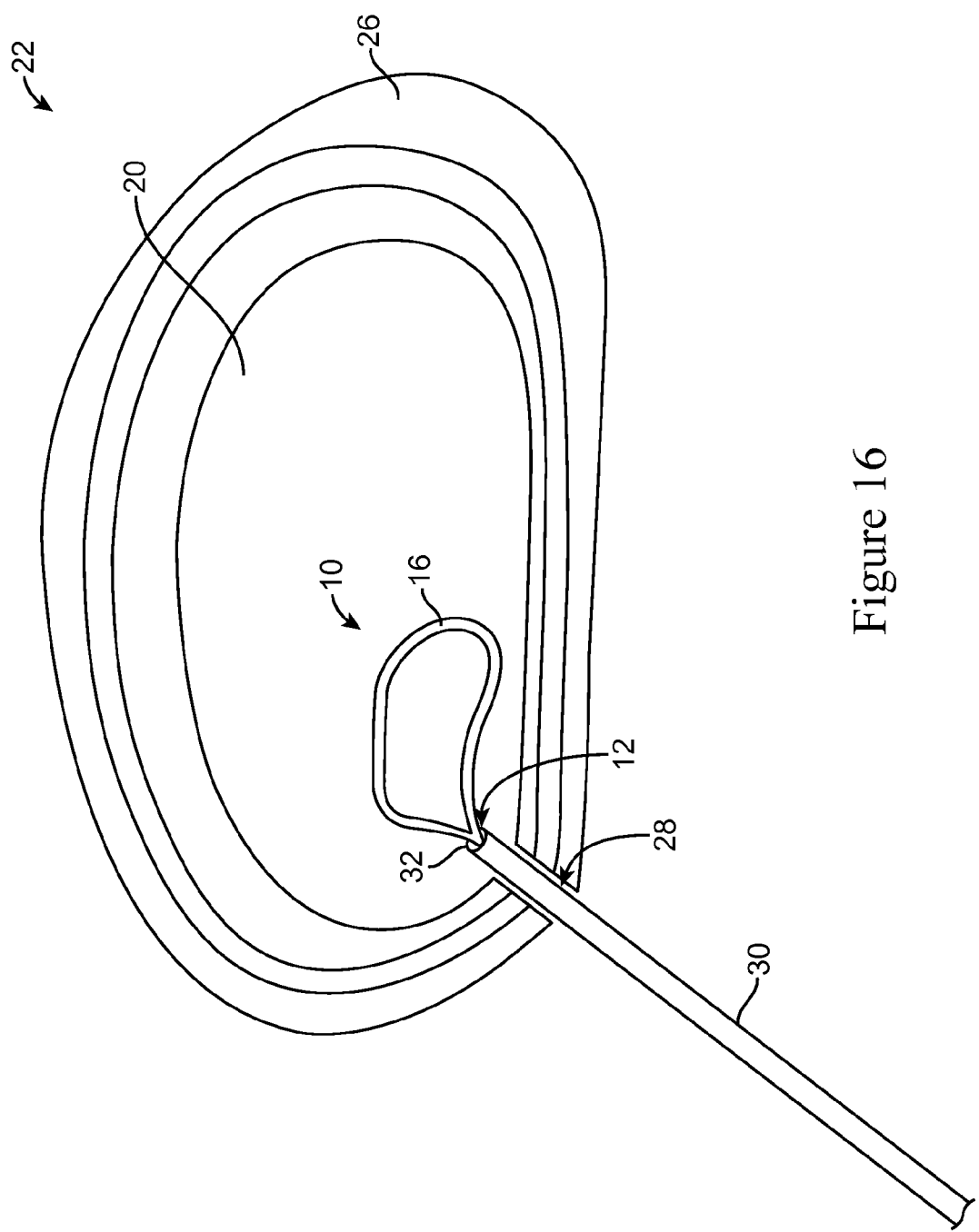
FIG. 16-18 show various stages in the deployment of the device of FIG. 15, in use.
Figure 17:
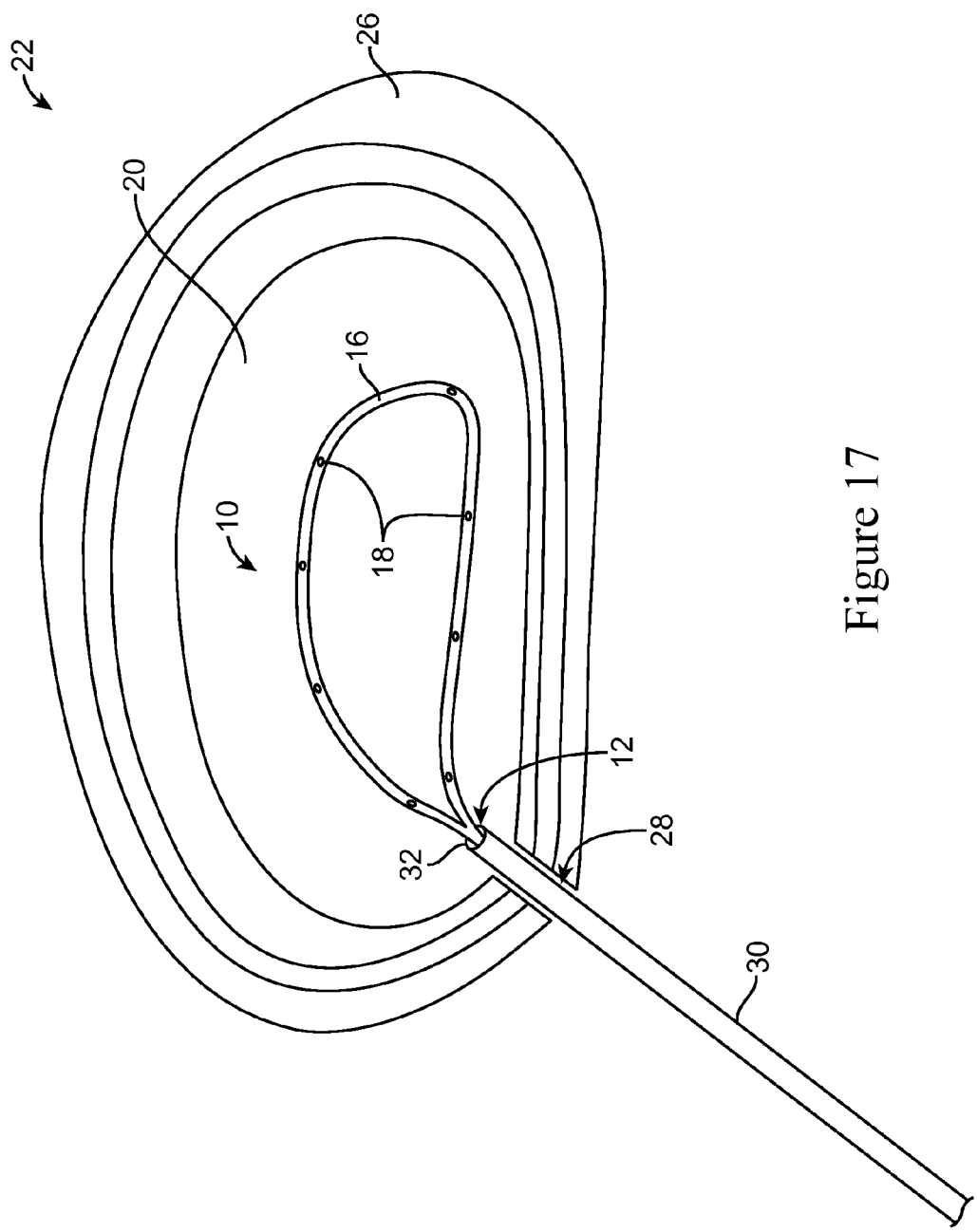
Figure 18:
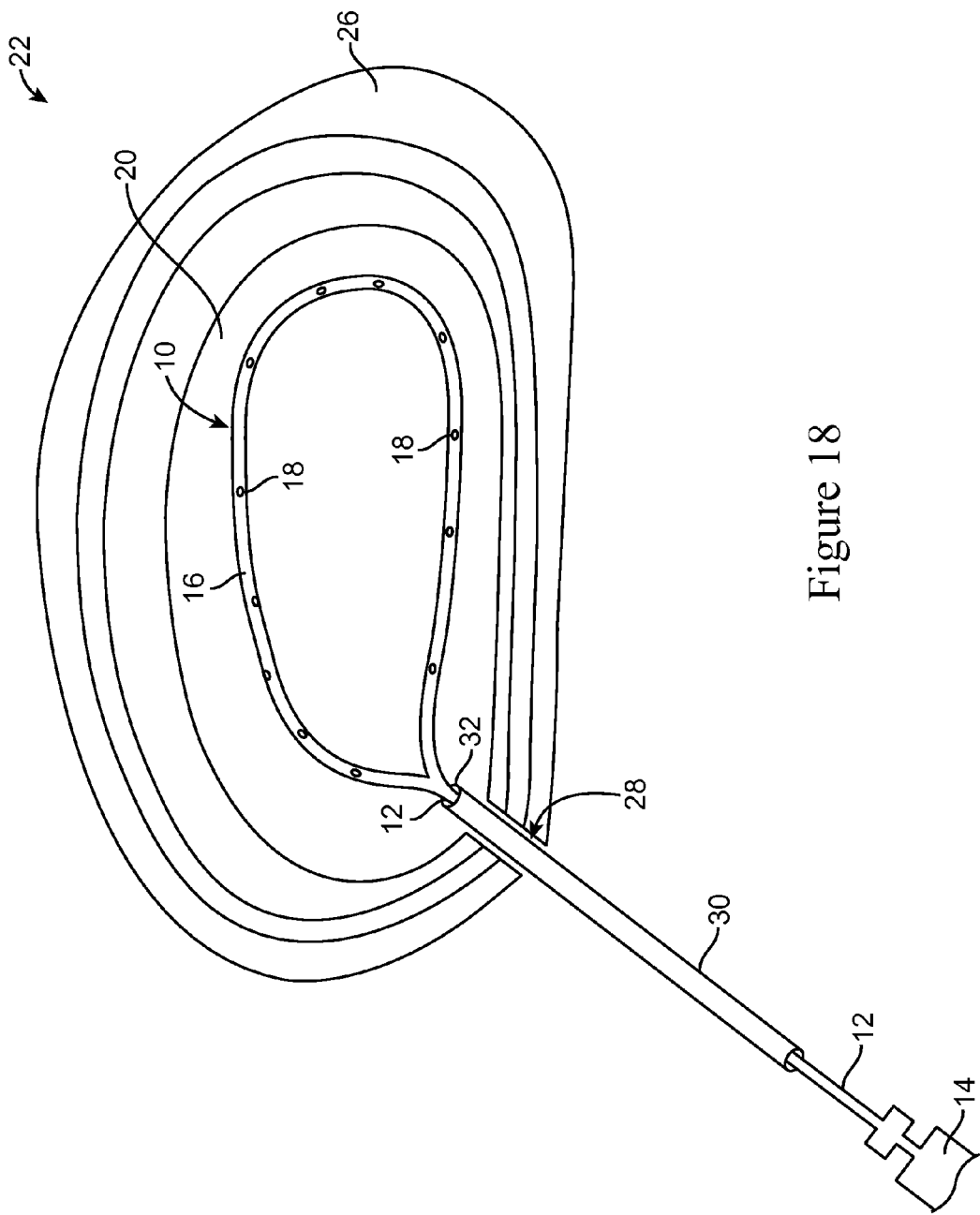

Referring to FIGS. 8-10, the delivery device 10 includes a delivery conduit 12 having a proximal end attachable to a source 14 of the compositions of the invention to be administered, the device 10 and the source 14 forming a system for the delivery of the compositions to an IVD or a region adjacent or surrounding an IVD in a subject in need thereof. The source 14 is, typically, a syringe for dispensing the compositions through the delivery conduit 12.

An emitter structure 16 is arranged at the distal end of the delivery conduit 12. The emitter structure 16 defines, as shown in greater detail in FIG. 10 of the drawings, a plurality of discharge apertures 18 arranged at longitudinally spaced intervals. The discharge apertures 18 are configured to effect uniform, diffuse distribution of a composition of the invention throughout an IVD nucleus 20 (FIG. 10) of an IVD 22. To effect the uniform, diffuse distribution of the composition, the apertures 18 closer to the distal end of the delivery conduit 12 are of smaller diameter than the apertures 18 distally arranged on the emitter structure 16. In such a fashion, there is a substantially uniform discharge of the agent through the apertures 18 of the emitter structure 16 to facilitate the diffuse distribution of the agent throughout the nucleus 20 of the IVD 22 or a region adjacent or surrounding an IVD.

The emitter structure may have a diameter in a range from about 0.1 mm to about 3.5 mm and may be formed of a reinforced, suitable plastics material, for example. The reinforcing may be in the form of bands (not shown) arranged at longitudinally spaced intervals to retain the emitter structure 16 in an open condition against pressure exerted by the tissue of the nucleus 20 in use.

The emitter structure 16 may be steerable to adopt a loop shape in the nucleus 20 as shown in FIGS. 8-10. To achieve this, the emitter structure 16 may have a steering wire or pull wire (not shown), for example, embedded in its wall. Manipulation of the steering wire is carried out by a clinician with the assistance of, for example, fluoroscopy, to ensure that the emitter structure 16 adopts a spread out configuration within the nucleus 20 of the IVD 22.

The emitter structure 16 may have alternative configurations such as a preformed guide wire instead of a steering wire such that the emitter structure 16 adopts a similar loop-shape, or it may be forked having a plurality of branches to effect distribution of the composition through the nucleus 20 of the IVD 22.

To introduce the emitter structure 16 into the nucleus 20 of the disc 22, an annulotomy is formed on an annulus 26 of the IVD 22. The annulotomy results in an access opening 28 being formed in the annulus 26 of the disc 22. A working cannula 30 is inserted percutaneously through the subject's skin in a minimally invasive manner. The working cannula 30 may also be used for performing the annulotomy on the annulus 26. Thus, a tip of the working cannula 30 is sharpened or beveled for effecting perforation of the annulus 26.

Once a tip 32 of the working cannula 30 has been inserted into the nucleus 20 through the opening 28, the emitter structure 16 of the delivery device 10 is extended through the end 32 of the working cannula 30 to adopt the position shown, for example, in FIG. 10 of the drawings and enabling a diffuse, substantially uniform distribution of the composition of the invention throughout the nucleus 20 to be effected.

Once delivery of the composition has been completed, a positive pressure is maintained in the envelope to inhibit back flow of the composition through the apertures into the interior of the emitter structure 16. This is done in one of a number of ways such as (a) having a non-return valve in each aperture; (b) maintaining a continuous pressure, for example, by a motorized pneumatic device (not shown) while withdrawing the emitter structure 16 into the working cannula 30 or (c) pumping air into the emitter structure 16 behind the agent.

Use of the device 10 targets the composition to the nucleus of an IVD and facilitates diffuse, substantially uniform distribution of a composition of the invention to the IVD such that the composition is more evenly distributed throughout the tissue, i.e., from the nucleus or to a region adjacent or surrounding an IVD.

Example 10

Production of Recombinant Human GDF-6 and a Bioactive Fragment of GDF-6

10.1 Cell Transfections

Approximately 2.5×105 CHO cells maintained in serum free medium were transfected with an expression vector comprising full length GDF-6 cDNA fused to a FLAG tag or an expression vector comprising a cDNA encoding an active domain of GDF-6 fused to a FLAG tag (SEQ ID NO: 25) in 6-well plates using Lipofectamine 2000 (Invitrogen) according to manufacturer's instructions. Briefly, 12 µl of Lipofectamine 2000 was mixed with 5 µg vector in a total volume of 250 µL, 20 minutes before addition to CHO cell cultures. Lipofectamine/vector mixtures are then added to CHO cells and incubated for 5 hours. Proteins secreted into the supernatant were harvested and analyzed by Western blotting and Alkaline Phosphatase activity.

Western Blotting

Concentrated supernatants from one well of a 6-well plate were separated using polyaclylamide gel electrophoresis (PAGE) under either reducing conditions. Proteins were transferred to nitrocellulose membranes and detected with antisera specific for GDF-6 or for the FLAG tag, secondary antibodies and detection system.

Alkaline Phosphatase Assay

Cells were incubated with GDF-6 or the active fragment for varying periods of time then lysed with 0.1% TritonX-100 in PBS buffer. Lysates were then incubated for 30 minutes at 37° C. with the alkaline phospatase substrate, p-nitrophenylphosphate (Sigma-Aldrich) at 2.5 µg/ml. The levels of p-nitrophenol (PNP) production were measured by a spectrophotometer and concentrations were determined by comparison with a standard curve created with known amounts of p-nitrophenol. Alkaline phosphatase activity was expressed as nanomoles of PNP generated per microgram of total cellular protein per minute.

Results

Figure 19:
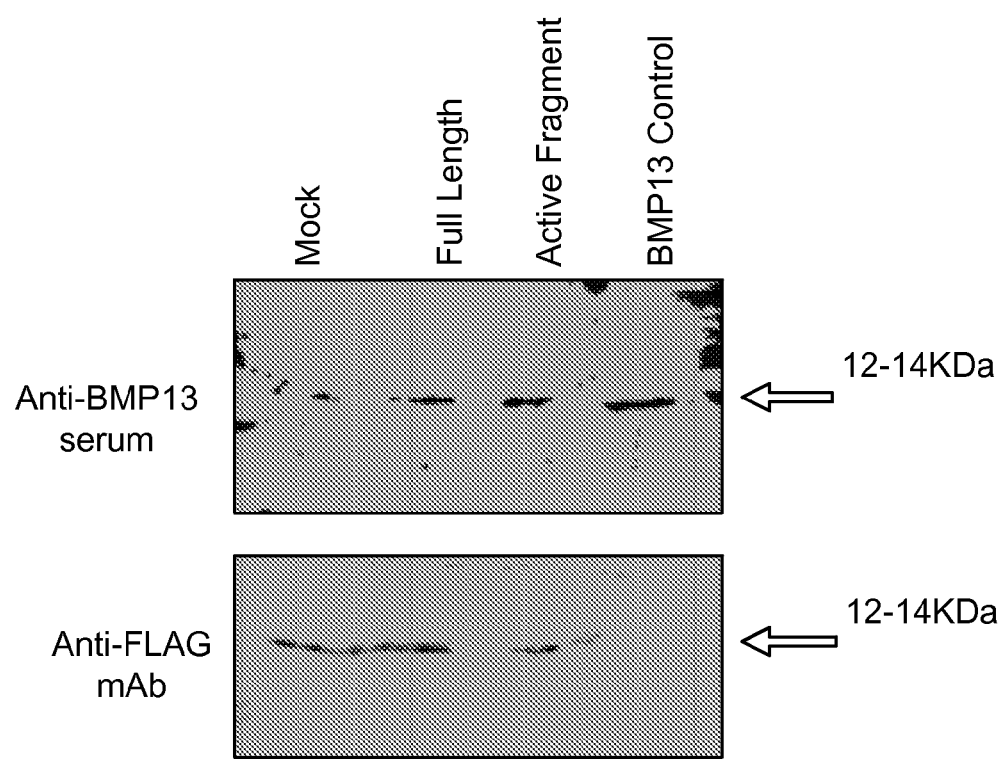
FIG. 19 is a copy of photographic representations showing Western blots of supernatants from Chinese Hamster Ovary (CHO) cells separated by SDS-PAGE and probed with BMP13 polyclonal antiserum (top panel) or mAb against the FLAG tag (bottom panel). Cells were transfected with expression vectors comprising cDNA encoding full-length GDF-6 (full-length) or an active fragment thereof (active fragment). GDF-6 control (Control) was protein provided with the antibody when purchased. Negative control was mock-transfected cells. Results show bands detected by antiserum recognising GDF-6 in supernatants from cells transfected with cDNA encoding full-length GDF-6 or cDNA encoding the active fragment but not mock transfected cells. The band size corresponds to the commerically provided control protein. The identified GAF-6 bands are also recognised by the FLAG tag-specific mAb (Sigma), but the control protein was not.

As shown in FIG. 19 Western blotting of supernatant from cells transfected with full-length GDF-6 or active fragment of GDF-6 using anti-GDF-6 antisera detected a band of approximately 12-14 kDa, similar to the positive control. This band was not detected in supernatants from mock transfected cells. The identified GDF-6 bands are also recognised by the FLAG tag-specific mAb (Sigma), however, control protein was not, as expected since the control protein does not comprise a FLAG tag. These data indicate that the GDF-6 protein detected was a product derived from the transfected cDNA.

When protein isolated from CHO cells expression either full-length GDF-6 or active domain of GDF-6 is analyzed using non-reducing PAGE, the size of the protein detected is indicative of a homodimer formation.

In addition the protein purified from the supernatant of transfected cells possessed equivalent/greater alkaline phosphatase activity than commercially obtained protein produced in *E. coli*.

These results indicate that a truncated GDF-6 with a FLAG peptide attached, was produced in CHO cells and secreted into the culture media. The protein forms homodimer reminiscent of normal GDF-6 homodimers, and possessed levels of alkaline phosphatase activity comparable to that of full-length GDF-6.

Example 11

Treatment of a Sheep Model of IVD Degeneration

Sheep are be purchased from the University farm, Arthursleigh, Australia, and transported to a veterinary centre a minimum of 2 weeks prior to first experimental procedure and housed in a paddock. Each sheep is premedicated with 0.3 mg/kg diazepam and individually taken to the anesthesia induction area immediately prior to the surgical procedure. The jugular vein is catheterized using a 16 G×3.25 cm catheter after local anesthetic is placed under skin using a syringe and 25 gauge needle. Sheep are anaesthetized with 10 mg/kg ketamine given to effect. The sheep are placed in right lateral recumbency and the right caudal quarter of the sheep clipped and aseptically prepared. A straight incision a few fingerbreadths below the costal margin and parallel to lateral border of the erector spinae muscles is made to allow exposure of the lower lumbar vertebrae (L2 to L6). The approach is made retroperitoneally using electrocautery to divide the subcutaneous tissue, fascia, and thoracolumbar aponeurosis and transversalis fascia in line with the skin incision, the peritoneum is protected and reflected anteriorly by blunt dissection. A retractor is placed between rostral and the iliac crest to aid exposure. The vertebral bodies from L3 to L5 are identified and, with a Deaver retractor, the vessels lying anterior to the spine are protected. Once the appropriate involved vertebra is identified, the psoas muscle is elevated bluntly off the lumbar vertebrae and retracted laterally to the level of the transverse process with a Richardson retractor. Bipolar coagulation of vessels around the vertebrae is also performed. The fibrosus annuli of anterolateral discs of L2 to L5 are identified. Annular fibrosus of two non-contiguous lumbar discs per animal. The incision of fibrous annulus is made to a 6 mm depth using a #9 B-P knife blade. The IVD located between the two punctured IVDs is used as a control. A 27 mm×10 mm titanium screw is implanted into the vertebral body at one level for later identification of levels. One of the punctured levels will is treated with 300 ug of full-length GDF-6 or an active domain thereof produced essentially as described in Example 10 in saline solution, and the other punctured disc treated with saline control. In both cases the treatment is injected into the nucleus pulposus of punctured discs. After completion of procedure, the wound is closed in layers.

Radiographs (lateral only) are taken prior to waking of animals. Two weeks after surgery and monthly thereafter, radiography are performed on the assigned sheep using 0.3 mg/kg diazepam and 0.2 mg/kg butorphanol intravenously for sedation. The remaining radiographs and CT scans are performed after euthanasia on the assigned days (4, 8 and 18 months). Disc height is also raidographically determined on a monthly basis (lateral view only) and following euthanasia. ND height is expressed as a disc height index (DHI). The level of degeneration based on the Thompson grade (1=normal, 4=severely degenerated) is also assessed using MRI.

Following four, eight or eighteen months, sheep are euthanized using an overdose of pentobarbitone administered intravenously. After euthanasia the sheep spines are removed for analysis and subjected to CT and MRI scans.

Lumbar vertebral joints are biomechanically tested using an Instron 8874 in 4 modes. Range of motion, constraint to motion, and hysteresis will be quantified for the treated joints and compared to controls. Annular tissue samples from treated joint levels and controls are to be isolated and tested in tension to determine ultimate strength and tensile modulus.

Disc tissue collected post-mortem is subject to histological analysis to assess the level of disc degeneration. Spines are removed surgically and muscle tissue removed before being submerged in working formalin solution (10% in 0.1M Phosphate buffer). Spines are labeled according to head/tail orientation. After initial fixation, spines are segmented into individual discs labeled +2, +1, −1, −2 in relation to the position of the titanium screw inserted at surgery, and thus identifiable in respect of the treatment administered. Discs are then decalcified. Individual discs are sectioned into pieces of tissue no more than 5 mm thick, placed in cassettes for paraffin embedding and thin sectioning. Tissues are then stained with haematoxylin/eosin for tissue architecture analysis.

Example 12

GDF-6 Regenerates Disc in a 4-Month Sheep Annular Tear Model

Figure 20:
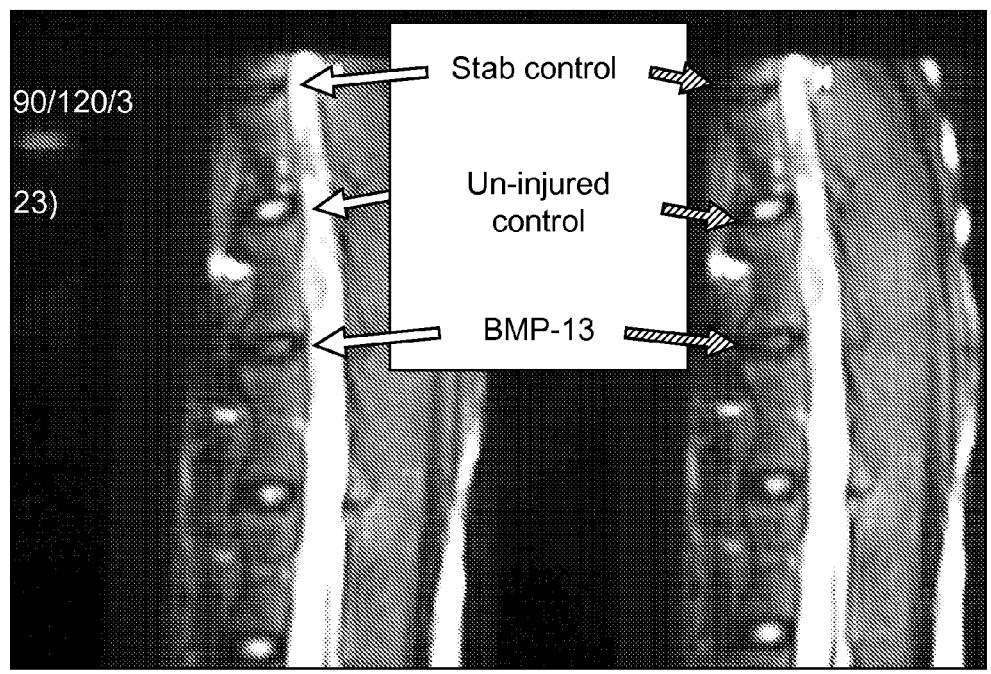
FIG. 20 is a copy of a photographic representation showing results of an MRI scan of sheep that have undergone surgery to expose three IVDs, one of which was injured and treated with saline (designated "stab control"), another was injured and treated with recombinant human GDF-6 (designated "GDF-6"), and a third was not injured or treated (designated "un-injured control"). The stab control shown advanced nuclear pulposus degeneration. In contrast, the morphology of the GDF-6 treated disc is more similar to the untreated and undamaged disc than it is to the stab control, indicating that GDF-6 slows and/or prevents IVD degeneration and/or enhances or induces IVD regeneration.

Sheep (n=7) underwent left retroperitoneal exposure of their lumbar spine and three discs were exposed. Two discs were injured with a No 15 bard Parker Blade to a 6 mm depth and one injected with 70 µl of saline and the other injected with 70 ul of recombinant human GDF-6 (rhGDF-6). The remaining disc was left uninjured and untreated. To mark the level of the discs a titanium screw was implanted into a marker vertebral body. Sheep were sacrificed at 4 months or 8 months. To evaluate early degeneration and its treatment highly sensitive MRI scans were used. Exemplary results are shown in FIG. 20. Degeneration grading was based on visual inspection evaluating predominantly nucleus pulposus hydration, end plate changes and disc height and blinded scoring was performed by two observers. Discs were graded as follows: Good disc (1), somewhat good disc (2), bad disc (3), Very bad disc (4) and finally extremely disc (5).

At the 4 month mark early degenerative changes were appreciated by both observers. All un injured controls were Good (1), saline controls were generally graded as very bad (4) and the majority of rhGDF-6 treated discs graded some what good (2). These results indicate that rhGDF-6 can reduce or delay IVD degeneration and/or enhance IVD regeneration in a sheep annular tear model.

Example 13

Treatment of Isolated IVD Cells with GDF-6 Induces Extracellular Matrix Production Harvest and Maintenance of Disc Cell Cultures Surgically-discarded human disc tissues were collected in sterile saline (0.9% NaCl; Baxter International Inc., Deerfield, Ill., USA) following patient consent. Tissues were repeatedly washed in sterile phosphate buffered saline (Invitrogen) until the solution was clear, then cut into approximately 1 mm$^2$ pieces prior to overnight digestion with 0.025% collagenase (Sigma-Aldrich, St Louis, Mo., USA). Following digestion with collagenase, cell suspensions were suspended in 0.02 M HEPES, 2% antibiotic-antimycotic (penicillin/streptomycin/fungizone (P/S/F)) and Hank's balanced salt solution (HBSS) (Invitrogen, Carlsbad, Calif., USA), in a shaking incubator at 37° C. The cells were then harvested with a 1000 rpm centrifugation step for 10 minutes, with the resultant cellular pellet resuspended into fresh culture media (10% fetal calf serum (FCS) (HyClone®, Tauranga, New Zealand) with 1% antibiotic-antimycotic (P/S/F) in DMEM) (Invitrogen) and cultured in monolayers, within a 37° C. cell culture incubator with 5% $CO_2$.

Trypsinisation and the Passaging of Cells

Cells were grown to confluency and passaged by trypsinisation and re-seeded at a lower density for further culturing or experimentation. Specifically, adherent cultures were washed twice with sterile, pre-warmed phosphate buffered saline for complete removal of existing culture media prior to incubation with trypsinisation solution (0.05% Trypsin-EDTA-4Na, 0.02 M HEPES in HBSS) (Invitrogen), completely covering the cellular surface, in the 37° C. cell culture incubator with 5% $CO_2$ until the cells were in suspension. Trypsin was then inactivated by addition 10% FCS containing culture media, with the entire contents subjected to a 5 minutes centrifugation step at 1000 rpm for the collection of trypsinised cells. The cells were then resuspended in fresh culture media, with an aliquot removed to determine the viable cellular density by visual-counting of non-trypan blue-stained cells, as described below, and subsequently seeded at an appropriate density into new culture flasks for continued culturing or experimentation.

Non-Trypan Blue Staining for Cell Viability Counting

Equal volumes of cell suspension to 0.4% trypan blue stain (Invitrogen) suspended in HBSS was mixed together and stained for 5 minutes at room temperature prior to applying a small sample under a freshly-placed coverslip on top of a hemacytometer (Bright-Line® hemacytometer, Sigma-Aldrich) until the chamber was full. The counting chamber (3×3 mm grid) was visualized microscopically, with the four corner (1 mm) grid counted for the number of viable non-stained cells. The calculation used to determine cell numbers per milliliter and total cells in suspension, was as follows: cells/ml=average count per square (1 mm grid)×dilution factor× $10^4$ and total cells 10=cells/ml×total original volume of cell suspension from which the sample was taken.

GDF-6 Stimulation Studies

Human disc cell cultures from either the annular, nuclear or endplate region were seeded into 60 mm$^2$ plates at a density of $1.6 \times 10^5$ cells per plate. On day three post-seeding, cells were stimulated with either media alone or containing 200 ng of GDF-6 (Peprotec Asia, Israel) and left to culture for a period of seven days. Culture media containing the stimulant was changed every three days. Upon the seventh day, the cultures were harvested for either western blotting analysis or real-time RT-PCR analysis.

Western Blot Detection of Matrix Protein Expression

Confluent cells cultured in 75 cm$^2$ flasks were washed twice with PBS and 500 µl of homogenization buffer (50 mM Tris pH 7.4, 0.1 mM EDTA, Leupeptin 1 µg/ml, Pepstatin 5 AEBSF 200 µg/ml) (Sigma-Aldrich) was added directly to the cultures and incubated for 20 minutes on ice prior to the removal of cells with a cell scraper. Cellular lysates were then briefly sonicated and stored in −70° C. with individual aliquots for subsequent determination of protein concentration using the Micro BCA™ Protein Assay Kit (Pierce, Rockford, Ill., USA) as well as Western blotting procedures.

For Western blotting, thawed lysates were suspended in an equal volume of 2× sample buffer (4% SDS; 20% glycerol; 25% 0.5 M Tris-HCl pH 6.8; 2-5% of 2-β mercaptoethanol and 0.1% Bromophenol blue)(NuSep). Approximately 12.5 µg of protein extracts were loaded onto and separated by 8% SDS-polyacrylamide gels (LongLife Gels)(NuSep). Proteins were then transferred to PolyScreen® PVDF hybridization membranes (PerkinElmer). Membranes were then incubated in blocking solution (5% skim milk in TTBS) overnight in a 4° C. refrigerator. The TTBS solution consisted of TBS (20 mM Tris, 137 mM NaCl at pH 7.6) with 0.1% Tween20 and was always freshly prepared. For the detection of protein expression, membranes were probed with either goat anti-collagen 2 antibodies (Santa Cruz, Calif., USA), rabbit anti-collagen 1 antibodies (Research Diagnostic INC, NJ, USA), rabbit anti-Sox 9 (antibodies Santa Cruz, Calif., USA) as primary antibody with 15 µl of antibody resuspended in 3 ml of 1% BSA in TTBS for each membrane, placed at room temperature for an hour in a hybridization oven rotating at 7 rpm. The membrane was then washed three times in TTBS for 10 minutes each and labeled with an anti-goat or anti rabbit horseradish peroxidase-conjugated secondary antibody (1.5 µl of antibody in 3 ml of 1% BSA/TTBS) (Chemicon, Temecula, Calif.) for an hour, at room temperature within a hybridization oven rotating at 7 rpm. Three consecutive 15 minute washes in TTBS was then performed, followed by another two 10 minute washes in TBS. The complexes were then detected by the Super Signal Chemilumnescent Substrate system (Pierce) as per manufacturer's instructions.

Following the initial probing of the membrane blot for matrix proteins, antibodies bound to the membrane were stripped to permit subsequent detection of β-actin protein expression, for the normalization of protein loading in each lane. The membrane was submerged in 20 ml of stripping buffer (Pierce) for 20 minutes in a shaking 37° C. incubator at 3.5 rpm. This was followed by a 10 minute wash in TTBS, for a total of three washes, prior to incubation with the mouse monoclonal anti-β-actin primary antibody (Sigma-Aldrich) (1.5 µl of antibody with 10 ml of 1% BSA/TTBS) for 1 hour at room temperature in a hybridization oven, rotating at 7 rpm. The membrane was then washed three times in TTBS, at 10 minutes each and labeled with an anti-mouse horseradish peroxidase-conjugated secondary antibody (1 µl of antibody added to 4.999 ml of 1% BSA/TTBS) (Chemicon, Temecula, Calif.) for 30 minutes at room temperature, within a hybridization oven rotating at 7 rpm. Two consecutive 10 minute washes in TTBS was then performed, followed by another two 10 minute washes in TBS. The complexes were then detected by the Super Signal Chemilumnescent Substrate System (Pierce) as per manufacturer's instructions. Expression levels of collagen-1, collagen-2 or SOX9 were then normalized with respect to β-actin levels to permit comparison of expression levels between samples.

Results

Figure 21A:
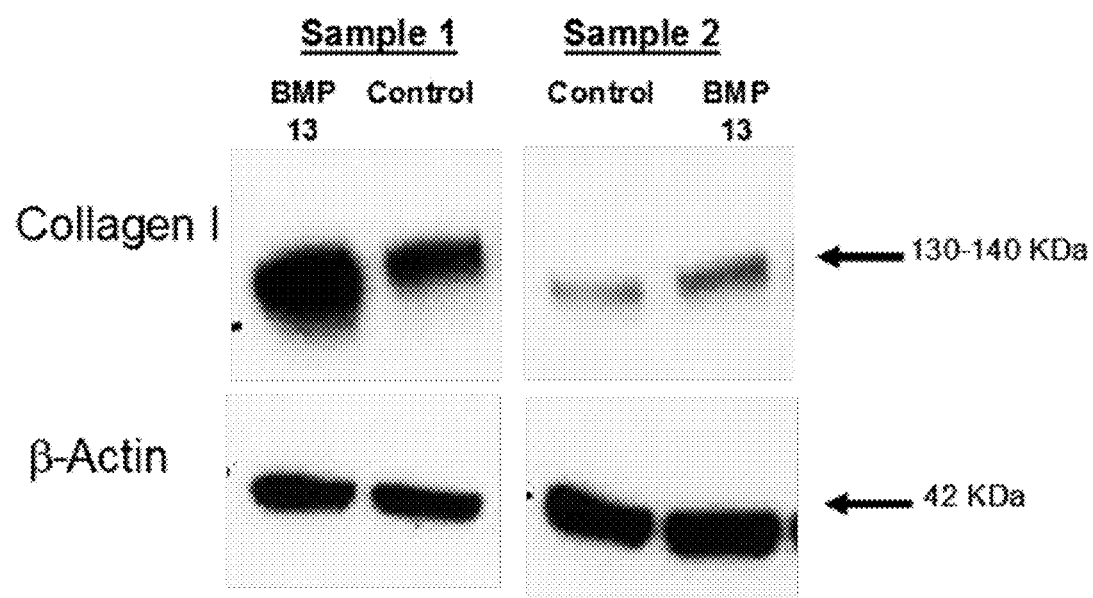
FIG. 21A is a copy of a photographic representation showing results of a Western blot experiment showing enhanced expression of collagen-1 in primary annulus fibrosus cell cultures. Cell cultures were stimulated with BMP13 (200 ng/mL) or media alone (control) for 7 days then analyzed by Western blot for collagen-1 expression. Data represents expression in 12.5 ug total protein per lane.
Figure 21B:
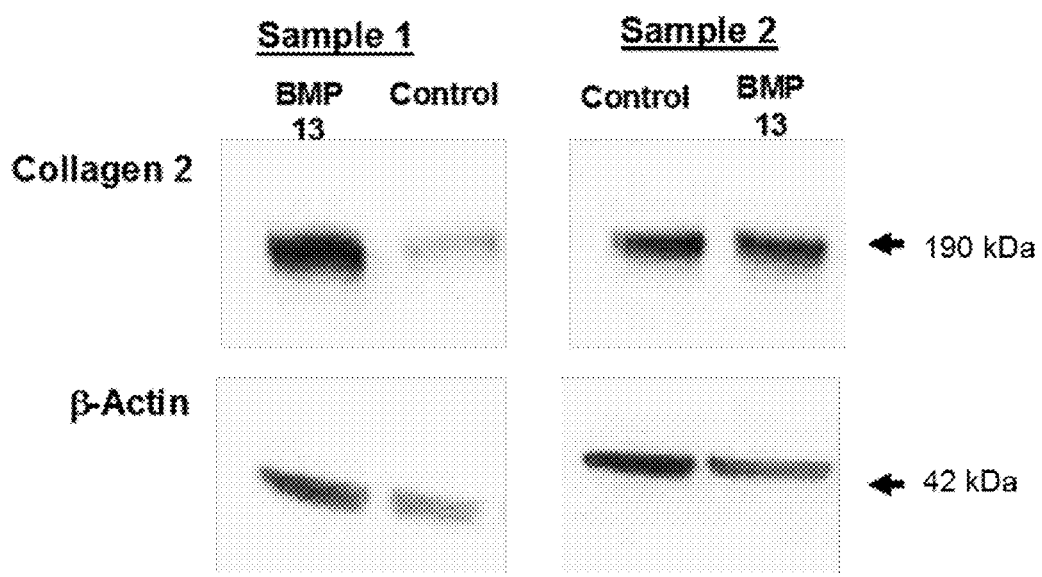
FIG. 21B is a copy of a photographic representation showing results of a Western blot experiment showing enhanced expression of collagen-2 in primary annulus fibrosus cell cultures. Cell cultures were stimulated with BMP13 (200 ng/mL) or media alone (control) for 7 days then analyzed by Western blot for collagen-2 expression. Data represents expression in 12.5 ug total protein per lane.
Figure 21C:
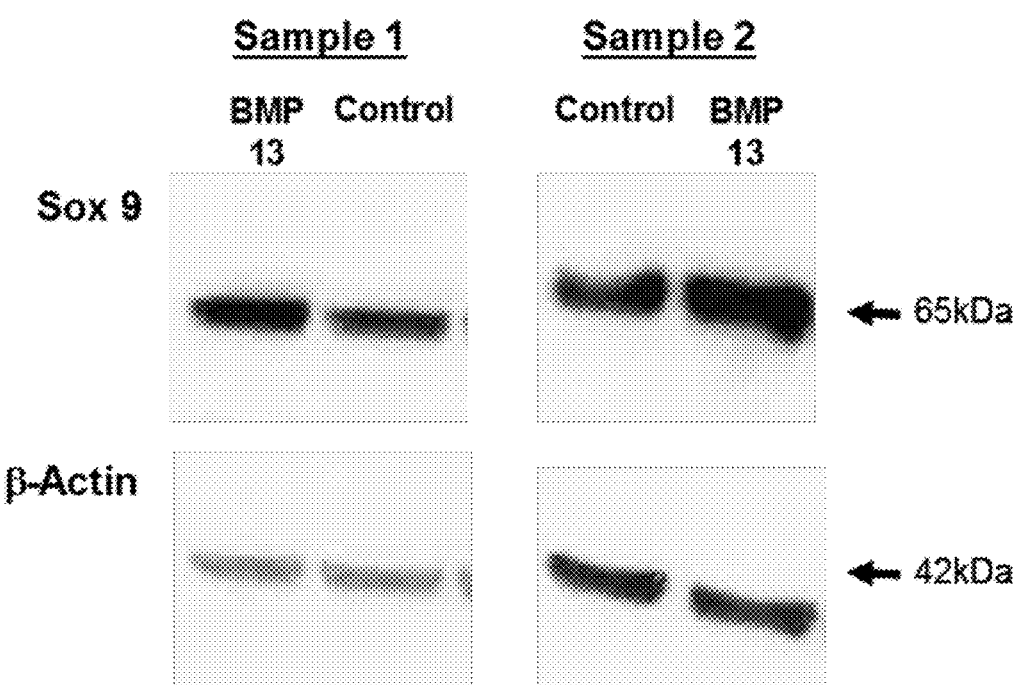
FIG. 21C is a copy of a photographic representation showing results of a Western blot experiment showing enhanced expression of SOX9 in primary annulus fibrosus cell cultures. Cell cultures were stimulated with BMP13 (200 ng/mL) or media alone (control) for 7 days then analyzed by Western blot for collagen-1 expression. Data represents expression in 12.5 ug total protein per lane.

Western blotting of cultured annulus fibrosus cells with GDF-6 demonstrated an increase in the production of collagen I, collagen II and SOX9 proteins by Western blot compared to the level observed in unstimulated cells (as shown in FIGS. 21A-21C). Accordingly, these results indicate that treatment of primary annulus fibrosus cells with GDF-6 increases expression of extracellular matrix proteins (e.g., collagen-1 and collagen-2) and a transcription factor that enhances expression of proteins involved in extracellular matrix synthesis (SOX9). In this respect, GDF-6 enhances production of the most common form of collagen in the annulus fibrosus, collagen-1.

Figure 21D:
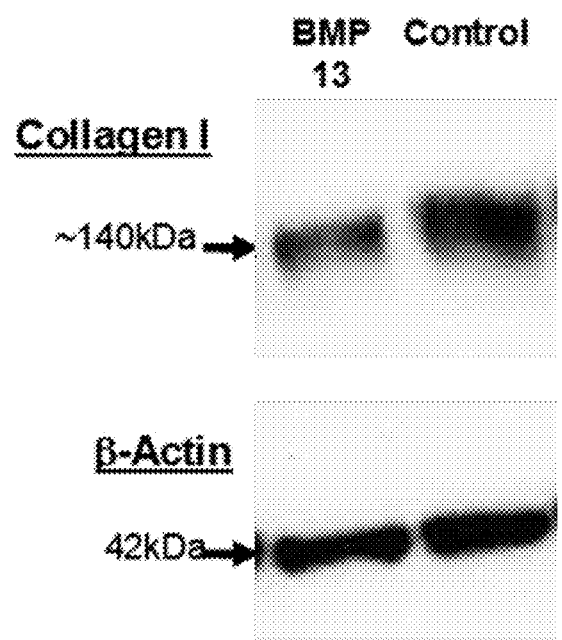
FIG. 21D is a copy of a photographic representation showing results of a Western blot experiment showing enhanced expression of collagen-1 in primary nucleus pulposus cell cultures. Cell cultures were stimulated with BMP13 (200 ng/mL) or media alone (control) for 7 days then analyzed by Western blot for collagen-1 expression. Data represents expression in 12.5 ug total protein per lane.
Figure 21E:
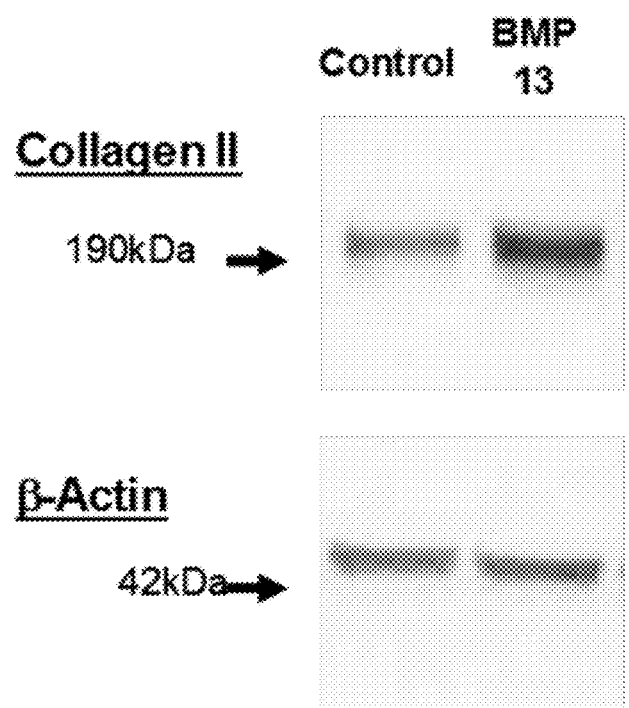
FIG. 21E is a copy of a photographic representation showing results of a Western blot experiment showing enhanced expression of collagen-2 in primary nucleus pulposus cell cultures. Cell cultures were stimulated with BMP13 (200 ng/mL) or media alone (control) for 7 days then analyzed by Western blot for collagen-2 expression. Data represents expression in 12.5 ug total protein per lane.
Figure 21F:
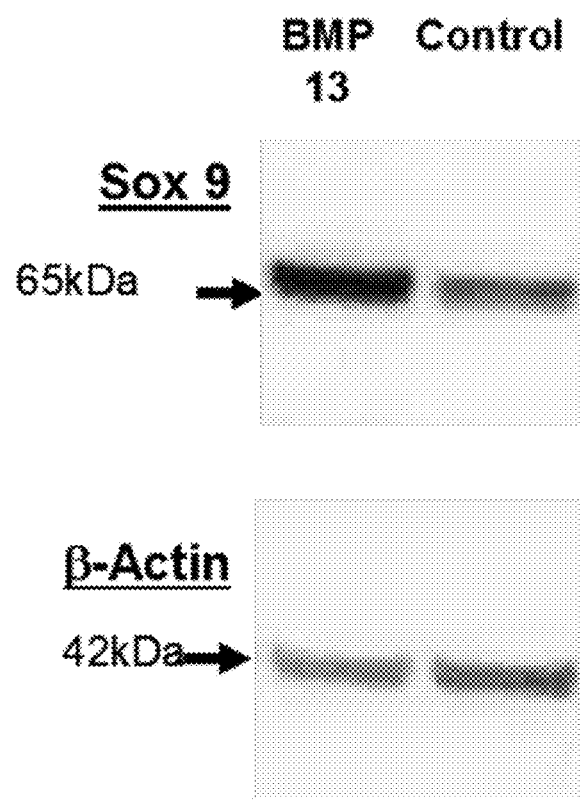
FIG. 21F is a copy of a photographic representation showing results of a Western blot experiment showing enhanced expression of SOX9 in primary nucleus pulposus cell cultures. Cell cultures were stimulated with BMP13 (200 ng/mL) or media alone (control) for 7 days then analyzed by Western blot for collagen-1 expression. Data represents expression in 12.5 ug total protein per lane.

As shown in FIGS. 21D-21F, GDF-6 enhances the level of expression of collagen-1, collagen-2 and SOX9 in primary nucleus pulposus cells. Accordingly, these results indicate that GDF-6 induces expression of extracellular matrix proteins, e.g., collagen-1 and collagen-2 and proteins involved in enhancing expression of extracellular matrix proteins, e.g., SOX9 in nucleus pulposus cells. As will be apparent from the foregoing description, the extracellular matrix of nucleus pulposus is reduced in a nucleus pulposus of a degenerating or degenerated IVD. Accordingly, these results indicate that GDF-6 is capable of inducing expression of proteins that can slow, reduce or prevent IVD degeneration and/or induce IVD regeneration.

Figure 21G:
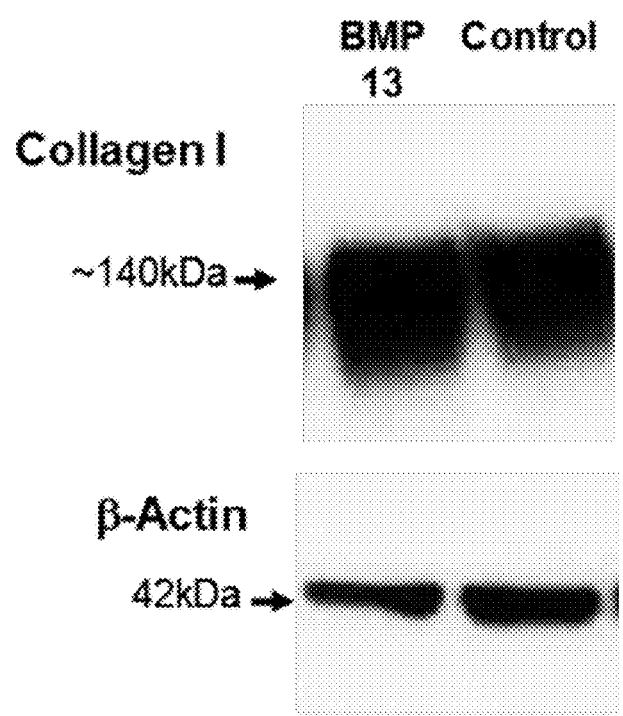
FIG. 21G is a copy of a photographic representation showing results of a Western blot experiment showing enhanced expression of collagen-1 in primary cultures of cells from IVD endplates. Cell cultures were stimulated with BMP13 (200 ng/mL) or media alone (control) for 7 days then analyzed by Western blot for collagen-1 expression. Data represents expression in 12.5 ug total protein per lane.
Figure 21H:
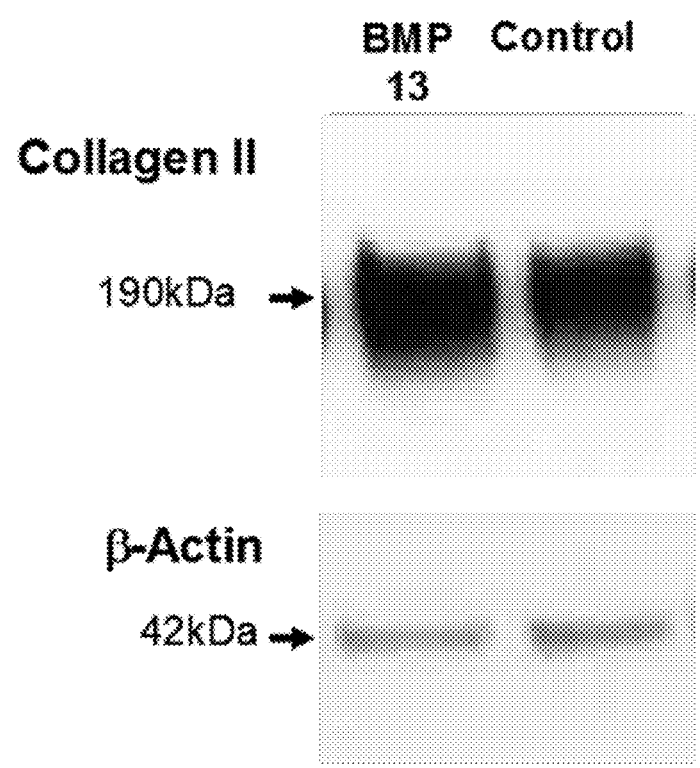
FIG. 21H is a copy of a photographic representation showing results of a Western blot experiment showing enhanced expression of collagen-2 in primary cultures of cells from IVD endplates. Cell cultures were stimulated with BMP13 (200 ng/mL) or media alone (control) for 7 days then analyzed by Western blot for collagen-2 expression. Data represents expression in 12.5 ug total protein per lane.
Figure 21I:
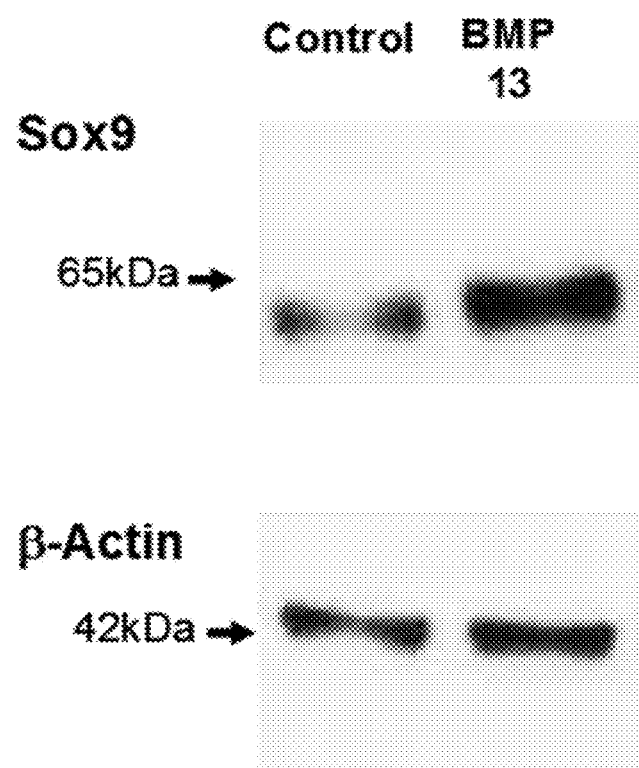
FIG. 21I is a copy of a photographic representation showing results of a Western blot experiment showing enhanced expression of SOX9 in primary cultures of cells from IVD endplates. Cell cultures were stimulated with BMP13 (200 ng/mL) or media alone (control) for 7 days then analyzed by Western blot for collagen-1 expression. Data represents expression in 12.5 ug total protein per lane.

FIGS. 21G-21I show the effect of GDF-6 on expression of collagen-1, collagen-2 or SOX9 in endplate cells. As shown, GDF-6 increases expression of each of these proteins in endplate cells.

The results described herein above and shown in FIGS. 21A-21I demonstrate that GDF-6 increases expression of proteins involved in extracellular matrix production, which are also markers of intervertebral disc cells and chondrocytes.

Example 14

Analysis of Expression of Extracellular Matrix Markers in Differentiated BM MSC Cells Cells are produced essentially as described in Example 13, and mRNA expression levels of collagen-1, collagen-2 and Aggrecan assessed as follows:

RNA Extraction from Cultured Cells

At regular times throughout experiments aliquots of cells are pooled together for quantitative real time RT-PCR to detect the level of mRNA's encoding components of extracellular matrix, specifically, aggrecan, collagen type-1 and type-2. RNA extraction from these pooled aliquots is performed with RNeasy Mini Kit (Qiagen, Hilden, Germany), as per manufacturer's instructions. The RNA concentration is then measured with a spectrophotometer at 260 nm with the additional 260 nm/280 nm readings taken for an indication of RNA purity. The isolated RNA preparation is then concentrated in a vacuum pump for 1 hour, reducing the volume to approximately 10 µl for the generation of concentrated RNA stocks.

Generation of cDNA from Isolated RNA (Reverse Transcription)

To completely remove residual DNA from the isolated RNA preparation, 1 µg of RNA is digested with Deoxyribonuclease I, Amplification Grade (Invitrogen) in a 10 µl reaction mixture comprising 1 µl 10× DNase buffer, 1 µl DNase and water for 15 minutes at room temperature. The digestion is inactivated with 1 µl of 25 mM EDTA for 10 minutes at 65° C. Purified RNA preparation was then reverse transcribed (RT) to produce cDNA with the ImProm-II™ Reverse Transcription System (Promega), as per manufacturer's instructions. Briefly, DNase digested RNA mixture (11 µl RNA) is added to 1 µl of Oligo(dT)$_{15}$ primers and incubated for 70° C. for 5 minutes, with a further 5 minutes incubation on ice. The mixture is kept on ice with a brief spin down to collect any condensation prior to adding the freshly made reverse transcriptase master mix consisting of 3.8 µl MgCl$_2$, 1 µl dNTP, 1 µl RT and 4 µl 5× buffer. The reaction mixture is then placed in a standard PCR machine for the generation of cDNA with the following program: 25° C. for 5 minutes, 42° C. for 60 minutes, 70° C. for 15 minutes; with the subsequent tubes of cDNA stored in a 4° C. refrigerator until use.

Real-Time SYBER Green Polymerase Chain Reaction

For real-time polymerase chain reaction (PCR), each reaction mix consists of 1 µl forward primer, 1 µl reverse primer, 12.5 µl Platinum® Syber® Green qPCR SuperMix UDG (Invitrogen) and 6.5 µl water made up into a master mix for the total number of reactions performed. The cDNA stock is diluted 1:2 for use in real time PCR reactions, with 4 µl of cDNA (1:2) added to 21 µl of master mix for each reaction, whereby triplicate reactions are set up for every sample by the CAS-1200 robotic liquid handling system (Corbett Robotics, Queensland, Australia). The sequences of the primers used for each gene of interest are as follows: collagen-type 1 forward primer AGACATCCCACCAATCACCT (SEQ ID NO: 26) and reverse primer AGATCACGTCATCGCACAAC (SEQ ID NO: 27); collagen-type 2 forward primer GTGACAAAGGAGAGGCTGGA (SEQ ID NO: 28) and reverse primer ACCTCTAGGGCCAGAAGGAC (SEQ ID NO: 29); aggrecan forward primer TCAACAACAATGCCCAAGAC (SEQ ID NO: 30) and reverse primer AAAGTTGTCAGGCTGGTTGG (SEQ ID NO: 31); house keeping gene, GAPDH forward primer AATCCCATCACCATCTTCCA (SEQ ID NO; 32) and reverse primer TGGACTCCACGACGTACTCA (SEQ ID NO: 33). Primer stocks are all adjusted to 50 µM concentrations, for use in the real time PCR reactions as described above. The completed reaction mixtures are then placed in a Rotor-Gene Thermal cycler (Corbett Research, Sydney, Australia) and a touchdown-PCR program is performed comprising two initial hold steps at 50° C. and 95° C. held at 2 minutes each, followed by 40 cycles of the PCR program: denaturation at 95° C. for 15 seconds, annealing and elongation temperature of 60° C. for 30 seconds. The resultant data generated are visualized, and a threshold at the exponential phase of amplification was set for the collection of cycle times of each gene in every sample tested for subsequent quantitative analysis of gene expression.

Relative Quantification of Gene Expression

Gene expression of protein stimulated-cells relative to the unstimulated cells is analyzed using the relative expression software tool (REST©) Statistical significance is determined by the pair wise fixed reallocation randomization test provided with the software.

Example 15

The Role of GDF-6 in Chondrogenic Differentiation of Bone Marrow Mesenchymal Stem Cells (BM MSCs)

Differentiation of BM MSCs

BM MSCs at Passage 3-4 were trypsinized using standard method for differentiation assays. For chondrogenic differentiation, MSCs at 1×106 cells/tube were centrifuged to form pellet or suspended in a solution of 1.2% (w/v) low viscosity sodium alginate in 150 mM NaCl, at the density of $5 \times 10^6$/ml. Alginate beads were formed by pressing the cell suspension dropwise into 102 mM $CaCl_2$ solution through a syringe with a needle. The beads formed instantly and were placed in 12-well plates after washing with 150 mM NaCl solution. Embedded MSCs were differentiated using standard induction medium containing 10 ng/ml of recombinant human TGF-β3 or 300 ng/ml of GDF-6 individually or in combination (TGF-β3&GDF-6). For cell recovery, the cell beads were washed twice in PBS and incubated in 55 mM of Na-citrate solution, pH 7.4 at 37° C. until beads were solubilized and the alginate was removed by centrifugation. Undifferentiated MSCs were cultured in parallel in growth medium as negative control. Cells were kept at 37° C., 5% CO2 for up to 21 days and the media were changed twice weekly.

RNA Extraction from Cultured Cells

At regular times throughout experiments aliquots of cells were pooled together for quantitative real time RT-PCR to detect the level of mRNA's encoding components of extracellular matrix, specifically, aggrecan, collagen type-1 and type-2. RNA extraction from these pooled aliquots was performed with RNeasy Mini Kit (Qiagen, Hilden, Germany), as per manufacturer's instructions. The RNA concentration was then measured with a spectrophotometer at 260 nm with the additional 260 nm/280 nm readings taken for an indication of RNA purity. The isolated RNA preparation was then concentrated in a vacuum pump for 1 hour, reducing the volume to approximately 10 µl for the generation of concentrated RNA stocks.

Generation of cDNA from Isolated RNA (Reverse Transcription)

To completely remove residual DNA from the isolated RNA preparation, 1 µg of RNA was digested with Deoxyribonuclease I, Amplification Grade (Invitrogen) in a 10 reaction mixture consisting of 1 µl 10× DNase buffer, 1 µl DNase and water for 15 minutes at room temperature. The digestion was inactivated with 1 µl of 25 mM EDTA for 10 minutes at 65° C. Purified RNA preparation was then reverse transcribed (RT) to produce cDNA with the ImProm-II™ Reverse Transcription System (Promega), as per manufacturer's instructions. Briefly, DNase digested RNA mixture (11 µl RNA) was added to 1 µl of Oligo(dT)$_{15}$ primers and incubated for 70° C. for 5 minutes, with a further 5 minutes incubation on ice. The mixture was kept on ice with a brief spin down to collect any condensation prior to adding the freshly made reverse transcriptase master mix consisting of 3.8 µl $MgCl_2$, 1 µl dNTP, 1 µl RT and 4 µl 5× buffer. The reaction mixture was then placed in a standard PCR machine for the generation of cDNA with the following program: 25° C. for 5 minutes, 42° C. for 60 minutes, 70° C. for 15 minutes; with the subsequent tubes of cDNA stored in a 4° C. refrigerator until use.

Real-Time SYBER Green Polymerase Chain Reaction

For real-time polymerase chain reaction (PCR), each reaction mix consisted of 1 µl forward primer, 1 µl reverse primer, 12.5 µl Platinum® Syber® Green qPCR SuperMix UDG (Invitrogen) and 6.5 µl water made up into a master mix for the total number of reactions performed. The cDNA stock was diluted 1:2 for use in real time PCR reactions, with 4 µl of cDNA (1:2) added to 21 µl of master mix for each reaction, whereby triplicate reactions were set up for every sample by the CAS-1200 robotic liquid handling system (Corbett Robotics, Queensland, Australia). Primers were used to amplify cDNA produced from transcripts of markers of chondrogenic cells (collagen II, aggrecan and Sox9). Primer stocks were all adjusted to 50 µM concentrations, for use in the real time PCR reactions as described above. The completed reaction mixtures were then placed in a Rotor-Gene Thermal cycler (Corbett Research, Sydney, Australia) and a touchdown-PCR program was performed consisting of two initial hold steps at 50° C. and 95° C. held at 2 minutes each, followed by 40 cycles of the PCR program: denaturation at 95° C. for 15 seconds, annealing and elongation temperature of 60° C. for 30 seconds. The resultant data generated were visualized, and a threshold at the exponential phase of amplification was set for the collection of cycle times of each gene in every sample tested for subsequent quantitative analysis of gene expression.

Relative Quantification of Gene Expression

Gene expression of protein stimulated-cells relative to the unstimulated cells was analyzed using the relative expression software tool (REST©) Statistical significance was determined by the pair wise fixed reallocation randomization test provided with the software.

Results

Figure 22A:
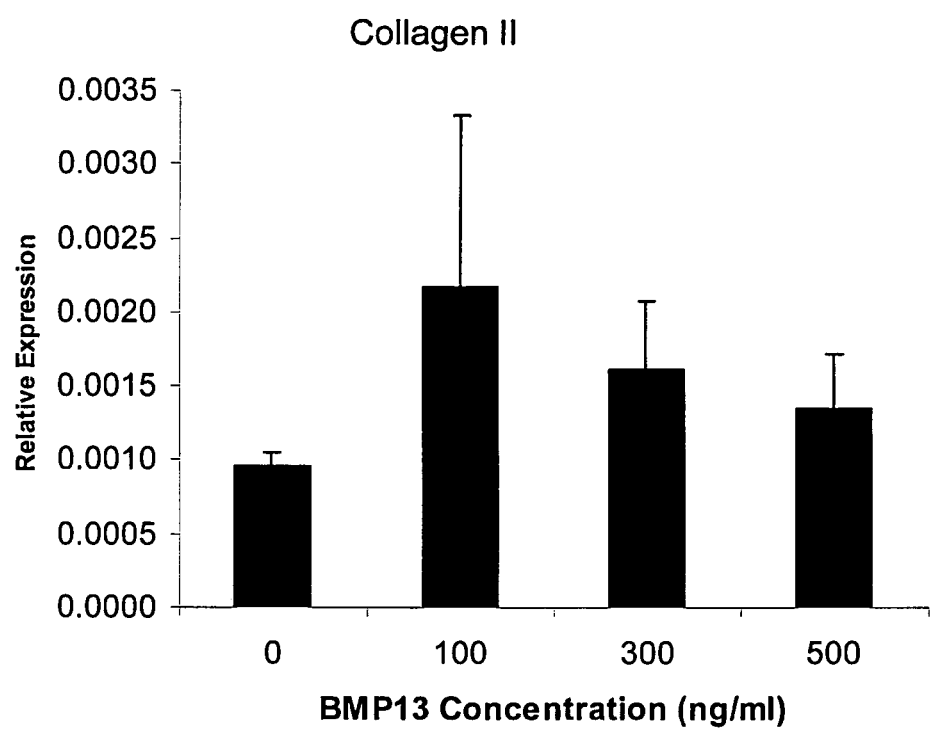
FIG. 22A is a graphical representation showing the level of expression of the chondrogenic marker collagen II at the mRNA level in BM MSC cells and cells differentiated therefrom incubated in the presence of various concentrations of GDF-6 (GDF-6) as indicated on the X-axis. Expression levels were detected using real time quantitative PCR. Relative expression is indicated on the Y-axis.
Figure 22B:
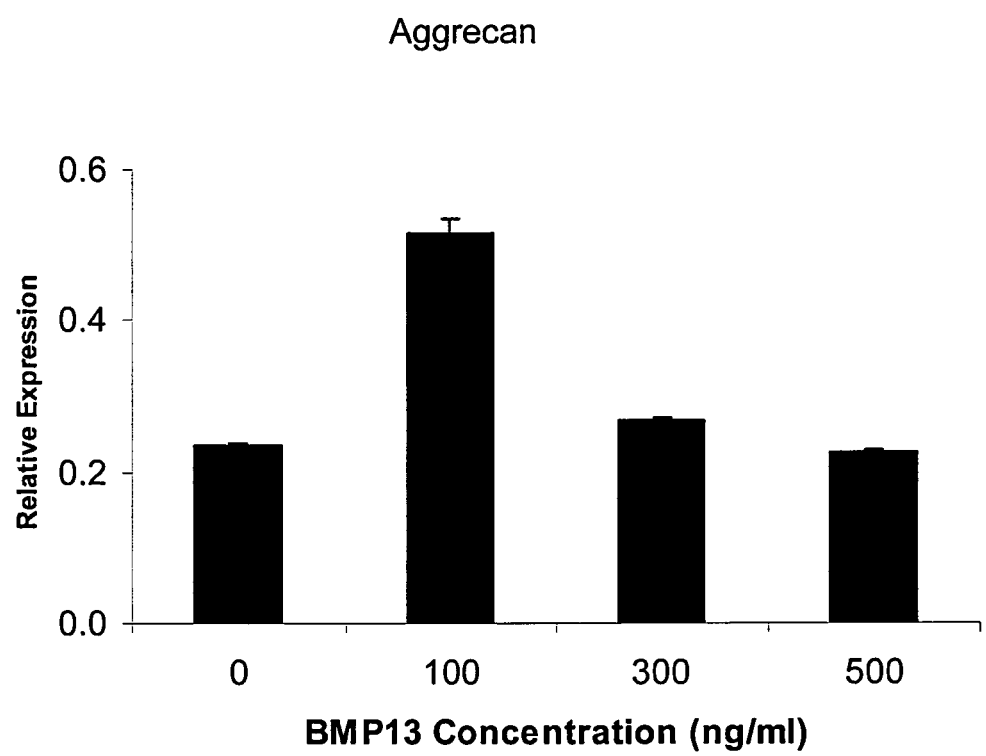
FIG. 22B is a graphical representation showing the level of expression of the chondrogenic marker Aggrecan at the mRNA level in BM MSC cells and cells differentiated therefrom incubated in the presence of various concentrations of GDF-6 (GDF-6) as indicated on the X-axis. Expression levels were detected using real time quantitative PCR. Relative expression is indicated on the Y-axis.
Figure 22C:
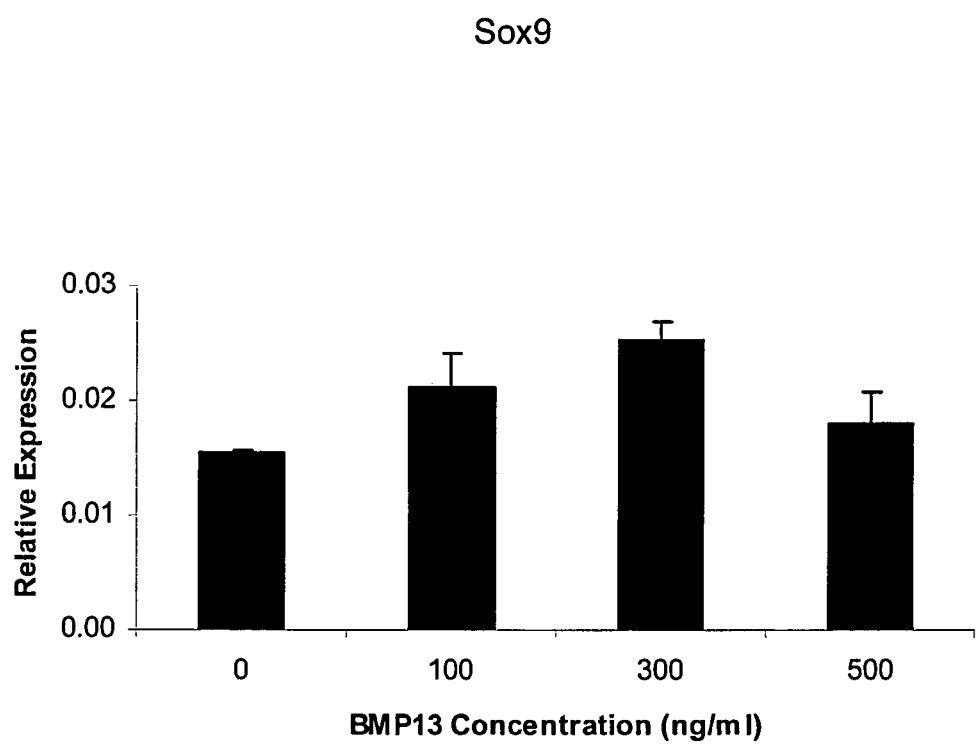
FIG. 22C is a graphical representation showing the level of expression of the chondrogenic marker Sox9 at the mRNA level in BM MSC cells and cells differentiated therefrom incubated in the presence of various concentrations of GDF-6 (GDF-6) as indicated on the X-axis. Expression levels were detected using real time quantitative PCR. Relative expression is indicated on the Y-axis.

As shown in FIGS. 22A-22C GDF-6 induces expression of chondrogenic genes collagen II, Aggrecan and Sox9. These data indicate that GDF-6 is capable of inducing BM MSCs to differentiate into chondrogenic-like cells. For example, a concentration of 100 ng/ml of GDF-6 (GDF-6) increases expression of Aggrecan, and a concentration of at least 100 ng/ml increases expression of Sox9.

Example 16

Effect of BMP13 on Migration and Growth of Human Bone Marrow Mesenchymal Stem Cells (BM-MSC) In Vitro Gene Expression Analysis BM MSC were cultured in expansion media and harvested at passage 2 and mRNA prepared for analysis of gene expression levels using real-time PCR. BMP2, 7 and 13 were detected at day 1, 3, 5, and 7 of culture and expressed relative to the house-keeping genes GAPDH and HPRT.

Cell Migration Assays

Cultured human BM-MSC were harvested from flasks by trypsin digestion and resuspended in DMEM/0.1% FBS before seeding (2×104 cells/well) in collagen IV-(Sigma) coated transwells (Costor 3422). Cells were allowed to settle (incubation 30 minutes) then 600 µl of media containing 0, 100, 300 or 500 ng/mL rhGDF-6 (Peprotech) was added to the lower chambers of the transwells. Following overnight (12-16 h) incubation, transwell membranes were washed, cells were fixed and stained, and the total number of migrated cells (on the bottom face of the membrane) was determined Cell Growth Assays Human BM MSCs were seeded in culture flasks (duplicates) at 2000 cells/cm2 and treated with 0, 100, 300 and 500 ng/ml of recombinant human GDF-6 for 3 or 6 days. Following treatment, cells were trypsinized, collected at each time point and counted by trypan blue exclusion method under a hemocytometer. The total cell number was used for comparison between GDF-6 treated and untreated BM MSCs.

Results

Figure 23:
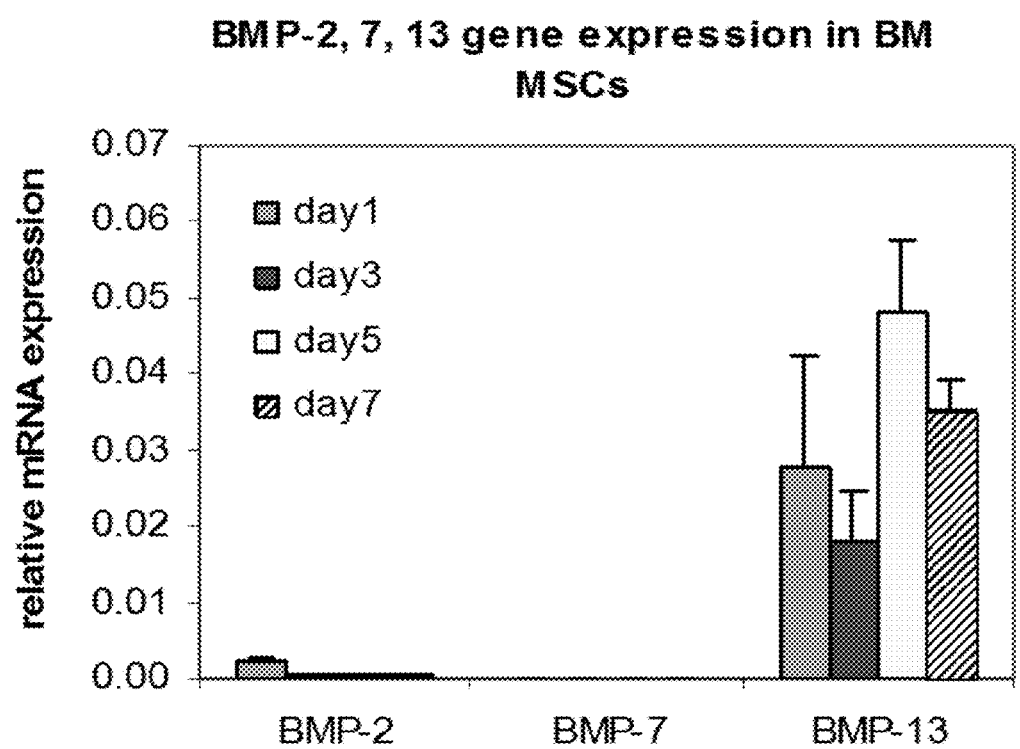
FIG. 23 is a graphical representation showing the level of expression of BMP-2, BMP-17 or GDF-6 (GDF-6) as indicated in bone marrow mesenchymal stem cells (BM MSCs) after 1, 3, 5 and 7 days (as indicated). Results are expressed relative to standard, constant, house-keeping genes GAPDH and HPRT.

Expression of BMPs 2 and 7 and GDF-6 genes were detected in cultured human BM MSC at day 1, 3, 5 and 7 (as shown in FIG. 23). At all time points GDF-6 was expressed at higher levels than the other BMPs, peaking at day 5.

Figure 24:
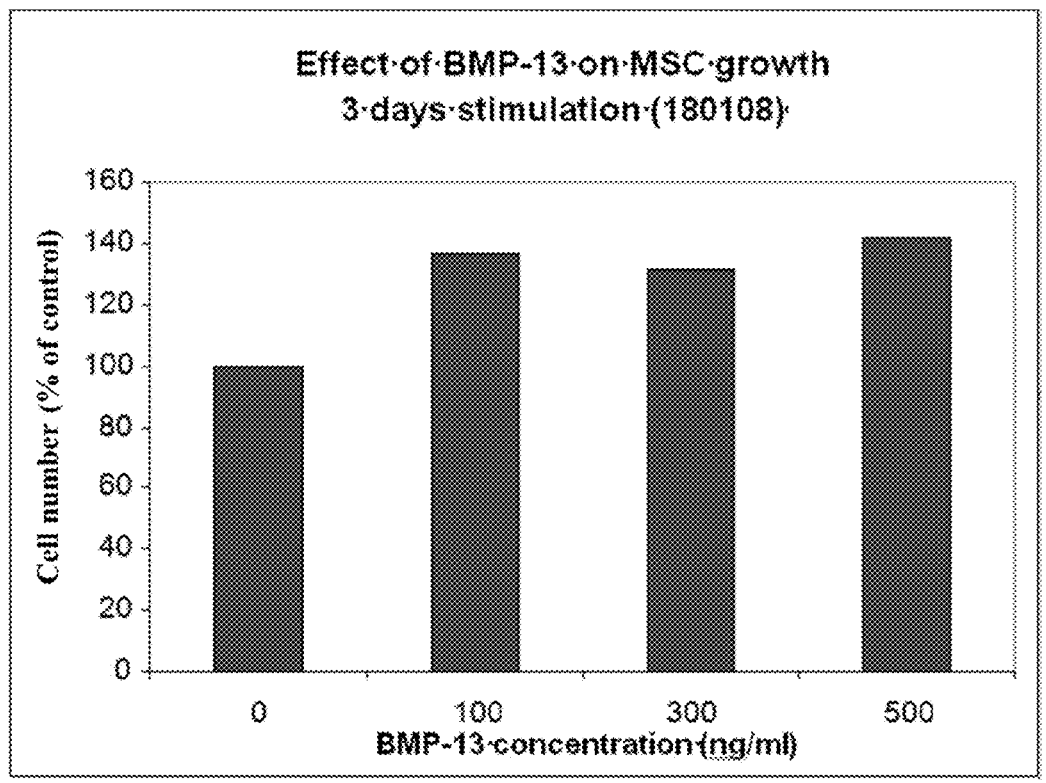
FIG. 24 is a graphical representation showing the number of cells in BM MSC cultures incubated in increasing concentrations of GDF-6 (as indicated). Results are expressed as a percentage of control cultures containing no GDF-6 stimulation.

Culture of MSC in the presence of human BMP13 at all concentrations tested resulted in greater cell numbers than media alone (FIG. 24). Cell numbers did not appear to be greater with increasing dose in the range 100-500 ng/mL. Thus BMP13 can stimulate increased growth of mesenchymal progenitor cells.

Figure 25:
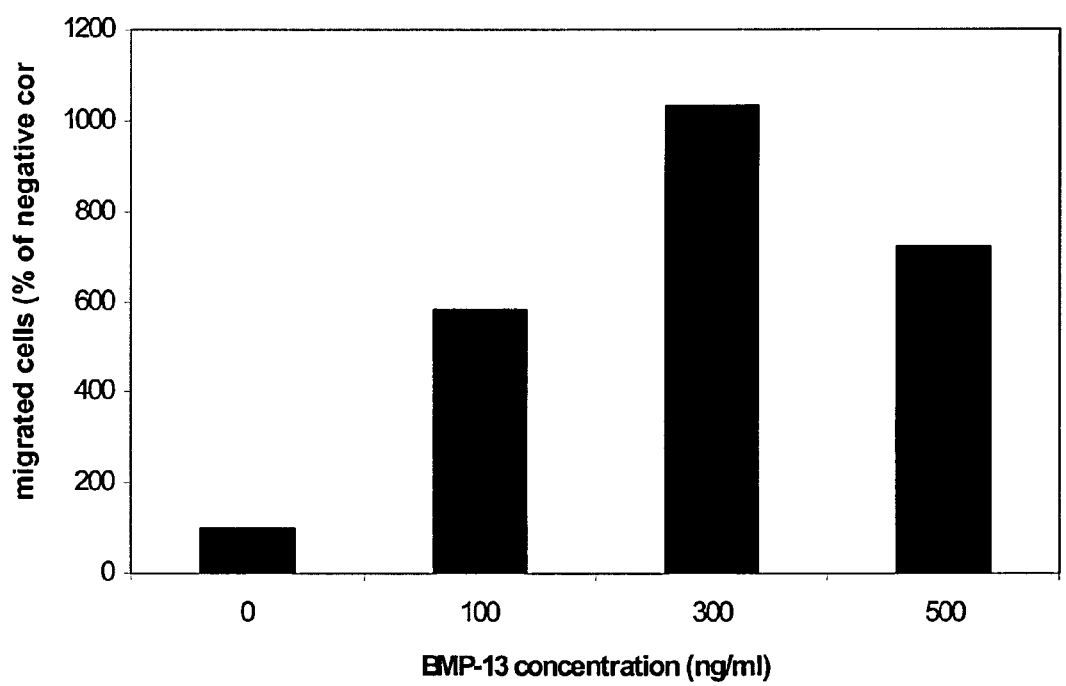
FIG. 25 is a graphical representation showing results of cell migration assays following incubation with or without increasing quantities of GDF-6 (as indicated). Cell counts are expressed as a percentage of negative control wells (containing no GDF-6).

The presence of GDF-6 in the lower chamber of BM MSC transwell cultures induced the migration of MSC towards the source of the GDF-6 (FIG. 25). This indicates that GDF-6 acts as a chemoattractive agent for BM-MSC cells. The number of cells migrating towards the GDF-6 appear to follow a dose response, with 300 ng/mL inducing maximum migration.

These results indicate that GDF-6 is expressed in BM MSC cultures at a higher level than BMP2 or BMP7, perhaps indicating increased importance in progenitor cell function. GDF-6 also appears to stimulate cell growth in BM MSC cultures at 100 ng/mL and to act as a chemottractive agent for BM-MSC cells. Chemoattraction was dose dependent, peaking at 300 ng/mL.

Example 17

Expression of MSX1 and/or MSX2 in IVD Cells

Adenovirus Carrying Expression Constructs Encoding MSX1 or MSX2

Adenovirus carrying a cDNA encoding MSC1 or MSX 2 are produced by Applied Biological Materials (ABM) Inc.

Isolation and Transduction of IVD Cells

Surgically discarded human disc tissues are categorized by the grade of degeneration as well as the age of the patent. Cells are visually separated into annulus fibrosus or nucleus puplosus cells.

Harvested cells are maintained and transduced with adenovirus carrying the expression construct encoding MSX1 and/or MSX2 in both monolayer and 3D-alginate cultures to obtain more comprehensive data regarding cells under active proliferation (monolayer) and in more physiological settings (3D-alginate).

Post-transfection, cells are harvested at 24, 48 and 72 hours, 1, 2 and 4 week time points to enable the analysis of the beneficial effects MSX 1 or 2 has on discal cells in vitro using the assays described below.

Cell Proliferation Studies

To determine the effect of MSX 1/2 on cellular proliferative capacity, periodic cell counts are performed at each cellular passage between transfected and non-transfected controls. A graphical representation of cell numbers depicts an accumulated growth curve over time for each of the groups. Additionally, DNA synthesis is assessed as a measure of mitotic activity using Cell Proliferation ELISA, BrdU (Chemiluminescence) kit, Roche Applied Science (Australia).

Cell Viability Studies

To ensure Ad-MSX 1/2 has no cellular toxicity effects in vitro viability assays are performed with Celltiter 96 Aqueous One Solution, Cell Proliferation assay, Promega.

Secondly, anti-apoptotic ability of Ad-MSX-1/2 is tested by TNF-α- or IL-1-induced apoptosis of cells prior to Ad-MSX 1/2 transfection with the subsequent measurements of cellular viability (as described above) and apoptosis (In Situ Cell Death Detection Kit, Apoptotic DNA Ladder Kit and Annexin-V-FLUOS Staining Kit, Roche).

In vivo discal cells are often in hypoxic environments whereby low oxygen content is common even in normal discs. To detect the extent of protection by Ad-MSX-1/2 under hypoxic conditions transfected cells are incubated in 2-5% $O_2$ levels, which is representative of physiological oxygen levels in normal to degenerated discs. The level of cellular apoptosis is then determined as described supra. The level of extracellular matrix synthesis is also determined as described infra.

Cell Synthetic Activities

The effects of Ad-MSX-1/2 on cellular synthetic activity is detected at both the mRNA and protein levels. TaqMan™ real-time RT-PCR is performed with primers and probes for Aggrecan, Collagen 1 and Collagen 2 specifically designed by Applied Biosystems. The protein levels are detected by aggrecan, collagen-1 and collagen-2 antibody detection through flow cytometry and immunohistochemistry.

Example 18

Differentiation of BM MSCs into Nucleus Pulposus-Like Cells Using GDF-6

Tissue Samples

Human bone marrow is collected from iliac crest of 6 haematologically normal donors (age 27-64). Human IVD tissue is collected from 8 patients (age 18-46) undergoing lumbar disc replacement. The nucleus pulposus tissue is immediately separated from annulus fibrosus after surgery. Half of the nucleus pulposus tissue is used for RNA extraction and the other half for nucleus pulposus cell isolation.

Cell Isolation and Cultivation

BM MSCs are isolated by immunodepletion, Ficoll-Paque density gradient centrifugation and plastic adhesion essentially as described in Tao et al., *Dev. Growth Differ.*, 47: 423-433, 2005. Briefly, fresh bone marrow specimens are incubated for 20 min with an antibody cocktail available from StemCell Technologies (Vancouver, Canada) to remove mature lineage-committed cells. Ficoll-Paque (GE Healthcare, Uppsala, Sweden) density gradient centrifugation is then performed to separate mononuclear cells from antibody cross-linked cells and enriched cells from the interface are seeded in plastic culture ware. The cells are cultured in growth medium (essentially as described in Tao et al., supra) comprising of about 51% Dulbecco's Modified Eagle's Medium—low glucose (DMEM-LG), 10% fetal bovine serum (FBS; Invitrogen, Carlsbad, Calif., USA), about 34% MCDB-201 medium, 1% insulin transferrin selenium (ITS), 1% linoleic acid/bovine serum albumin (BSA), 1 nM dexamethasone, 32 µg/ml ascorbic acid 2-phosphate (Sigma-Aldrich, St. Louis, Mo., USA) and incubated at 37° C. with 5% $CO_2$. After about 3 days, non-adherent cells are discarded and adherent BM MSCs were cultured to about 80% confluence with medium changed twice weekly.

Nucleus pulposus cells are isolated by overnight digestion with 0.025% collagenase solution and collected by centrifugation. Nucleus pulposus cells are cultured in DMEM-LG medium containing about 32 µg/ml ascorbic acid 2-phosphate and 10% FBS. Passage 0 cells are used as positive control cells in the experiments described below.

Flow Cytometry Analysis

MSCs are trypsinized and washed with PBS containing 10% FBS and incubated with human AB plasma at 4° C. for 30 min. After washing with FACS buffer (PBS containing 13.6 mM Tri-sodium citrate and 1% BSA), MSCs ($1 \times 10^5$ per tube) are resuspended in 50 µl FACS buffer and labeled with 5 µl of fluorescein isothiocyanate (FITC), phycoerythrin (PE) or peridinin chlorophyll protein (PerCP) conjugated monoclonal antibodies in dark at 4° C. for 30 min. Antibodies used include anti-CD29, anti-CD73, anti-CD45, anti-CD14, anti-CD34, anti-CD166, anti-HLA Class I, anti-HLA Class II (BD Biosciences Pharmingen, San Jose, Calif., USA), anti-CD44 and anti-CD105 (Chemicon, Temecula, Calif., USA). The cells are analyzed on a FACSCalibur flow cytometer (BD Biosciences).

Chondrogenic Differentiation in Alginate Bead 3D Culture

MSCs at Passage 3-6 are trypsinized and suspended in a solution of about 1.2% (w/v) low viscosity sodium alginate in 150 mM NaCl, pH 7.4, at the density of $5 \times 10^6$/ml for differentiation and $1 \times 10^6$/ml for undifferentiated control. Alginate beads are produced by gently pressing the cell suspension dropwise into 102 mM $CaCl_2$ solution through a syringe with a 19 G needle. The hydrogel beads formed instantly and are placed in 12-well plates after washing 3 times with 150 mM NaCl solution.

Chondrogenic differentiation is induced by adding serum-free media containing DMEM-high glucose supplemented with 100 nM dexamethasone, 50 µg/ml ascorbate 2-phosphate, 40 µg/ml L-proline, 1.25 mg/ml BSA, 5.35 µg/ml linoleic acid, 1% ITS solution and recombinant GDF-6 or an active fragment thereof produced as described in Example 10 optionally combined with recombinant human (rh) TGF-β3 or combined with rhTGF-β3 and rhBMP-2 (TGF-β3&BMP-2, R&D Systems, MN, USA), or cells are incubated with rhTGF-β3 in the absence of GDF-6 or the active fragment. Undifferentiated MSCs are cultured in parallel in growth medium. Cells are kept at 37° C., 5% $CO_2$ for up to 21 days. The media are changed twice weekly. For cell recovery, the cell beads are washed twice in PBS and incubated in 55 mM of Na-citrate solution, pH 7.4 at 37° C. for 10 min. The solubilized alginate is removed by centrifugation and the cell pellet was washed with PBS.

RNA Extraction, cDNA Synthesis and Real-Time PCR

Total RNA is isolated from MSCs, nucleus pulposus tissue and cultured nucleus pulposus cells using TRIzol reagent (Invitrogen) and RNeasy kit (Qiagen, Dusseldorf, Germany) essentially according to manufacturers' instructions. Copy DNA (cDNA) is prepared using SuperScript III first-strand synthesis system (Invitrogen) essentially according to manufacturer's instructions. Briefly, total RNA (1 µg) is reverse transcribed in a final volume of 20 µl using M-MLV reverse transcriptase (200 units) and a mixture of random hexamers (50 ng) and Oligo(dT)20 (50 pmol) as primers. Samples are incubated at 25° C. for 10 min, 50° C. for 50 min and then heated to 85° C. for 5 min. A dilution of the resulting cDNA is used in 20 µl-reactions for real-time PCR analysis in a Rotor-Gene RG3000 system (Corbett Life Science, Sydney). Primers to amplify transcripts from genes encoding collagen-2, aggrecan and Sox-9, which are markers of chondrocytic cells are designed using published mRNA sequences. To exclude possible genomic DNA contamination, the RNA is treated with DNase and primers are designed to be intron-spanning. The thermal profile for all reactions was as follows: 5 min at 95° C., followed by 40 amplification cycles of 15 sec at 95° C., 30 sec at 60° C. and 30 sec at 72° C. Relative expression levels are calculated as a ratio to the average value of house-keeping genes, glyceraldehyde-3-phosphate dehydrogenase (GAPDH) and hypoxanthine phosphoribosyltransferase 1 (HPRT1).

Histology and Immunohistochemistry

Alginate beads encapsulated with MSCs are fixed in 10% neutral buffered formalin for 1 h and embedded in paraffin. Sections of 4 µm thickness are cut and mounted on Super Plus slides (Lomb Scientific, Australia). Sections are dewaxed in xylene and hydrated with graded ethanol before staining. Hematoxylin-eosin (H&E) staining is carried out for general histological examinations. For Alcian blue staining, slides are stained in 1% Alcian blue solution for 15 min and nuclei are counterstained with 0.1% nuclear fast-red solution. For immunohistochemical staining, slides are equilibrated in Tris-HCl (pH 7.6) buffer. Endogenous peroxidases are scavenged with 3% (v/v) $H_2O_2$ and non-specific binding is blocked by incubation in 10% skim milk in Tris-HCl buffer. Sections are incubated with primary goat anti-human type II collagen polyclonal antibodies or goat anti-human SOX9 polyclonal antibodies (Santa Cruz Biotechnology, CA, USA) or mouse-anti-human collagen-2 monoclonal antibody for 1 h at room temperature. Slides are treated with MULTILINK solution (DAKO, Australia) followed by streptavidin-conjugated peroxidase incubation. The sections are visualized with 3,3'-diaminobenzidine hydrochloride solution and counterstained with Haematoxylin. The primary antibody is omitted for the negative controls.

Western Blot Analysis

Cells are rinsed with cold PBS and lysed in CelLytic-M solution containing protease inhibitors (Sigma-Aldrich). Equal amount of proteins are electrophoresed on 8-12% gradient SDS-polyacrylamide gels (Invitrogen). Proteins are transferred by electroblotting to PVDF membranes, which are then blocked with 5% skim milk in Tris-HCl buffered saline (TBS; 20 mM Tris, pH 7.6, 0.15 M NaCl) overnight at 4° C. Membranes are incubated with goat anti-human type II collagen or rabbit anti-human SOX9 polyclonal antibodies (Santa Cruz Biotechnology) in TBS buffer containing 0.1% Tween-20 (TTBS) for 2 h at room temperature. Alpha-tubulin or β-actin is detected as reference protein. After washing and incubation with fluorescent dye-conjugated secondary antibodies, immunolabeling is detected using the Odyssey infrared imaging system (LI COR Biosciences, Nebraska, USA). Alternatively, bound antibodies are labeled with an anti-goat horseradish peroxidase-conjugated secondary antibody. Following washing the resulting antibody complexes are detected using the Super Signal Chemilumnescent Substrate System (Pierce) as per manufacturer's instructions.

35S-Sulfate Incorporation

The cell function of differentiated MSCs is investigated in vitro by detecting the biosynthesis of proteoglycans using 35S-sulfate incorporation assay essentially as described in Collier et al., *Ann. Rheum. Dis.*, 48: 37-381, 1989. Briefly, the alginate beads containing differentiated MSCs are incubated with 20 mCi/well of $^{35}$S-sulfate (GE Healthcare) at 37° C. for 24 h. Following release from alginate beads, the cells are harvested and resuspended in papain digestion buffer containing 2 μl of papain suspension per 1 ml of PBS, pH 6.2, 5 mM L-cysteine and 10 mM EDTA at 60° C. for 3 h to release glycosaminoglycans. An aliquot is separated for DNA determination. Newly synthesized $^{35}$sulfated glycosaminoglycans are separated from free $^{35}SO_4$ by a precipitation procedure. Samples are then counted in an automated Scintillation Analyzer and normalized by DNA concentration. The fold change of relative counts represents the change in proteoglycan synthesis.

Results

Results showing that cells incubated in the presence of GDF-6 or an active fragment thereof express increased levels of collagen-2 and aggrecan and Sox9 compared to undifferentiated MSCs indicate that GDF-6 or the active fragment thereof induce MSCs to differentiate into a nucleus pulposus chondrocytic lineage.

Results showing increased production of proteoglycans, e.g., increased $^{35}SO_4$ production and/or increased collagen-2 and/or Sox9 protein expression indicate that GDF-6 or the active fragment thereof induce MSCs to differentiate into a nucleus pulposus chondrocytic lineage.

Moreover, results indicating similar levels of expression of transcripts in isolated nucleus pulposus cells and in treated cells indicate that GDF-6 or the active fragment thereof induce MSCs to differentiate into a nucleus pulposus chondrocytic lineage.

Example 19

Treatment of a Sheep Model of IVD Degeneration with Stem Cells

Sheep are be purchased from the University farm, Arthursleigh, Australia, and transported to a veterinary centre a minimum of 2 weeks prior to first experimental procedure and housed in a paddock. Each sheep is premedicated with 0.3 mg/kg diazepam and individually taken to the anesthesia induction area immediately prior to the surgical procedure. The jugular vein is catheterized using a 16 G×3.25 cm catheter after local anesthetic is placed under skin using a syringe and 25 gauge needle. Sheep are anaesthetized with 10 mg/kg ketamine given to effect. The sheep are placed in right lateral recumbency and the right caudal quarter of the sheep clipped and aseptically prepared. A straight incision a few finger-breadths below the costal margin and parallel to lateral border of the erector spinae muscles is made to allow exposure of the lower lumbar vertebrae (L2 to L6). The approach is made retroperitoneally using electrocautery to divide the subcutaneous tissue, fascia, and thoracolumbar aponeurosis and transversalis fascia in line with the skin incision, the peritoneum is protected and reflected anteriorly by blunt dissection. A retractor is placed between rostral and the iliac crest to aid exposure. The vertebral bodies from L3 to L5 are identified and, with a Deaver retractor, the vessels lying anterior to the spine are protected. Once the appropriate involved vertebra is identified, the psoas muscle is elevated bluntly off the lumbar vertebrae and retracted laterally to the level of the transverse process with a Richardson retractor. Bipolar coagulation of vessels around the vertebrae is also performed. The fibrosus annuli of anterolateral discs of L2 to L5 are identified. Annular fibrosus of two non-contiguous lumbar discs per animal. The incision of fibrous annulus is made to a 6 mm depth using a #9 B-P knife blade. The IVD located between the two punctured IVDs is used as a control. A 27 mm×10 mm titanium screw is implanted into the vertebral body at one level for later identification of levels. One of the punctured levels will is treated with stem cells produced according to Example 18, optionally transfected with a nucleic acid encoding full-length GDF-6 or an active domain thereof produced essentially as described in Example 10, and the other punctured disc treated with saline control. In both cases the treatment is injected into the nucleus pulposus of punctured discs. After completion of procedure, the wound is closed in layers.

Radiographs (lateral only) are taken prior to waking of animals. Two weeks after surgery and monthly thereafter, radiography are performed on the assigned sheep using 0.3 mg/kg diazepam and 0.2 mg/kg butorphanol intravenously for sedation. The remaining radiographs and CT scans are performed after euthanasia on the assigned days (3 month, 6 months and 18 months). Disc height is also raidographically determined on a monthly basis (lateral view only) and following euthanasia. IVD height is expressed as a disc height index (DHI). The level of degeneration based on the Thompson grade (1=normal, 4=severely degenerated) is also assessed using MRI.

Following three, six or eighteen months, sheep are euthanized using an overdose of pentobarbitone administered intravenously. After euthanasia the sheep undergo a post-mortem examination and IVDs.

Lumbar vertebral joints are biomechanically tested using an Instron 8874 in 4 modes. Range of motion, constraint to motion, and hysteresis will be quantified for the treated joints and compared to controls. Annular tissue samples from treated joint levels and controls are be isolated and tested in tension to determine ultimate strength and tensile modulus.

Disc tissue collected post-mortem is subject to histological analysis to assess the level of disc degeneration. Spines are removed surgically and muscle tissue removed before being submerged in working formalin solution (10% in 0.1M Phosphate buffer). Spines are labeled according to head/tail orientation. After initial fixation, spines are segmented into individual discs labeled +2, +1, −1, −2 in relation to the position of the titanium screw inserted at surgery, and thus identifiable in respect of the treatment administered. Discs are then submerged in de-calcifying solution overnight with agitation to soften bone tissue. Individual discs are sectioned into pieces of tissue no more than 5 mm thick, placed in cassettes for paraffin embedding and thin sectioning. Tissues are then stained with haematoxylin/eosin for tissue architecture analysis.

We claim:

1. A method for preventing or treating intervertebral disc (IVD) degeneration in a subject having IVD damage, said method comprising
administering a human GDF-6 comprising a dimer comprising a C-terminal fragment of at least 120 amino acid residues of SEQ ID NO: 2 to a subject having IVD damage for a time and under conditions sufficient to reduce or prevent IVD degeneration in the subject,
wherein said human GDF-6 is administered to a plurality of sites within an IVD having damage so as to permit said human GDF-6 to disperse or distribute evenly throughout the nucleus pulposus.

2. The method according to claim 1, wherein the human GDF-6 is administered for a time and under conditions sufficient to enhance or induce collagen synthesis in an IVD cell, to enhance collagen levels in an IVD or a tissue thereof, or a combination thereof.

3. The method according to claim 1, wherein the human GDF-6 is cell-free.

4. The method according to claim 1, wherein the human GDF-6 is administered to the plurality of sites in a single administration.

5. The method according to claim 1, wherein the human GDF-6 is administered in a patterned manner.

6. The method according to claim 1, wherein the human GDF-6 is administered via a medical device comprising a delivery conduit having a proximal end attachable to a source of said human GDF-6 and an emitter structure at a distal end of the delivery conduit, wherein the emitter structure defines a plurality of spaced discharge apertures through which said human GDF-6 is delivered.

7. A method for treating intervertebral disc (IVD) degeneration in a subject having IVD damage, said method comprising
administering a human GDF-6 to a subject having IVD damage for a time and under conditions sufficient to enhance or induce collagen synthesis in an IVD cell, to enhance collagen levels in an IVD or a tissue thereof in the subject, or a combination thereof,
wherein said human GDF-6 is administered to a plurality of sites within an IVD having damage so as to permit said human GDF-6 to disperse or distribute evenly throughout the nucleus pulposus, and
wherein said human GDF-6 comprises a dimer comprising a C-terminal fragment of at least 120 amino acid residues of SEQ ID NO: 2.

8. The method according to claim 7, wherein the human GDF-6 is administered to the plurality of sites in a single administration.

9. The method according to claim 7, wherein the human GDF-6 is administered in a patterned manner.

10. The method according to claim 7, wherein the human GDF-6 is administered via a medical device comprising a delivery conduit having a proximal end attachable to a source of said human GDF-6 and an emitter structure at a distal end of the delivery conduit, wherein the emitter structure defines a plurality of spaced discharge apertures through which said human GDF-6 is delivered.

11. A method for administering a human GDF-6 to a subject, said method comprising:
accessing a region of an IVD by surgical intervention or injection;
providing or obtaining a medical device comprising the human GDF-6, wherein the medical device comprises a delivery conduit having a proximal end attachable to a source of the human GDF-6 and an emitter structure at a distal end of the delivery conduit, wherein the emitter structure defines a plurality of spaced discharge apertures through which the human GDF-6 is delivered to a plurality of sites;

inserting the emitter structure of the medical device at least partially into the accessed region of the IVD;

manipulating the emitter structure so that the emitter structure is positioned within the IVD; and discharging the human GDF-6 through the apertures of the device so as to administer said human GDF-6 to a plurality of sites within the IVD, thereby administering the human GDF-6 to the subject, wherein the human GDF-6 comprises a dimer comprising a C-terminal fragment of at least 120 amino acid residues of SEQ ID NO: 2.

12. A process for preventing or treating intervertebral disc (IVD) degeneration in a subject having IVD damage, said process comprising administering a human GDF-6 comprising a dimer comprising a C-terminal fragment of at least 120 amino acid residues of SEQ ID NO:2 to a subject having IVD damage for a time and under conditions sufficient to reduce or prevent IVD degeneration in the subject, wherein said process comprises administering the human GDF 6 to the subject by performing the method of claim 8 and resting the subject for a time and under conditions sufficient to reduce or prevent IVD degeneration in the subject.

13. The method of claim 11, comprising manipulating the emitter structure so that the emitter structure at least partially surrounds or is positioned within the nucleus pulposus, at least partially surrounds or is positioned within a region of the IVD defined by an internal wall of the annulus fibrosus, or a combination thereof, and wherein said discharging administers said human GDF-6 to a plurality of sites within a nucleus pulposus, a plurality of sites within a region of the IVD defined by an internal wall of the annulus fibrosus, or a combination thereof.

14. The method of claim 7, wherein said human GDF-6 is administered to a plurality of sites within a nucleus pulposus, a plurality of sites adjacent to at least a portion of a nucleus pulposus, a plurality of sites within a region of the IVD defined by an internal wall of the annulus fibrosus, or a combination thereof.

* * * * *

SEQUENCE LISTING

<160> NUMBER OF SEQ ID NOS: 37

<210> SEQ ID NO 1
<211> LENGTH: 3716
<212> TYPE: DNA
<213> ORGANISM: Homo sapiens
<220> FEATURE:
<221> NAME/KEY: CDS
<222> LOCATION: (101)..(1468)

<400> SEQUENCE: 1

| | |
|---|---|
| cccgaggagc cgggccccgg ccgctgtcca gccgctccgt gccccgcgcg tcctgcgccg | 60 |
| ccgccaccgc ctcctgggga gacgcagcca cttgcccgcc atg gat act ccc agg<br>                                 Met Asp Thr Pro Arg<br>                                  1        5 | 115 |
| gtc ctg ctc tcg gcc gtc ttc ctc atc agt ttt ctg tgg gat ttg ccc<br>Val Leu Leu Ser Ala Val Phe Leu Ile Ser Phe Leu Trp Asp Leu Pro<br>          10           15          20 | 163 |
| ggt ttc cag cag gct tcc atc tca tcc tcc tcg tcg tcc gcc gag ctg<br>Gly Phe Gln Gln Ala Ser Ile Ser Ser Ser Ser Ser Ala Glu Leu<br>       25           30          35 | 211 |
| ggt tcc acc aag ggc atg cga agc cgc aag gaa ggc aag atg cag cgg<br>Gly Ser Thr Lys Gly Met Arg Ser Arg Lys Glu Gly Lys Met Gln Arg<br>   40          45          50 | 259 |
| gcg ccg cgc gac agt gac gcg ggc cgg gag ggc cag gaa cca cag ccg<br>Ala Pro Arg Asp Ser Asp Ala Gly Arg Glu Gly Gln Glu Pro Gln Pro<br>55          60           65 | 307 |
| cgg cct cag gac gaa ccc cgg gct cag cag ccc cgg gcg cag gag ccg<br>Arg Pro Gln Asp Glu Pro Arg Ala Gln Gln Pro Arg Ala Gln Glu Pro<br>70          75          80          85 | 355 |
| cca ggc agg ggt ccg cgc gtg gtg ccc cac gag tac atg ctg tca atc<br>Pro Gly Arg Gly Pro Arg Val Val Pro His Glu Tyr Met Leu Ser Ile<br>       90           95          100 | 403 |
| tac agg act tac tcc atc gct gag aag ctg ggc atc aat gcc agc ttt<br>Tyr Arg Thr Tyr Ser Ile Ala Glu Lys Leu Gly Ile Asn Ala Ser Phe<br>     105          110          115 | 451 |
| ttc cag tct tcc aag tcg gct aat acg atc acc agc ttt gta gac agg<br>Phe Gln Ser Ser Lys Ser Ala Asn Thr Ile Thr Ser Phe Val Asp Arg<br>  120         125          130 | 499 |
| gga cta gac gat ctc tcg cac act cct ctc cgg aga cag aag tat ttg<br>Gly Leu Asp Asp Leu Ser His Thr Pro Leu Arg Arg Gln Lys Tyr Leu<br>135         140          145 | 547 |
| ttt gat gtg tcc atg ctc tca gac aaa gaa gag ctg gtg ggc gcg gag<br>Phe Asp Val Ser Met Leu Ser Asp Lys Glu Glu Leu Val Gly Ala Glu<br>150          155          160         165 | 595 |
| ctg cgg ctc ttt cgc cag gcg ccc tca gcg ccc tgg ggg cca cca gcc<br>Leu Arg Leu Phe Arg Gln Ala Pro Ser Ala Pro Trp Gly Pro Pro Ala<br>       170          175         180 | 643 |
| ggg ccg ctc cac gtg cag ctc ttc cct tgc ctt tcg ccc cta ctg ctg<br>Gly Pro Leu His Val Gln Leu Phe Pro Cys Leu Ser Pro Leu Leu Leu<br>     185          190         195 | 691 |
| gac gcg cgg acc ctg gac ccg cag ggg gcg ccg ccg gcc ggc tgg gaa<br>Asp Ala Arg Thr Leu Asp Pro Gln Gly Ala Pro Pro Ala Gly Trp Glu<br>  200         205          210 | 739 |
| gtc ttc gac gtg tgg cag ggc ctg cgc cac cag ccc tgg aag cag ctg<br>Val Phe Asp Val Trp Gln Gly Leu Arg His Gln Pro Trp Lys Gln Leu<br>215          220          225 | 787 |
| tgc ttg gag ctg cgg gcc gca tgg ggc gag ctg gac gcc ggg gag gcc<br>Cys Leu Glu Leu Arg Ala Ala Trp Gly Glu Leu Asp Ala Gly Glu Ala<br>230          235          240         245 | 835 |

```
gag gcg cgc gcg cgg gga ccc cag caa ccg ccg ccc ccg gac ctg cgg        883
Glu Ala Arg Ala Arg Gly Pro Gln Gln Pro Pro Pro Pro Asp Leu Arg
            250                 255                 260 agt ctg ggc ttc ggc cgg agg gtg cgg cct ccc cag gag cgg gcc ctg        931
Ser Leu Gly Phe Gly Arg Arg Val Arg Pro Pro Gln Glu Arg Ala Leu
            265                 270                 275 ctg gtg gta ttc acc aga tcc cag cgc aag aac ctg ttc gca gag atg        979
Leu Val Val Phe Thr Arg Ser Gln Arg Lys Asn Leu Phe Ala Glu Met
            280                 285                 290 cgc gag cag ctg ggc tcg gcc gag gct gcg ggc ccg gcg ggc gcc            1027
Arg Glu Gln Leu Gly Ser Ala Glu Ala Ala Gly Pro Gly Ala Gly Ala
        295                 300                 305 gag ggg tcg tgg ccg ccg ccg tcg ggc gcc ccg gat gcc agg cct tgg        1075
Glu Gly Ser Trp Pro Pro Pro Ser Gly Ala Pro Asp Ala Arg Pro Trp
310                 315                 320                 325 ctg ccc tcg ccc ggc cgc cgg cgg cgc acg gcc ttc gcc agt cgc            1123
Leu Pro Ser Pro Gly Arg Arg Arg Arg Thr Ala Phe Ala Ser Arg
                330                 335                 340 cat ggc aag cgg cac ggc aag aag tcc agg cta cgc tgc agc aag aag        1171
His Gly Lys Arg His Gly Lys Lys Ser Arg Leu Arg Cys Ser Lys Lys
            345                 350                 355 ccc ctg cac gtg aac ttc aag gag ctg ggc tgg gac gac tgg att atc        1219
Pro Leu His Val Asn Phe Lys Glu Leu Gly Trp Asp Asp Trp Ile Ile
            360                 365                 370 gcg ccc ctg gag tac gag gcc tat cac tgc gag ggt gta tgc gac ttc        1267
Ala Pro Leu Glu Tyr Glu Ala Tyr His Cys Glu Gly Val Cys Asp Phe
            375                 380                 385 ccg ctg cgc tcg cac ctg gag ccc acc aac cac gcc atc atc cag acg       1315
Pro Leu Arg Ser His Leu Glu Pro Thr Asn His Ala Ile Ile Gln Thr
390                 395                 400                 405 ctg atg aac tcc atg gac ccc ggc tcc acc ccg ccc agc tgc tgc gtg        1363
Leu Met Asn Ser Met Asp Pro Gly Ser Thr Pro Pro Ser Cys Cys Val
            410                 415                 420 ccc acc aaa ttg act ccc atc agc att cta tac atc gac gcg ggc aat       1411
Pro Thr Lys Leu Thr Pro Ile Ser Ile Leu Tyr Ile Asp Ala Gly Asn
            425                 430                 435 aat gtg gtc tac aag cag tac gag gac atg gtg gtg gag tcg tgc ggc        1459
Asn Val Val Tyr Lys Gln Tyr Glu Asp Met Val Val Glu Ser Cys Gly
            440                 445                 450 tgc agg tag cggtgccttt cccgccgcct tggcccggaa ccaaggtggg                1508
Cys Arg
    455 ccaaggtccg ccttgcaggg gaggcctggc tgcagagagg cggaggagga agctggcgct     1568 gggggaggct gagggtgagg gaacagcctg gatgtgagag ccggtgggag agaagggagc     1628 gcagccttcc cagtaacttc tacctgccag cccagaggga aatatggatt ttcacacctt     1688 gcctggccac cctggaaaaa caagccaagg aggatttctt ttgttctgtt ttctctctct     1748 ctctctctct ctctctctct ctctctctct ctctctctat tactgtggct ttggatttcc     1808 ttatgtgtct tacaggcttt gatagaaggg gaggggagga gagatgcata cccgtttctc     1868 aactgctcca tggattgaaa aaataacagt ttaaaaaggg aaacaatgtg ggaggaagaa     1928 tcaccgttga cgcatcttga tttggttggt ttttacatgt gtaaagaagg tggggtctct     1988 ggccatgtca tagcccatgt cttgtgccct cccacacaga aagtgttaga tagggaaatt     2048 ggcaaaaaga atagttaagt caggaatggt cctgcctata gaagagcttt gagagaggtg     2108 ggcccacggg tgccctctc acccatttgt gtactctgtg agtttaccag ctctgccctg      2168 gcctctttcg gtaccaggaa ctggcaacct tcatctcact cctgagggcc caggtctctg     2228
```

```
ccttcattgt tgctttttct ggtgggggca aggggagctg gtatggatgg aatgacaaga    2288
attagtccaa atgaaccccc ttgaaggata atgagaaacc acaaggcctg cctctgactg    2348
gggctgacac ggaggtgcat tagcccaggc tggaggtagc ccacccaaat gcccttctg     2408 attctaattg atttctttca acagaatttg ccaaaattca gacatgcact tctaagggaa    2468
aggtgatttt ccagttcaaa aaatgggca ggagtgggga acaaacaat taacgtaaga     2528 gctacaaagg agggaaaagg aaccaagaag tagaaggagt cccatcagga gggaagatgg    2588
tgggcctcag ggaggatggg gatcaaggga caggccagga gccaggagtg gggaagggag    2648
ggatgaaagg ggacacaagt ccctgtctct gaagtttctt taaaatctga gttccctccc    2708
ctctctttga cattcctgaa agattaccag ccagcaatag cccagggctc ccccaaaaga    2768
attggttcag attgtaatta tcagttaggc aatgttttta aaacttagta atgagaaact    2828
gtgaaaagag ccaagtgtta cattgagctt ggggtgggag atggggaaca ggcagtgagg    2888
aaggagacag gggtggaatt cgtcttctgg gaggaagctg gagagagcac agtgaaattg    2948
aaatacccat tcccagatag tcaaaaacat gaactttccc ccagcctgca ccagtattgt    3008
tttcaaacat tgcccatgag taggccctt gaagagttag cttcctcctc atctttgact     3068
ataaaattgt ttaatcaatg gaatttgtac cagccttta aaaagtttta gttttcct     a 3128 agtgattttg ctctcttcca atctaaacct gttgcttgtt tggttcagag aactacaaac    3188
tgtcaaagaa agggtgggga tgataagaaa tgctaatata aaaatgctaa gtgaaaaaaa    3248
gacttggcca ggagaaataa tttaaaatgc acatttgctt tggatgcact gttgttctgt    3308
taaggctgta tatatttgtt tatttaaggt gactgaaagt gcaaagagga aatggacagc    3368
atgcaattca tcctaatgta caaaacgtta tatgcactca aatgttataa tttctaatat    3428
ttttaaagtt tatattcgag ttgtacaaag ttaagcatta atcagatatt tcattttttc    3488
ataatgttac cattttctta aatattatta caaaatttta agtctgtcta atggagagtt    3548
ttttttaaac tgtctacctc atataataca agtatttaca acgctaaagt taccagaggt    3608
caatgaataa tcaaaacatt ttttacagta cacctttcct ggatgatatg caatcgaatg    3668
ctatattatt aaacgcattt ttctccttat taaaaaaaaa aaaaaaaa              3716
```

<210> SEQ ID NO 2
<211> LENGTH: 455
<212> TYPE: PRT
<213> ORGANISM: Homo sapiens

<400> SEQUENCE: 2

```
Met Asp Thr Pro Arg Val Leu Leu Ser Ala Val Phe Leu Ile Ser Phe
1               5                  10                  15

Leu Trp Asp Leu Pro Gly Phe Gln Gln Ala Ser Ile Ser Ser Ser Ser
            20                  25                  30

Ser Ser Ala Glu Leu Gly Ser Thr Lys Gly Met Arg Ser Arg Lys Glu
        35                  40                  45

Gly Lys Met Gln Arg Ala Pro Arg Asp Ser Asp Ala Gly Arg Glu Gly
    50                  55                  60

Gln Glu Pro Gln Pro Arg Pro Gln Asp Glu Pro Arg Ala Gln Gln Pro
65                  70                  75                  80

Arg Ala Gln Glu Pro Pro Gly Arg Gly Pro Arg Val Val Pro His Glu
                85                  90                  95

Tyr Met Leu Ser Ile Tyr Arg Thr Tyr Ser Ile Ala Glu Lys Leu Gly
                100                 105                 110
```

Ile Asn Ala Ser Phe Phe Gln Ser Ser Lys Ser Ala Asn Thr Ile Thr
            115                 120                 125

Ser Phe Val Asp Arg Gly Leu Asp Asp Leu Ser His Thr Pro Leu Arg
        130                 135                 140

Arg Gln Lys Tyr Leu Phe Asp Val Ser Met Leu Ser Asp Lys Glu Glu
145                 150                 155                 160

Leu Val Gly Ala Glu Leu Arg Leu Phe Arg Gln Ala Pro Ser Ala Pro
                165                 170                 175

Trp Gly Pro Pro Ala Gly Pro Leu His Val Gln Leu Phe Pro Cys Leu
            180                 185                 190

Ser Pro Leu Leu Leu Asp Ala Arg Thr Leu Asp Pro Gln Gly Ala Pro
        195                 200                 205

Pro Ala Gly Trp Glu Val Phe Asp Val Trp Gln Gly Leu Arg His Gln
210                 215                 220

Pro Trp Lys Gln Leu Cys Leu Glu Leu Arg Ala Ala Trp Gly Glu Leu
225                 230                 235                 240

Asp Ala Gly Glu Ala Glu Ala Arg Ala Arg Gly Pro Gln Gln Pro Pro
                245                 250                 255

Pro Pro Asp Leu Arg Ser Leu Gly Phe Gly Arg Arg Val Arg Pro Pro
            260                 265                 270

Gln Glu Arg Ala Leu Leu Val Val Phe Thr Arg Ser Gln Arg Lys Asn
        275                 280                 285

Leu Phe Ala Glu Met Arg Glu Gln Leu Gly Ser Ala Glu Ala Ala Gly
        290                 295                 300

Pro Gly Ala Gly Ala Glu Gly Ser Trp Pro Pro Ser Gly Ala Pro
305                 310                 315                 320

Asp Ala Arg Pro Trp Leu Pro Ser Pro Gly Arg Arg Arg Arg Arg Thr
                325                 330                 335

Ala Phe Ala Ser Arg His Gly Lys Arg His Gly Lys Lys Ser Arg Leu
            340                 345                 350

Arg Cys Ser Lys Lys Pro Leu His Val Asn Phe Lys Glu Leu Gly Trp
        355                 360                 365

Asp Asp Trp Ile Ile Ala Pro Leu Glu Tyr Glu Ala Tyr His Cys Glu
        370                 375                 380

Gly Val Cys Asp Phe Pro Leu Arg Ser His Leu Glu Pro Thr Asn His
385                 390                 395                 400

Ala Ile Ile Gln Thr Leu Met Asn Ser Met Asp Pro Gly Ser Thr Pro
                405                 410                 415

Pro Ser Cys Cys Val Pro Thr Lys Leu Thr Pro Ile Ser Ile Leu Tyr
            420                 425                 430

Ile Asp Ala Gly Asn Asn Val Val Tyr Lys Gln Tyr Glu Asp Met Val
        435                 440                 445

Val Glu Ser Cys Gly Cys Arg
    450                 455

<210> SEQ ID NO 3
<211> LENGTH: 174
<212> TYPE: PRT
<213> ORGANISM: Homo sapiens

<400> SEQUENCE: 3

Thr Arg Ser Gln Arg Lys Asn Leu Phe Ala Glu Met Arg Glu Gln Leu
1               5                   10                  15

Gly Ser Ala Glu Ala Ala Gly Pro Gly Ala Gly Ala Glu Gly Ser Trp

```
            20                  25                  30
Pro Pro Pro Ser Gly Ala Pro Asp Ala Arg Pro Trp Leu Pro Ser Pro
         35                  40                  45

Gly Arg Arg Arg Arg Thr Ala Phe Ala Ser Arg His Gly Lys Arg
 50                  55                  60

His Gly Lys Lys Ser Arg Leu Arg Cys Ser Lys Lys Pro Leu His Val
 65                  70                  75                  80

Asn Phe Lys Glu Leu Gly Trp Asp Asp Trp Ile Ile Ala Pro Leu Glu
                 85                  90                  95

Tyr Glu Ala Tyr His Cys Glu Gly Val Cys Asp Phe Pro Leu Arg Ser
            100                 105                 110

His Leu Glu Pro Thr Asn His Ala Ile Ile Gln Thr Leu Met Asn Ser
        115                 120                 125

Met Asp Pro Gly Ser Thr Pro Pro Ser Cys Cys Val Pro Thr Lys Leu
    130                 135                 140

Thr Pro Ile Ser Ile Leu Tyr Ile Asp Ala Gly Asn Asn Val Val Tyr
145                 150                 155                 160

Lys Gln Tyr Glu Asp Met Val Val Glu Ser Cys Gly Cys Arg
                165                 170

<210> SEQ ID NO 4
<211> LENGTH: 1940
<212> TYPE: DNA
<213> ORGANISM: Homo sapiens
<220> FEATURE:
<221> NAME/KEY: CDS
<222> LOCATION: (236)..(1147)

<400> SEQUENCE: 4
agggcccgga gccggcgagt gctcccggga actctgcctg cgcggcggca gcgaccggag      60
gccaggccca gcacgccgga gctggcctgc tggggagggg cgggaggcgc gcgcgggagg     120
gtccgcccgg ccagggcccc gggcgctcgc agaggccggc cgcgctccca gcccgccgg     180 agcccatgcc cggcggctgg ccagtgctgc ggcagaaggg ggggcccggc tctgc atg     238
                                                                 Met
                                                                  1 gcc ccg gct gct gac atg act tct ttg cca ctc ggt gtc aaa gtg gag     286
Ala Pro Ala Ala Asp Met Thr Ser Leu Pro Leu Gly Val Lys Val Glu
          5                  10                  15 gac tcc gcc ttc ggc aag ccg gcg ggg gga ggc gcg ggc cag gcc ccc     334
Asp Ser Ala Phe Gly Lys Pro Ala Gly Gly Gly Ala Gly Gln Ala Pro
     20                  25                  30 agc gcc gcc gcg gcc acg gca gcc gcc atg ggc gcg gac gag gag ggg     382
Ser Ala Ala Ala Ala Thr Ala Ala Ala Met Gly Ala Asp Glu Glu Gly
 35                  40                  45 gcc aag ccc aaa gtg tcc cct tcg ctc ctg ccc ttc agc gtg gag gcg     430
Ala Lys Pro Lys Val Ser Pro Ser Leu Leu Pro Phe Ser Val Glu Ala
 50                  55                  60                  65 ctc atg gcc gac cac agg aag ccg ggg gcc aag gag agc gcc ctg gcg     478
Leu Met Ala Asp His Arg Lys Pro Gly Ala Lys Glu Ser Ala Leu Ala
                 70                  75                  80 ccc tcc gag ggc gtg cag gcg gcg ggt ggc tcg gcg cag cca ctg ggc     526
Pro Ser Glu Gly Val Gln Ala Ala Gly Gly Ser Ala Gln Pro Leu Gly
             85                  90                  95 gtc ccg ccg ggg tcg ctg gga gcc ccg gac gcg ccc tct tcg ccg cgg     574
Val Pro Pro Gly Ser Leu Gly Ala Pro Asp Ala Pro Ser Ser Pro Arg
        100                 105                 110 ccg ctc ggc cat ttc tcg gtg ggg gga ctc ctc aag ctg cca gaa gat     622
```

```
                Pro Leu Gly His Phe Ser Val Gly Gly Leu Leu Lys Leu Pro Glu Asp
                    115                 120                 125 gcg ctc gtc aaa gcc gag agc ccc gag aag ccc gag agg acc ccg tgg        670
Ala Leu Val Lys Ala Glu Ser Pro Glu Lys Pro Glu Arg Thr Pro Trp
130                 135                 140                 145 atg cag agc ccc cgc ttc tcc ccg ccg ccg gcc agg cgg ctg agc ccc        718
Met Gln Ser Pro Arg Phe Ser Pro Pro Pro Ala Arg Arg Leu Ser Pro
                150                 155                 160 cca gcc tgc acc ctc cgc aaa cac aag acg aac cgt aag ccg cgg acg        766
Pro Ala Cys Thr Leu Arg Lys His Lys Thr Asn Arg Lys Pro Arg Thr
            165                 170                 175 ccc ttc acc acc gcg cag ctg ctg gcg ctg gag cgc aag ttc cgc cag        814
Pro Phe Thr Thr Ala Gln Leu Leu Ala Leu Glu Arg Lys Phe Arg Gln
        180                 185                 190 aag cag tac ctg tcc atc gcc gag cgc gcg gag ttc tcc agc tcg ctc        862
Lys Gln Tyr Leu Ser Ile Ala Glu Arg Ala Glu Phe Ser Ser Ser Leu
    195                 200                 205 agc ctc act gag acg cag gtg aag ata tgg ttc cag aac cgc cgc gcc        910
Ser Leu Thr Glu Thr Gln Val Lys Ile Trp Phe Gln Asn Arg Arg Ala
210                 215                 220                 225 aag gca aag aga cta caa gag gca gag ctg gag aag ctg aag atg gcc        958
Lys Ala Lys Arg Leu Gln Glu Ala Glu Leu Glu Lys Leu Lys Met Ala
                230                 235                 240 gcc aag ccc atg ctg cca ccg gct gcc ttc ggc ctc tcc ttc cct ctc       1006
Ala Lys Pro Met Leu Pro Pro Ala Ala Phe Gly Leu Ser Phe Pro Leu
            245                 250                 255 ggc ggc ccc gca gct gta gcg gcc gcg gcg ggt gcc tcg ctc tac ggt       1054
Gly Gly Pro Ala Ala Val Ala Ala Ala Ala Gly Ala Ser Leu Tyr Gly
        260                 265                 270 gcc tct ggc ccc ttc cag cgc gcc gcg ctg cct gtg gcg ccc gtg gga       1102
Ala Ser Gly Pro Phe Gln Arg Ala Ala Leu Pro Val Ala Pro Val Gly
    275                 280                 285 ctc tac acg gcc cat gtg ggc tac agc atg tac cac ctg aca tag           1147
Leu Tyr Thr Ala His Val Gly Tyr Ser Met Tyr His Leu Thr
290                 295                 300 agggtcccag gtcgcccacc tgtgggccag ccgattcctc cagccctggt gctgtacccc     1207
cgacgtgctc ccctgctcgg caccgccagc cgccttccct ttaaccctca cactgctcca     1267
gtttcacctc tttgctccct gagttcactc tccgaagtct gatccctgcc aaaaagtggc     1327
tggaagagtc ccttagtact cttctagcat ttagatctac actctcgagt taagatggg     1387 gaaactgagg gcagagaggt taacagattt atctaaggtc cccagcagaa ttgacagttg     1447
aacagagcta gaggccatgt ctcctgcata gcttttccct gtcctgacac caggcaagaa     1507
aagcgcagag aaatcggtgt ctgacgattt tggaaatgag aacaatctca aaaaaaaaa     1567 aaaaaaaaaa aaaaaaaaaa aaaagaaaaa gagaaaaaaa agactagcca gccaggaaga     1627
tgaatcctag cttcttccat tggaaaattt aagacaagtt caacaacaaa acatttgctc     1687 tgggggggcag ggaaaacaca gatgtgttgc aaaggtaggt tgaagggacc tctctcttac    1747
cagtaccaga aacacaattg taaaattaaa aaaaaaaaaa aactctttct atttaacagt     1807
acatttgtgt ggctctcaaa catcccttg gaagggattg tgtgtactat gtaatatact      1867
gtatatttga aattttatta tcatttatat tatagctata tttgttaaat aaattaattt     1927
taagctacaa aaa                                                         1940

<210> SEQ ID NO 5
<211> LENGTH: 303
<212> TYPE: PRT
```

<213> ORGANISM: Homo sapiens

<400> SEQUENCE: 5

```
Met Ala Pro Ala Ala Asp Met Thr Ser Leu Pro Leu Gly Val Lys Val
 1               5                  10                  15
Glu Asp Ser Ala Phe Gly Lys Pro Ala Gly Gly Gly Ala Gly Gln Ala
            20                  25                  30
Pro Ser Ala Ala Ala Thr Ala Ala Met Gly Ala Asp Glu Glu
        35                  40                  45
Gly Ala Lys Pro Lys Val Ser Pro Ser Leu Leu Pro Phe Ser Val Glu
    50                  55                  60
Ala Leu Met Ala Asp His Arg Lys Pro Gly Ala Lys Glu Ser Ala Leu
65                  70                  75                  80
Ala Pro Ser Glu Gly Val Gln Ala Ala Gly Gly Ser Ala Gln Pro Leu
                85                  90                  95
Gly Val Pro Pro Gly Ser Leu Gly Ala Pro Asp Ala Pro Ser Ser Pro
            100                 105                 110
Arg Pro Leu Gly His Phe Ser Val Gly Gly Leu Leu Lys Leu Pro Glu
        115                 120                 125
Asp Ala Leu Val Lys Ala Glu Ser Pro Glu Lys Pro Glu Arg Thr Pro
130                 135                 140
Trp Met Gln Ser Pro Arg Phe Ser Pro Pro Ala Arg Arg Leu Ser
145                 150                 155                 160
Pro Pro Ala Cys Thr Leu Arg Lys His Lys Thr Asn Arg Lys Pro Arg
                165                 170                 175
Thr Pro Phe Thr Thr Ala Gln Leu Leu Ala Leu Glu Arg Lys Phe Arg
            180                 185                 190
Gln Lys Gln Tyr Leu Ser Ile Ala Glu Arg Ala Glu Phe Ser Ser Ser
        195                 200                 205
Leu Ser Leu Thr Glu Thr Gln Val Lys Ile Trp Phe Gln Asn Arg Arg
210                 215                 220
Ala Lys Ala Lys Arg Leu Gln Glu Ala Glu Leu Glu Lys Leu Lys Met
225                 230                 235                 240
Ala Ala Lys Pro Met Leu Pro Pro Ala Phe Gly Leu Ser Phe Pro
                245                 250                 255
Leu Gly Gly Pro Ala Ala Val Ala Ala Ala Gly Ala Ser Leu Tyr
            260                 265                 270
Gly Ala Ser Gly Pro Phe Gln Arg Ala Ala Leu Pro Val Ala Pro Val
        275                 280                 285
Gly Leu Tyr Thr Ala His Val Gly Tyr Ser Met Tyr His Leu Thr
290                 295                 300
```

<210> SEQ ID NO 6
<211> LENGTH: 2224
<212> TYPE: DNA
<213> ORGANISM: Homo sapiens
<220> FEATURE:
<221> NAME/KEY: CDS
<222> LOCATION: (89)..(892)

<400> SEQUENCE: 6

```
tcccgtctcc gcagcaaaaa agtttgagtc gccgctgccg ggttgccagc ggagtcgcgc      60
gtcgggagct acgtagggca gagaagtc atg gct tct ccg tcc aaa ggc aat       112
                              Met Ala Ser Pro Ser Lys Gly Asn
                               1               5 gac ttg ttt tcg ccc gac gag gag ggc cca gca gtg gtg gcc gga cca      160
```

```
         Asp Leu Phe Ser Pro Asp Glu Glu Gly Pro Ala Val Val Ala Gly Pro
          10                  15                  20 ggc ccg ggg cct ggg ggc gcc gag ggg gcc gcg gag gag cgc cgc gtc           208
Gly Pro Gly Pro Gly Gly Ala Glu Gly Ala Ala Glu Glu Arg Arg Val
 25                  30                  35                  40 aag gtc tcc agc ctg ccc ttc agc gtg gag gcg ctc atg tcc gac aag           256
Lys Val Ser Ser Leu Pro Phe Ser Val Glu Ala Leu Met Ser Asp Lys
                 45                  50                  55 aag ccg ccc aag gag gcg tcc ccg ctg ccg gcc gaa agc gcc tcg gcc           304
Lys Pro Pro Lys Glu Ala Ser Pro Leu Pro Ala Glu Ser Ala Ser Ala
             60                  65                  70 ggg gcc acc ctg cgg cca ctg ctg ctg tcg ggg cac ggc gct cgg gaa           352
Gly Ala Thr Leu Arg Pro Leu Leu Leu Ser Gly His Gly Ala Arg Glu
         75                  80                  85 gcg cac agc ccc ggg ccg ctg gtg aag ccc ttc gag acc gcc tcg gtc           400
Ala His Ser Pro Gly Pro Leu Val Lys Pro Phe Glu Thr Ala Ser Val
     90                  95                 100 aag tcg gaa aat tca gaa gat gga gcg gcg tgg atg cag gaa ccc ggc           448
Lys Ser Glu Asn Ser Glu Asp Gly Ala Ala Trp Met Gln Glu Pro Gly
105                 110                 115                 120 cga tat tcg ccg ccg cca aga cat atg agc cct acc acc tgc acc ctg           496
Arg Tyr Ser Pro Pro Pro Arg His Met Ser Pro Thr Thr Cys Thr Leu
                125                 130                 135 agg aaa cac aag acc aat cgg aag ccg cgc acg ccc ttt acc aca tcc           544
Arg Lys His Lys Thr Asn Arg Lys Pro Arg Thr Pro Phe Thr Thr Ser
            140                 145                 150 cag ctc ctc gcc ctg gag cgc aag ttc cgt cag aaa cag tac ctc tcc           592
Gln Leu Leu Ala Leu Glu Arg Lys Phe Arg Gln Lys Gln Tyr Leu Ser
        155                 160                 165 att gca gag cgt gca gag ttc tcc agc tct ctg aac ctc aca gag acc           640
Ile Ala Glu Arg Ala Glu Phe Ser Ser Ser Leu Asn Leu Thr Glu Thr
    170                 175                 180 cag gtc aaa atc tgg ttc cag aac cga agg gcc aag gcg aaa aga ctg           688
Gln Val Lys Ile Trp Phe Gln Asn Arg Arg Ala Lys Ala Lys Arg Leu
185                 190                 195                 200 cag gag gca gaa ctg gaa aag ctg aaa atg gct gca aaa cct atg ctg           736
Gln Glu Ala Glu Leu Glu Lys Leu Lys Met Ala Ala Lys Pro Met Leu
                205                 210                 215 ccc tcc agc ttc agt ctc cct ttc ccc atc agc tcg ccc ctg cag gca           784
Pro Ser Ser Phe Ser Leu Pro Phe Pro Ile Ser Ser Pro Leu Gln Ala
            220                 225                 230 gcg tcc ata tat gga gca tcc tac ccg ttc cat aga cct gtg ctt ccc           832
Ala Ser Ile Tyr Gly Ala Ser Tyr Pro Phe His Arg Pro Val Leu Pro
        235                 240                 245 atc ccg cct gtg gga ctc tat gcc acg cca gtg gga tat ggc atg tac           880
Ile Pro Pro Val Gly Leu Tyr Ala Thr Pro Val Gly Tyr Gly Met Tyr
    250                 255                 260 cac ctg tcc taa ggaagaccag atcaatagac tccatgatgg atgcttgttt               932
His Leu Ser
265 caaagggttt cctctccctc tccacgaagg cagtaccagc cagtactcct gctctgctaa        992 ccctgcgtgc accaccctaa gcggctaggc tgacagggcc acacgacata gctgaaattt       1052 gttctgtagg cggaggcacc aagccctgtt ttcttggtgt aatcttccag atgccccctt       1112 ttcctttcac aaagattggc tctgatggtt tttatgtata aatatatata tataataaaa       1172 tataatacat ttttatacag cagacgtaaa aattcaaatt attttaaaag gcaaaattta       1232 tatacatatg tgcttttttt ctatatctca ccttcccaaa agacactgtg taagtccatt       1292
```

-continued

```
tgttgtattt tcttaaagag ggagacaaat tatttgcaaa atgtgctaaa gtcaatgatt    1352
tttacgggat tattgacttc tgcttatgga aaacaaagaa acagacacaa tgcacacaga    1412
aaatattaga tatggagaga ttattcaaag tgaaggggac acatcatatt tctgcatttt    1472
acttgcatta aaagaaacct ctttatatac tacagttgtt cctatctctc ccccgccccc    1532
caccgcccca ccacacacat attttttaaag ttttttccttt tttaagaata ttttttgtaag 1592 accaatacct gggatgagaa gaatcctgag actgcctgga ggtgaggtag aaaattagaa    1652
atacttccta attcttctca aggctgttgg taactttatt tcagataatt ggagagtaaa    1712
atgttaaaac ctgttgagag gaattgatgg tttctgagaa atactaggta cattcatcct    1772
cacagattgc aaaggtgatt tgggtgnggg tttagtaatt ttctgcttaa aaaatgagta    1832
tcttgtaacc attacctata tgctaaatat tcttgaacaa ttagtagatc cagaaagaaa    1892
aaaaaatatg ctttctctgt gtgtgtacct gttgtatgtc ctaaacttat tagaaaattt    1952
tatatacttt tttacatgtt gggggggcaga aggtaaagcc atgttttgac ttggtgaaaa    2012
tgggattgtc aaacagccca ttaagttccc tggtatttca ccttcctgtc catctgtccc    2072
ctccctccgg tataccttta tccctttgaa agggtgcttg tacaatttga tatatttttat  2132 tgaagagtta tctcttattc tgaattaaat taagcatttg ttttattgca gtaaagtttg    2192
tccaaactca caattaaaaa aaaaaaaaaa aa                                  2224
```

<210> SEQ ID NO 7
<211> LENGTH: 267
<212> TYPE: PRT
<213> ORGANISM: Homo sapiens

<400> SEQUENCE: 7

```
Met Ala Ser Pro Ser Lys Gly Asn Asp Leu Phe Ser Pro Asp Glu Glu
1               5                   10                  15

Gly Pro Ala Val Val Ala Gly Pro Gly Pro Gly Pro Gly Gly Ala Glu
            20                  25                  30

Gly Ala Ala Glu Glu Arg Arg Val Lys Val Ser Ser Leu Pro Phe Ser
        35                  40                  45

Val Glu Ala Leu Met Ser Asp Lys Lys Pro Pro Lys Glu Ala Ser Pro
    50                  55                  60

Leu Pro Ala Glu Ser Ala Ser Ala Gly Ala Thr Leu Arg Pro Leu Leu
65                  70                  75                  80

Leu Ser Gly His Gly Ala Arg Glu Ala His Ser Pro Gly Pro Leu Val
                85                  90                  95

Lys Pro Phe Glu Thr Ala Ser Val Lys Ser Glu Asn Ser Glu Asp Gly
            100                 105                 110

Ala Ala Trp Met Gln Glu Pro Gly Arg Tyr Ser Pro Pro Arg His
        115                 120                 125

Met Ser Pro Thr Thr Cys Thr Leu Arg Lys His Lys Thr Asn Arg Lys
    130                 135                 140

Pro Arg Thr Pro Phe Thr Thr Ser Gln Leu Leu Ala Leu Glu Arg Lys
145                 150                 155                 160

Phe Arg Gln Lys Gln Tyr Leu Ser Ile Ala Glu Arg Ala Glu Phe Ser
                165                 170                 175

Ser Ser Leu Asn Leu Thr Glu Thr Gln Val Lys Ile Trp Phe Gln Asn
            180                 185                 190

Arg Arg Ala Lys Ala Lys Arg Leu Gln Glu Ala Glu Leu Glu Lys Leu
        195                 200                 205
```

```
Lys Met Ala Ala Lys Pro Met Leu Pro Ser Ser Phe Ser Leu Pro Phe
    210                 215                 220

Pro Ile Ser Ser Pro Leu Gln Ala Ala Ser Ile Tyr Gly Ala Ser Tyr
225                 230                 235                 240

Pro Phe His Arg Pro Val Leu Pro Ile Pro Pro Val Gly Leu Tyr Ala
                245                 250                 255

Thr Pro Val Gly Tyr Gly Met Tyr His Leu Ser
                260                 265

<210> SEQ ID NO 8
<211> LENGTH: 10
<212> TYPE: PRT
<213> ORGANISM: Artificial Sequence
<220> FEATURE:
<223> OTHER INFORMATION: HIV-1 tat protein basic region (Protein
      Transduction Domain)

<400> SEQUENCE: 8

Gly Arg Lys Lys Arg Arg Gln Arg Arg Arg
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Polyarginine Protein Transduction Domain

<400> SEQUENCE: 9

Arg Arg Arg Arg Arg Arg Arg Arg Arg
1               5

<210> SEQ ID NO 10
<211> LENGTH: 30
<212> TYPE: DNA
<213> ORGANISM: Artificial Sequence
<220> FEATURE:
<223> OTHER INFORMATION: Primer designated 1F for amplifying BAC nucleic
      acid

<400> SEQUENCE: 10
atcccttagt tgaacacaaa aagcacaagc                                          30

<210> SEQ ID NO 11
<211> LENGTH: 30
<212> TYPE: DNA
<213> ORGANISM: Artificial Sequence
<220> FEATURE:
<223> OTHER INFORMATION: Primer designated 2F for amplifying BAC nucleic
      acid

<400> SEQUENCE: 11
ttctataaag atcatccatg ctaaacactg                                          30

<210> SEQ ID NO 12
<211> LENGTH: 28
<212> TYPE: DNA
<213> ORGANISM: Artificial Sequence
<220> FEATURE:
<223> OTHER INFORMATION: Primer designated 1R for amplifying BAC nucleic
      acid

<400> SEQUENCE: 12
tgtatgagag ttttggtggt tccacatc                                            28
```

-continued

```
<210> SEQ ID NO 13
<211> LENGTH: 25
<212> TYPE: DNA
<213> ORGANISM: Artificial Sequence
<220> FEATURE:
<223> OTHER INFORMATION: Primer designated 2R for amplifying BAC nucleic
      acid

<400> SEQUENCE: 13
gataaggact gagatatgcc ctggt                                           25

<210> SEQ ID NO 14
<211> LENGTH: 20
<212> TYPE: DNA
<213> ORGANISM: Artificial Sequence
<220> FEATURE:
<223> OTHER INFORMATION: Forward primer for amplifying Collagen Type-1

<400> SEQUENCE: 14
agacatccca ccaatcacct                                                 20

<210> SEQ ID NO 15
<211> LENGTH: 20
<212> TYPE: DNA
<213> ORGANISM: Artificial Sequence
<220> FEATURE:
<223> OTHER INFORMATION: Reverse primer for amplifying Collagen Type-1

<400> SEQUENCE: 15
agatcacgtc atcgcacaac                                                 20

<210> SEQ ID NO 16
<211> LENGTH: 21
<212> TYPE: DNA
<213> ORGANISM: Artificial Sequence
<220> FEATURE:
<223> OTHER INFORMATION: Forward primer for amplifying Collagen Type-2

<400> SEQUENCE: 16
aacactgcca acgtccagat g                                               21

<210> SEQ ID NO 17
<211> LENGTH: 21
<212> TYPE: DNA
<213> ORGANISM: Artificial Sequence
<220> FEATURE:
<223> OTHER INFORMATION: Reverse primer for amplifying Collagen Type-2

<400> SEQUENCE: 17
tcgtccagat aggcaatgct g                                               21

<210> SEQ ID NO 18
<211> LENGTH: 19
<212> TYPE: DNA
<213> ORGANISM: Artificial Sequence
<220> FEATURE:
<223> OTHER INFORMATION: Forward primer for amplifying Aggrecan

<400> SEQUENCE: 18
acgtgatcct cacggcaaa                                                  19

<210> SEQ ID NO 19
<211> LENGTH: 22
<212> TYPE: DNA
<213> ORGANISM: Artificial Sequence
<220> FEATURE:
<223> OTHER INFORMATION: Reverse primer for amplifying Aggrecan
```

-continued

<400> SEQUENCE: 19
gtgaaaggct cctcaggttc tg                                                    22

<210> SEQ ID NO 20
<211> LENGTH: 20
<212> TYPE: DNA
<213> ORGANISM: Artificial Sequence
<220> FEATURE:
<223> OTHER INFORMATION: Forward primer for amplifying GAPDH

<400> SEQUENCE: 20
acccagaaga ctgtggatgg                                                       20

<210> SEQ ID NO 21
<211> LENGTH: 20
<212> TYPE: DNA
<213> ORGANISM: Artificial Sequence
<220> FEATURE:
<223> OTHER INFORMATION: Reverse primer for amplifying GAPDH

<400> SEQUENCE: 21
agaggcaggg atgatgttct                                                       20

<210> SEQ ID NO 22
<211> LENGTH: 120
<212> TYPE: PRT
<213> ORGANISM: Artificial Sequence
<220> FEATURE:
<223> OTHER INFORMATION: Active domain of Homo sapiens GDF-6

<400> SEQUENCE: 22

Thr Ala Phe Ala Ser Arg His Gly Lys Arg His Gly Lys Lys Ser Arg
1               5                   10                  15

Leu Arg Cys Ser Lys Lys Pro Leu His Val Asn Phe Lys Glu Leu Gly
            20                  25                  30

Trp Asp Asp Trp Ile Ile Ala Pro Leu Glu Tyr Glu Ala Tyr His Cys
        35                  40                  45

Glu Gly Val Cys Asp Phe Pro Leu Arg Ser His Leu Glu Pro Thr Asn
    50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
                85                  90                  95

Tyr Ile Asp Ala Gly Asn Asn Val Val Tyr Lys Gln Tyr Glu Asp Met
            100                 105                 110

Val Val Glu Ser Cys Gly Cys Arg
        115                 120

<210> SEQ ID NO 23
<211> LENGTH: 363
<212> TYPE: DNA
<213> ORGANISM: Artificial Sequence
<220> FEATURE:
<223> OTHER INFORMATION: Nucleotide sequence encoding active domain of
      human GDF-6
<220> FEATURE:
<221> NAME/KEY: CDS
<222> LOCATION: (1)..(363)

<400> SEQUENCE: 23 acg gcc ttc gcc agt cgc cat ggc aag cgg cac ggc aag aag tcc agg      48
Thr Ala Phe Ala Ser Arg His Gly Lys Arg His Gly Lys Lys Ser Arg

```
                1               5                    10                       15
cta cgc tgc agc aag aag ccc ctg cac gtg aac ttc aag gag ctg ggc         96
Leu Arg Cys Ser Lys Lys Pro Leu His Val Asn Phe Lys Glu Leu Gly
            20                  25                  30 tgg gac gac tgg att atc gcg ccc ctg gag tac gag gcc tat cac tgc         144
Trp Asp Asp Trp Ile Ile Ala Pro Leu Glu Tyr Glu Ala Tyr His Cys
        35                  40                  45 gag ggt gta tgc gac ttc ccg ctg cgc tcg cac ctg gag ccc acc aac         192
Glu Gly Val Cys Asp Phe Pro Leu Arg Ser His Leu Glu Pro Thr Asn
    50                  55                  60 cac gcc atc atc cag acg ctg atg aac tcc atg gac ccc ggc tcc acc         240
His Ala Ile Ile Gln Thr Leu Met Asn Ser Met Asp Pro Gly Ser Thr
65                  70                  75                  80 ccg ccc agc tgc tgc gtg ccc acc aaa ttg act ccc atc agc att cta         288
Pro Pro Ser Cys Cys Val Pro Thr Lys Leu Thr Pro Ile Ser Ile Leu
                85                  90                  95 tac atc gac gcg ggc aat aat gtg gtc tac aag cag tac gag gac atg         336
Tyr Ile Asp Ala Gly Asn Asn Val Val Tyr Lys Gln Tyr Glu Asp Met
            100                 105                 110 gtg gtg gag tcg tgc ggc tgc agg tag                                     363
Val Val Glu Ser Cys Gly Cys Arg
        115                 120
```

<210> SEQ ID NO 24
<211> LENGTH: 120
<212> TYPE: PRT
<213> ORGANISM: Artificial Sequence
<220> FEATURE:
<223> OTHER INFORMATION: Synthetic Construct

<400> SEQUENCE: 24

```
Thr Ala Phe Ala Ser Arg His Gly Lys Arg His Gly Lys Lys Ser Arg
1               5                   10                  15

Leu Arg Cys Ser Lys Lys Pro Leu His Val Asn Phe Lys Glu Leu Gly
            20                  25                  30

Trp Asp Asp Trp Ile Ile Ala Pro Leu Glu Tyr Glu Ala Tyr His Cys
        35                  40                  45

Glu Gly Val Cys Asp Phe Pro Leu Arg Ser His Leu Glu Pro Thr Asn
    50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
                85                  90                  95

Tyr Ile Asp Ala Gly Asn Asn Val Val Tyr Lys Gln Tyr Glu Asp Met
            100                 105                 110

Val Val Glu Ser Cys Gly Cys Arg
        115                 120
```

<210> SEQ ID NO 25
<211> LENGTH: 136
<212> TYPE: PRT
<213> ORGANISM: Artificial Sequence
<220> FEATURE:
<223> OTHER INFORMATION: Active domain of Homo sapiens GDF-6 fused to
      N-terminal FLAG tag and TEV cleavage sequence

<400> SEQUENCE: 25

```
Met Asp Tyr Lys Asp Asp Asp Lys Glu Asn Leu Tyr Phe Gln Gly
1               5                   10                  15

Thr Ala Phe Ala Ser Arg His Gly Lys Arg His Gly Lys Lys Ser Arg
```

```
                    20                  25                  30
Leu Arg Cys Ser Lys Lys Pro Leu His Val Asn Phe Lys Glu Leu Gly
         35                  40                  45

Trp Asp Asp Trp Ile Ile Ala Pro Leu Glu Tyr Glu Ala Tyr His Cys
 50                  55                  60

Glu Gly Val Cys Asp Phe Pro Leu Arg Ser His Leu Glu Pro Thr Asn
 65                  70                  75                  80

His Ala Ile Ile Gln Thr Leu Met Asn Ser Met Asp Pro Gly Ser Thr
                 85                  90                  95

Pro Pro Ser Cys Cys Val Pro Thr Lys Leu Thr Pro Ile Ser Ile Leu
            100                 105                 110

Tyr Ile Asp Ala Gly Asn Asn Val Val Tyr Lys Gln Tyr Glu Asp Met
        115                 120                 125

Val Val Glu Ser Cys Gly Cys Arg
    130                 135

<210> SEQ ID NO 26
<211> LENGTH: 20
<212> TYPE: DNA
<213> ORGANISM: Artificial Sequence
<220> FEATURE:
<223> OTHER INFORMATION: Sequence of oligonucleotide for detecting
      collagen-type 1

<400> SEQUENCE: 26
agacatccca ccaatcacct                                                    20

<210> SEQ ID NO 27
<211> LENGTH: 20
<212> TYPE: DNA
<213> ORGANISM: Artificial Sequence
<220> FEATURE:
<223> OTHER INFORMATION: Sequence of oligonucleotide for detecting
      collagen-type 1

<400> SEQUENCE: 27
agatcacgtc atcgcacaac                                                    20

<210> SEQ ID NO 28
<211> LENGTH: 20
<212> TYPE: DNA
<213> ORGANISM: Artificial Sequence
<220> FEATURE:
<223> OTHER INFORMATION: Sequence of oligonucleotide for detecting
      collagen-type 2

<400> SEQUENCE: 28
gtgacaaagg agaggctgga                                                    20

<210> SEQ ID NO 29
<211> LENGTH: 20
<212> TYPE: DNA
<213> ORGANISM: Artificial Sequence
<220> FEATURE:
<223> OTHER INFORMATION: Sequence of oligonucleotide for detecting
      collagen-type 2

<400> SEQUENCE: 29
acctctaggg ccagaaggac                                                    20

<210> SEQ ID NO 30
<211> LENGTH: 20
<212> TYPE: DNA
```

```
<213> ORGANISM: Artificial Sequence
<220> FEATURE:
<223> OTHER INFORMATION: Sequence of oligonucleotide for detecting
      aggrecan

<400> SEQUENCE: 30
tcaacaacaa tgcccaagac                                                     20

<210> SEQ ID NO 31
<211> LENGTH: 20
<212> TYPE: DNA
<213> ORGANISM: Artificial Sequence
<220> FEATURE:
<223> OTHER INFORMATION: Sequence of oligonucleotide for detecting
      aggrecan

<400> SEQUENCE: 31
aaagttgtca ggctggttgg                                                     20

<210> SEQ ID NO 32
<211> LENGTH: 20
<212> TYPE: DNA
<213> ORGANISM: Artificial Sequence
<220> FEATURE:
<223> OTHER INFORMATION: Sequence of oligonucleotide for detecting GAPDH

<400> SEQUENCE: 32
aatcccatca ccatcttcca                                                     20

<210> SEQ ID NO 33
<211> LENGTH: 20
<212> TYPE: DNA
<213> ORGANISM: Artificial Sequence
<220> FEATURE:
<223> OTHER INFORMATION: Sequence of oligonucleotide for detecting GAPDH

<400> SEQUENCE: 33
tggactccac gacgtactca                                                     20

<210> SEQ ID NO 34
<211> LENGTH: 120
<212> TYPE: PRT
<213> ORGANISM: Artificial Sequence
<220> FEATURE:
<223> OTHER INFORMATION: retro-peptide analog of active domain of GDF-6

<400> SEQUENCE: 34

Arg Cys Gly Cys Ser Glu Val Val Met Asp Glu Tyr Gln Lys Tyr Val
1               5                   10                  15

Val Asn Asn Gly Ala Asp Ile Tyr Leu Ile Ser Ile Pro Thr Leu Lys
            20                  25                  30

Thr Pro Val Cys Cys Ser Pro Thr Ser Gly Pro Asp Met Ser Asn
        35                  40                  45

Met Leu Thr Gln Ile Ile Ala His Asn Thr Pro Glu Leu His Ser Arg
    50                  55                  60

Leu Pro Phe Asp Cys Val Gly Glu Cys His Tyr Ala Glu Tyr Glu Leu
65                  70                  75                  80

Pro Ala Ile Ile Trp Asp Asp Trp Gly Leu Glu Lys Phe Asn Val His
                85                  90                  95

Leu Pro Lys Lys Ser Cys Arg Leu Arg Ser Lys Gly His Arg Lys
            100                 105                 110

Gly His Arg Ser Ala Phe Ala Thr
        115                 120
```

```
<210> SEQ ID NO 35
<211> LENGTH: 136
<212> TYPE: PRT
<213> ORGANISM: Artificial Sequence
<220> FEATURE:
<223> OTHER INFORMATION: retro-peptide analog of an active domain of
      GDF-6 comprising a N-terminal retro FLAG tag

<400> SEQUENCE: 35

Arg Cys Gly Cys Ser Glu Val Val Met Asp Glu Tyr Gln Lys Tyr Val
1               5                   10                  15

Val Asn Asn Gly Ala Asp Ile Tyr Leu Ile Ser Ile Pro Thr Leu Lys
            20                  25                  30

Thr Pro Val Cys Cys Ser Pro Pro Thr Ser Gly Pro Asp Met Ser Asn
        35                  40                  45

Met Leu Thr Gln Ile Ile Ala His Asn Thr Pro Glu Leu His Ser Arg
    50                  55                  60

Leu Pro Phe Asp Cys Val Gly Glu Cys His Tyr Ala Glu Tyr Glu Leu
65                  70                  75                  80

Pro Ala Ile Ile Trp Asp Asp Trp Gly Leu Glu Lys Phe Asn Val His
                85                  90                  95

Leu Pro Lys Lys Ser Cys Arg Leu Arg Ser Lys Lys Gly His Arg Lys
            100                 105                 110

Gly His Arg Ser Ala Phe Ala Thr Gly Gln Phe Tyr Leu Asn Glu Lys
        115                 120                 125

Asp Asp Asp Asp Lys Tyr Asp Met
    130                 135

<210> SEQ ID NO 36
<211> LENGTH: 120
<212> TYPE: PRT
<213> ORGANISM: Artificial Sequence
<220> FEATURE:
<223> OTHER INFORMATION: retro-inverted peptide analog of active domain
      of GDF-6 wherein each amino acid other than glycine is a D-amino
      acid

<400> SEQUENCE: 36

Arg Cys Gly Cys Ser Glu Val Val Met Asp Glu Tyr Gln Lys Tyr Val
1               5                   10                  15

Val Asn Asn Gly Ala Asp Ile Tyr Leu Ile Ser Ile Pro Thr Leu Lys
            20                  25                  30

Thr Pro Val Cys Cys Ser Pro Pro Thr Ser Gly Pro Asp Met Ser Asn
        35                  40                  45

Met Leu Thr Gln Ile Ile Ala His Asn Thr Pro Glu Leu His Ser Arg
    50                  55                  60

Leu Pro Phe Asp Cys Val Gly Glu Cys His Tyr Ala Glu Tyr Glu Leu
65                  70                  75                  80

Pro Ala Ile Ile Trp Asp Asp Trp Gly Leu Glu Lys Phe Asn Val His
                85                  90                  95

Leu Pro Lys Lys Ser Cys Arg Leu Arg Ser Lys Lys Gly His Arg Lys
            100                 105                 110

Gly His Arg Ser Ala Phe Ala Thr
        115                 120

<210> SEQ ID NO 37
<211> LENGTH: 136
<212> TYPE: PRT
```

-continued

```
<213> ORGANISM: Artificial Sequence
<220> FEATURE:
<223> OTHER INFORMATION: retroinverted peptide analog of an active
      domain of GDF-6 comprising a N-terminal retro FLAG tag wherein
      each amino acid other than glycine is a D-amino acid

<400> SEQUENCE: 37

Arg Cys Gly Cys Ser Glu Val Val Met Asp Glu Tyr Gln Lys Tyr Val
1               5                   10                  15

Val Asn Asn Gly Ala Asp Ile Tyr Leu Ile Ser Ile Pro Thr Leu Lys
            20                  25                  30

Thr Pro Val Cys Cys Ser Pro Pro Thr Ser Gly Pro Asp Met Ser Asn
            35                  40                  45

Met Leu Thr Gln Ile Ile Ala His Asn Thr Pro Glu Leu His Ser Arg
    50                  55                  60

Leu Pro Phe Asp Cys Val Gly Glu Cys His Tyr Ala Glu Tyr Glu Leu
65                  70                  75                  80

Pro Ala Ile Ile Trp Asp Asp Trp Gly Leu Glu Lys Phe Asn Val His
                85                  90                  95

Leu Pro Lys Lys Ser Cys Arg Leu Arg Ser Lys Lys Gly His Arg Lys
                100                 105                 110

Gly His Arg Ser Ala Phe Ala Thr Gly Gln Phe Tyr Leu Asn Glu Lys
            115                 120                 125

Asp Asp Asp Asp Lys Tyr Asp Met
            130                 135
```